US010064584B2

(12) United States Patent
Yared

(10) Patent No.: US 10,064,584 B2
(45) Date of Patent: Sep. 4, 2018

(54) COMBINED X-RAY AND OPTICAL TOMOGRAPHIC IMAGING SYSTEM

(75) Inventor: Wael I. Yared, Lexington, MA (US)

(73) Assignee: VisEn Medical, Inc., Woburn, MA (US)

( * ) Notice: Subject to any disclaimer, the term of this patent is extended or adjusted under 35 U.S.C. 154(b) by 1060 days.

(21) Appl. No.: 11/643,758

(22) Filed: Dec. 21, 2006

(65) Prior Publication Data
US 2007/0238957 A1    Oct. 11, 2007

Related U.S. Application Data

(60) Provisional application No. 60/753,590, filed on Dec. 22, 2005.

(51) Int. Cl.
*A61B 6/03* (2006.01)
*A61B 5/00* (2006.01)
(Continued)

(52) U.S. Cl.
CPC ............ *A61B 6/032* (2013.01); *A61B 5/0035* (2013.01); *A61B 5/0059* (2013.01); *A61B 5/0064* (2013.01); *A61B 5/1077* (2013.01); *A61B 6/4014* (2013.01); *A61B 6/4417* (2013.01); *A61B 6/482* (2013.01); *A61B 6/508* (2013.01);
(Continued)

(58) Field of Classification Search
USPC ......... 600/476, 309–312, 473, 478; 250/207, 250/362, 208.1; 356/432, 435
See application file for complete search history.

(56) References Cited

U.S. PATENT DOCUMENTS 4,981,977 A    1/1991  Southwick et al.
5,268,486 A   12/1993  Waggoner et al.
(Continued)

FOREIGN PATENT DOCUMENTS

EP       1065250 A1     1/2001
WO    WO-9740104 A1    10/1997
(Continued)

OTHER PUBLICATIONS

"Optical tomographic reconstruction in a complex head model using a priori region boundary information" by M. Schweiger et al. Phys. Med. Biol. 44, pp. 2703-2721 (1999).*
(Continued)

*Primary Examiner* — Tse Chen
*Assistant Examiner* — Jason Ip
(74) *Attorney, Agent, or Firm* — Banner & Witcoff, Ltd.

(57) ABSTRACT

The invention relates to a combined x-ray and optical (light-based) tomographic imaging system that provides functional information at greater resolution than can be achieved by optical tomography alone. The system is configured with one or more x-ray sources, x-ray detectors, light sources, and light detectors arranged on a gantry which rotates about an imaging chamber containing the object to be imaged. The system thereby allows both x-ray radiation and light to be directed into the object at multiple locations. Processing methods of the invention go beyond simple co-registration of images obtained from two or more imaging techniques. Both x-ray data and light data are used together in optical tomographic reconstruction to create the tomographic image, thereby allowing a more accurate and/ or higher resolution final image.

56 Claims, 24 Drawing Sheets

(51) Int. Cl.
 *A61B 5/107* (2006.01)
 *A61B 6/00* (2006.01)
(52) U.S. Cl.
 CPC ............ *A61B 6/5247* (2013.01); *A61B 6/485* (2013.01); *A61B 2503/40* (2013.01); *A61B 2560/0223* (2013.01)

(56) References Cited

U.S. PATENT DOCUMENTS

| | | | |
|---|---|---|---|
| 5,419,320 | A | 5/1995 | Kawaguchi et al. |
| 5,486,616 | A | 1/1996 | Waggoner et al. |
| 5,569,587 | A | 10/1996 | Waggoner |
| 5,569,766 | A | 10/1996 | Waggoner et al. |
| 5,627,027 | A | 5/1997 | Waggoner |
| 5,762,607 | A | 6/1998 | Schotland et al. |
| 5,808,044 | A | 9/1998 | Brush et al. |
| 5,877,310 | A | 3/1999 | Reddington et al. |
| 5,966,422 | A | 10/1999 | Dafni et al. |
| 6,002,003 | A | 12/1999 | Shen et al. |
| 6,004,536 | A | 12/1999 | Leung et al. |
| 6,008,373 | A | 12/1999 | Waggoner et al. |
| 6,043,025 | A | 3/2000 | Minden et al. |
| 6,127,134 | A | 10/2000 | Minden et al. |
| 6,130,094 | A | 10/2000 | Waggoner et al. |
| 6,133,445 | A | 10/2000 | Waggoner et al. |
| 6,136,612 | A | 10/2000 | Della Ciana et al. |
| 6,195,409 | B1* | 2/2001 | Chang et al. ............... 378/20 |
| 6,448,008 | B1 | 9/2002 | Caputo et al. |
| 6,574,296 | B2* | 6/2003 | Stierstorfer ............... 378/15 |
| 6,615,063 | B1* | 9/2003 | Ntziachristos et al. ...... 600/312 |
| 6,747,159 | B2 | 6/2004 | Caputo et al. |
| 6,829,324 | B2* | 12/2004 | Mori et al. ............... 378/4 |
| 7,198,404 | B2 | 4/2007 | Navab et al. |
| 7,383,076 | B2 | 6/2008 | Ntziachristos et al. |
| 7,647,091 | B2 | 1/2010 | Ntziachristos et al. |
| 7,983,740 | B2 | 7/2011 | Culver et al. |
| 2003/0076921 | A1* | 4/2003 | Mihara et al. ............... 378/4 |
| 2004/0015062 | A1 | 1/2004 | Ntziachristos et al. |
| 2004/0247076 | A1 | 12/2004 | Navab et al. |
| 2004/0249260 | A1 | 12/2004 | Wang et al. |
| 2005/0088515 | A1* | 4/2005 | Geng ............... 348/47 |
| 2005/0281371 | A1 | 12/2005 | Popescu |
| 2005/0283071 | A1 | 12/2005 | Ripoll et al. |
| 2007/0238957 | A1 | 10/2007 | Yared |
| 2008/0219933 | A1 | 9/2008 | Ntziachristos et al. |
| 2010/0078576 | A1 | 4/2010 | Ntziachristos et al. |
| 2010/0292567 | A1 | 11/2010 | Ripoll et al. |

FOREIGN PATENT DOCUMENTS

| WO | WO-9951702 A1 | 10/1999 |
|---|---|---|
| WO | WO-0121624 A1 | 3/2001 |
| WO | WO-03/102558 A1 | 12/2003 |
| WO | WO-2004/072906 A1 | 8/2004 |
| WO | WO-2004081865 A2 | 9/2004 |
| WO | WO-2005089637 | 9/2005 |

OTHER PUBLICATIONS

"Tomographic optical breast imaging guided by three-dimensional mammography" by A. Li et al, Applied Optics, vol. 42, No. 25, 2003, pp. 5181-5190.*
"A comparison study of linear reconstruction techniques for diffuse optical tomographic imaging of absorption coefficient" by R.J. Gaudette. Phys. Med. Biol. 45, 2000, pp. 1051-1070.*
"Development of Hybrid NIR/MRI Imaging System Algorithm: Use of A-Priori Information for Tumor Detection in the Female Breast" by H. Dehghani et al. IEEE. 2002. pp. 657-660.*
Achilefu et al. (2000) "Novel receptor-targeted fluorescent contrast agents for in vivo tumor imaging," *Invest. Radiol.* 35:479-485.
Ballou et al. (1997) "Tumor detection and visualization using cyanine fluorochrome-labeled antibodies," *Biotechnol. Prog.* 13:649-658.
Becker et al. (2001) "Receptor-targeted optical imaging of tumors with near-infrared fluorescent ligands," *Nature Biotech.* 19:327-331.
Beuthan (2005) "Optical diagnostics—State of the art," *Medical Laser Application* 20(2):131-134.
Boas et al. (1995) "Scattering and Imaging with Diffusing Temporal Field Correlations," *Phys. Rev. Lett.* 75:1855-1858.
Bremer et al. (2001) "In vivo molecular target assessment of matrix metalloproteinase inhibition," *Nature Med.* 7:743-748.
Bugaj et al. (2001) "Novel fluorescent contrast agents for optical imaging of in vivo tumors based on a receptor-targeted dye-peptide conjugate platform," *J. Biomed. Opt.* 6:122-133.
Macaskill et al. (1993) "Iterative approach for the numerical simulation of scattering from one- and two-dimensional rough surfaces," *Applied Optics* 32:2839-2847.
Neri et al. (1997) "Targeting by affinity-matured recombinant antibody fragments of an angiogenesis associated fibronectin isoform," *Nature Biotech.* 15:1271-1275.
Ozmen (2000) "Infrared fluorescence sensing of submicromolar calcium: pushing the limits of photoinduced electron transfer," *Tetrahedron Letters*, 41:9185-9188.
Ripoll et al. (1999) "Reflection and Transmission Coefficients," *Opt. Lett.* 24:796-798.
Ripoll et al. (2001) "Recovery of Optical Parameters in Multiple-Layered Diffusive Media: Theory and Experiments," *Opt. Soc. Am. A.* 18:821-830.
Ripoll et al. (2001) "Effect of Roughness in Nondiffusive Regions within Diffusive Media," *Opt. Soc. Am. A.* 18:940-947.
Ripoll et al. (2003) "Free-Space Propagation of Diffuse Light: Theory and Experiments," *Phyisical Review Letters* 91(10), 4 pages.
Schultz et al. (2004) "Experimental Fluorescence Tomography of Tissues with Noncontact Measurements," *IEEE Trans. on Medical Imaging* 23(4): 492-500.
Tyagi et al. (2000) "Wavelength-shifting molecular beacons," *Nat. Biotechnol.* 18:1191-1196.
Tyagi et al. (1998) "Multicolor molecular beacons for allele discrimination," *Nat. Biotechnol.* 16:49-53.
Weissleder et al. (1999) "In vivo imaging of tumors with protease-activated near-infrared fluorescent probes," *Nature Biotech.* 17:375-378.
Yaghjian (1980) "Electric dyadic green's functions in the source region," *Proc. of the IEEE* 68(2):248-263.
International Search Report for PCT/US2006/048785 dated Dec. 13, 2007, 6 pages.
International Preliminary Report on Patentability for PCT/US2006/048785 dated Jun. 24, 2008, 8 pages.
Ballou et al. (2005) "Fluorescence Imaging of Tumors In Vivo," *Current Medicinal Chemistry* 12:795-805.
Brukilacchio (2003) "A Diffuse Optical Tomography System Combined With X-Ray Mammography for Improved Breast Cancer Detection," Doctoral Dissertation, Tufts University (May 2003), 233 pages.
Driol et al. (2005) "Small Animal Multimodality Tomographic Reconstruction: Fluorescence Diffuse Optical Tomography and 3D X-Rays Reconstructions," *Molecular Imaging* 4(3):210-397.
Gehrke et al. (2005) "Application of Conventional- and Dual-Energy X-Ray Tomography in Process Engineering," *IEEE Sensors Journal* 5(2):183-187.
Goertzen et al. (2002) "Simultaneous Molecular and Anatomical Imaging of the Mouse In Vivo," *Phys. Med. Biol.* 47:4315-4328.
Hawrysz et al.(2000) "Developments Toward Diagnostic Breast Cancer Imaging Using Near Infrared Optical Measurements and Fluorescent Contrast Agents," *Neoplasia* 2(5):388-417.
Kundu et al. (2004) "Tri-modality Small Animal Imaging System," *IEEE* 3863-3867.
Li et al. (2003) "Tomographic Optical Breast Imaging Guided by Three-Dimensional Mammography," *Applied Optics* 42(25):5181-5190.
Ntziachristos et al. (1999) "Multichannel Photon Counting Instrument for Spatially Resolved Near Infrared Spectroscopy," *Review of Scientific Instruments* 70(1):193-201.

(56) References Cited

OTHER PUBLICATIONS

Zhang et al. (2005) "Coregistered Tomographic X-ray and Optical Breast Imaging: Initial Results," *Journal of Biomedical Optics* 10(2):024033-1 to 024933-9.

Ntziachristos et al. (2004) "Experimental Fluorescence Tomography of Tissues With Noncontact Measurements," *IEEE Transactions on Medical Imaging* 23(4):492-500.

Gibson, A. P. et al., Recent advances in diffuse optical imaging, Phys. Med. Biol. 50:R1-R43, (2005).

Ntziachristos, V. et al., MRI-Guided Diffuse Optical Spectroscopy of Malignant and Benign Breast Lesions, Neoplasia, 4(4):347-354 (2002).

Opponent Opposition, European Application No. 06849995.3 / EP 1 968 431, dated Dec. 17, 2015, 55 pages (includes translation).

Davis, S. C. et al, Magnetic resonance-coupled fluorescence tomography scanner for molecular imaging of tissue, Review of Scientific Instruments, AIP, Melville, NY, US, 79(6):643202-1-10 (2008).

Guven, M. et al, Diffuse optical tomography with a priori anatomical information, Physics in Medicine and Biology, 50(12):2837-2858 (2005).

Mohajerani, P. et al., FMT-PCCT: Hybrid Fluorescence Molecular Tomography—X-Ray Phase-Contrast CT Imaging of Mouse Models, IEEE Transactions on Medical Imaging, 33(7):1434-1446 (2014).

Ntziachristos, V., Fluorescence Molecular Imaging, Annu. Rev. Biomed. Eng., 8:1-33 (2006).

\* cited by examiner

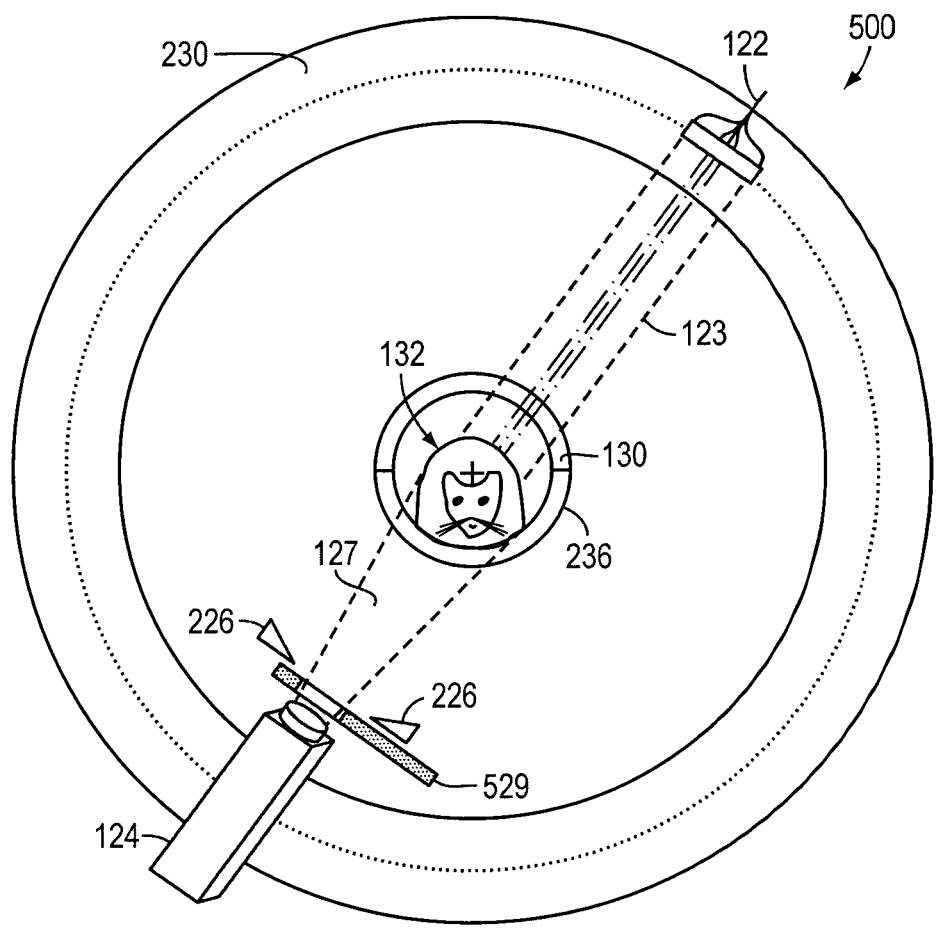
(a)
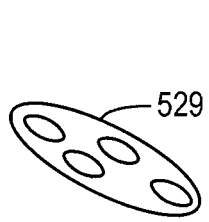
(b)
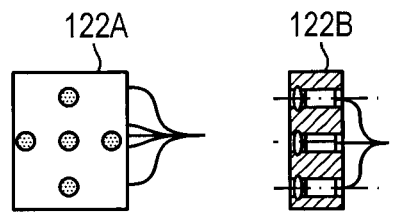
(c)
FIG. 5

COMBINED X-RAY AND OPTICAL TOMOGRAPHIC IMAGING SYSTEM

PRIOR APPLICATIONS

This application claims the benefit of U.S. Provisional Patent Application No. 60/753,590, filed Dec. 22, 2005, the text of which is incorporated by reference herein in its entirety.

GOVERNMENT RIGHTS

The invention was supported, in whole or in part, by grant 1 R44 ES012699-01 from the National Institute of Environmental Health Sciences. The Government has certain rights in the invention.

FIELD OF THE INVENTION

The invention relates generally to tomographic imaging systems. More particularly, in certain embodiments, the invention relates to a combined x-ray and optical tomographic imaging system.

BACKGROUND OF THE INVENTION

Tomography allows construction of detailed images of internal structures of objects. Tomography relies upon a selected form of energy being directed toward and passing through the object at more than one angle. The energy from the various angles is detected and corresponding data processed to provide a tomographic image. The received signals are typically less intense (e.g., darker) where the object is thicker or more dense, and more intense (e.g., brighter) where the object is thinner or less dense.

A signal received by a single energy sensor (e.g., at one angle) does not contain sufficient information to generate either a two-dimensional or a three-dimensional representation of internal structures of the object. Signals received by energy sensors arranged in a plane or volume provide sufficient information to generate a three-dimensional representation of internal structures of the object.

Tomography may be used in a variety of imaging systems with different types of transmitted and received electromagnetic radiation. In particular, in x-ray Computed Axial Tomography (CAT), x-ray radiation is projected through an object, typically at a variety of angles, and a variety of x-ray receivers, at a corresponding variety of angles, are used to receive the x-rays transmitted through the object. A computer is used to generate an image of internal structures of the object in three dimensions from signals received by the variety of x-ray receivers.

X-rays tend to pass through the object in straight lines with relatively little attenuation, allowing non-invasive capture of certain anatomical features at high resolution (e.g., distinguishing features as small as 50-100 μm in one or more dimensions). X-ray CAT imaging systems can be used to image bones, organs, blood vessels, and tumors of a particular subject. While x-ray CAT imaging is able to provide high resolution of certain anatomical structures, it is relatively limited in its ability to detect, distinguish, or quantify specific chemical or biological species in the subject. Therefore, existing x-ray CAT systems cannot provide functional (or, "molecular") information about a subject or disease state at the cellular or molecular level.

Imaging techniques such as x-ray CAT, magnetic resonance imaging (MRI) and ultrasound (US) primarily rely on physical parameters such as absorption, scattering, proton density, and relaxation rates as the primary source of contrast for imaging. Specific molecular information with these modalities cannot often be obtained or is limited. Optical imaging, for example, optical tomographic imaging, uses specific molecular activity or alterations as the source of image contrast and therefore, can provide much more molecular or functional information about a subject or disease state than imaging techniques such as x-ray CAT that primarily capture anatomical information based on physical parameters.

Optical tomographic systems use one or more wavelengths of visible or invisible light, rather than x-rays. Unlike x-ray tomography, in which x-rays tend to pass through an object in a straight line with relatively little attenuation, visible and invisible (ultraviolet or infrared) light tends to be absorbed and to scatter when passing though an object. Therefore, light does not travel in straight lines when passing through the object. Light also tends to be absorbed and scattered more when passing through a relatively thick and/or non-homogeneous medium, than when passing through a relatively thin and/or homogeneous medium.

Most conventional optical tomography systems use near infrared (near-IR, NIR) light, instead of light in the visible spectrum when passing through animal tissues, since NIR tends to be absorbed less and to scatter less than visible light. The use of NIR light generally provides the ability to image deeper tissues, e.g., thicker tissues, and/or the ability to image with higher sensitivity than the use of visible light.

While optical tomography is well suited to providing molecular/functional information about a subject, the achievable resolution is not as high as with x-ray CAT or MRI. Two exemplary optical tomographic techniques are Diffuse Optical Tomography (DOT) and Fluorescence Molecular Tomography (FMT). Both DOT and FMT allow optical tomographic imaging of the internal structure of animal and/or human subjects.

DOT is an imaging technique capable of providing biological functional information by imaging hemoglobin concentration and tissue oxygenation state. DOT approaches are currently being used to detect certain types of tumors, including breast tumors.

Unlike most DOT approaches, FMT uses fluorescent molecular probes, which absorb light propagating inside of an object and emit light at a longer wavelength (lower energy) than the absorbed light inside of the object, allowing non-invasive, in vivo investigation of functional and molecular signatures in whole tissues of animals and humans. FMT systems enable molecular imaging, for example, FMT can be used to visually indicate molecular abnormalities that are the basis of a disease, rather than just imaging the anatomical structures in the area of suspected molecular abnormalities, as with conventional imaging approaches. Specific imaging of molecular targets provides earlier detection and characterization of a disease, as well as earlier and direct molecular assessment of treatment efficacy. An illustrative FMT system is described in U.S. Patent Application Publication No. US2004/0015062, the text of which is incorporated by reference herein, in its entirety.

Most existing DOT and FMT systems use light sources and light sensors in direct contact with the object to be imaged and/or use optical matching fluid. For both DOT and FMT systems, the use of fiber guides and/or optical matching fluids limits the tomographic capacity of such systems and impedes their practicality in research and/or clinical settings.

Recent improvements in fluorescence molecular tomography have led to the development of more versatile imaging techniques that do not require either direct contact or optical contact between the light sources/detectors and the object to be imaged. These techniques employ more powerful algorithms that account for heterogeneities of the index of refraction within and surrounding the animal tissue which give rise to photon reflections at the boundaries. See, for example, International (PCT) Application Publication No. WO 03/102558, published 11 Dec. 2003; and R. Schulz, J. Ripoll and V. Ntziachristos, "Experimental Fluorescence Tomography of Tissues with Noncontact Measurements," IEEE Transactions on Medical Imaging, Vol. 23, No. 4, pp. 492-500 (2004), the texts of which are incorporated herein by reference, in their entirety. These techniques are further augmented by the use of so-called free-space transformations, which take into account the presence of a non-turbid medium (air) between the object to be imaged and the detectors. See, for example, International (PCT) Application Publication No. WO 2004/072906, published 26 Aug. 2004; and J. Ripoll, R. Schulz and V. Ntziachristos, "Free-Space Propagation of Diffuse Light: Theory and Experiments," Physical Review Letters, Vol. 91 No. 10 (2003), the texts of which are incorporated herein by reference, in their entirety.

Recent work in clinical and pre-clinical imaging has applied computed tomography in nuclear imaging approaches. For example, there are several research prototypes as well as a few commercially available imaging systems combining Positron Emission Tomography (PET) with Computed Tomography (CT), now referred to as PET/CT systems. Similarly, there are systems combining Single Photon Emission Computed Tomography (SPECT) with Computed Tomography (CT), or SPECT/CT systems. These systems provide improved photon detection capability, thereby enabling greater image resolution.

However, PET/CT and SPECT/CT systems are nuclear imaging approaches with various complexities and limitations associated therewith, including, for example, the high cost (both capital and operation/maintenance costs) of the nuclear imaging equipment, the required injection of a radioactive tracer isotope into the subject, and the long waiting period (e.g., an hour or more) required for concentration of the tracer in the tissues before imaging can begin. Furthermore, where a PET (or SPECT) scan and a CT scan are taken one after the other, the subject must remain motionless between scans to avoid co-registration problems, and there may nevertheless be error caused by involuntary patient motion (e.g., due to breathing) between subsequent scans.

There is a need for a tomographic imaging system for providing more accurate biological functional information than current light-based DOT and FMT systems. There is also a need for a tomographic imaging system that provides biological functional information within an anatomical context. Non-light-based, nuclear tomographic imaging systems, such as combined PET/CT and SPECT/CT systems, can be used to provide some functional information, but they are expensive, require administration of radiopharmaceuticals prior to imaging, and have other drawbacks associated with nuclear imaging systems.

SUMMARY OF THE INVENTION

The invention provides a combined x-ray and optical (light-based) tomographic imaging system that yields more accurate functional information than can be achieved by optical tomography alone. The system is configured with one or more x-ray sources, x-ray detectors, light sources, and light detectors operatively arranged to rotate (for example, on a gantry) about an imaging chamber containing the object to be imaged. Data corresponding to both the detected x-ray radiation and the detected light are used to create a tomographic image that provides functional and/or molecular information. Further advantage is achieved by overlaying or co-registering this tomographic image with a detailed anatomical dataset, e.g., from the x-ray tomographic subsystem, to form a composite tomographic image displaying functional/molecular information in relation to anatomical features of the subject.

A synergistic benefit is obtained from the configuration of the system, as well as the way both optical data and x-ray data are processed. For example, at a given gantry location, x-ray radiation and light may be directed into the subject simultaneously, or alternately in quick succession. This allows substantially simultaneous acquisition of x-ray and light signals, thereby reducing error caused by subject movement and improving accuracy of data and/or image co-registration.

Preferred systems of the invention go beyond co-registration of images obtained from two or more imaging techniques. High resolution anatomical information obtained from x-ray data is used to provide a more detailed description of the optical properties of the object being imaged. For example, tissues of various densities can be distinguished by the x-ray tomographic subsystem and an optical absorption map can be produced. The optical absorption map is then used in the optical tomographic reconstruction, thereby improving how propagation of light through the object is modeled. In this way, both x-ray data and light data are used together in the optical tomographic reconstruction to create the tomographic image, thereby allowing a more accurate tomographic reconstruction result.

In addition, the functional and/or molecular information provided by the optical tomographic image (created with the aid of x-ray data) can be combined with the x-ray tomographic dataset to provide a composite image containing both functional/molecular information as well as high resolution anatomical information. The additional anatomical information may significantly enhance interpretation of functional/molecular imaging results.

A further synergistic benefit is realized by the arrangement of x-ray and light source-detector pairs about the imaging chamber. The arrangement allows the substantially simultaneous acquisition of x-ray radiation and light from the object. Both x-ray and light source-detector pairs are mounted to a rotating gantry and, at each gantry position, x-ray radiation is detected alternately and regularly (e.g., in an interleaved fashion) with light from the object. The light from the object includes the fluorescent light from the fluorophore(s) within the object and/or the excitation light that has been transmitted through the object.

In order to construct a tomographic image, light beams must be directed into the object at multiple positions (e.g., at multiple angles), generally one beam at a time. By interleaving the collection of x-ray radiation and light from the object in this way, only one rotation (360°) of the gantry would be needed for a full range of angles, where two full rotations (720°) of the gantry would be needed if the x-ray and light scans are performed subsequently. By reducing the mechanical movement needed to obtain sufficient tomographic data, less time is needed to obtain a scan. Not only does reducing the scan time improve efficiency, it improves accuracy in that there is less subject movement which must be accounted for (including involuntary movement, e.g., movement due to breathing) in a shorter scan than a longer scan.

The setup lends itself to additional efficiencies in the tomographic imaging. For example, the setup allows fine scanning of a light head at each gantry location to increase the amount of data obtained at a given gantry position and reduce the amount of mechanical movement needed (e.g., fewer gantry positions are needed per scan), as well as passive splitting of a single beam from the light source into multiple beams for detection.

Systems of the invention offer advantages over nuclear tomographic imaging systems such as combined PET/CT and SPECT/CT systems. The combination of optical tomography with x-ray tomography in the systems presented herein enables use of a wide array of available optical markers and/or fluorescent probes, including activatible molecular optical probes, which can be targeted to a number of important biological processes. Furthermore, unlike nuclear tomographic systems, the use of optical tomography to measure molecular activity does not involve the administration and detection of decaying radioactive compounds in vivo, the latter presenting substantial hazard to the subject and limiting the ability to perform repeat or longitudinal imaging. Optical fluorophores and fluorescent probes have longer-term stability (on the order of days, weeks, months, or years) than available radioisotopes used in PET or SPECT imaging, the half-life of which is measured in minutes or hours, thus simplifying many of the logistical challenges associated with nuclear imaging. Moreover, optical imaging is inherently a simpler and less expensive modality than either PET or SPECT imaging, and therefore more suitable for widespread adoption especially in decentralized facilities and research settings.

Systems of the invention also feature recent improvements in fluorescence molecular tomography algorithms that obviate the requirement of (i) direct contact between the light sources/detectors and the object to be imaged, and (ii) an index-matching fluid between the imaging chamber wall and the object to be imaged. Embodiments of the invention are particularly amenable to application of non-contact and free-space tomographic techniques because of the kinds of data that are collected. For example, in certain embodiments, a three-dimensional surface model of the object is created using data corresponding to the collected x-ray radiation, the collected light, or both. The surface model provides one or more boundary conditions, which are then used along with optical data in the free-space optical tomographic reconstruction to create the tomographic image.

In accordance with embodiments of the present invention, an imaging system and methods are described to acquire high resolution anatomical and molecular/functional representations (e.g., composite tomographic images) of human and/or animal subjects, including human patients, within a single imaging system (e.g., combined imaging system). It is an object of the invention to provide such combined imaging systems and composite tomographic images for use in biological research, as well as in preclinical and/or clinical settings. In particular, the present invention provides combined imaging systems that can optionally be used with one or more imaging agents for in vivo molecular imaging.

In one aspect, the invention relates to a system for creating one or more tomographic images of a target volume of an object, the system including an x-ray source configured to direct x-ray radiation into the object; an x-ray detector configured to detect x-ray radiation transmitted through the object; a light source configured to direct light into the object; a light detector configured to detect light transmitted through and/or emitted from the object, wherein the x-ray source, the x-ray detector, the light source, and the light detector are disposed about an imaging chamber into which the object is placed for analysis; a memory for storing code that defines a set of instructions; and a processor for executing the set of instructions to create one or more tomographic images of the target volume of the object, wherein at least one of the tomographic images is based at least in part on the detected x-ray radiation and the detected light. The object may be, for example, an animal, for example, a mammal, or a human.

In certain embodiments, the tomographic image is a composite of an optical tomographic image (in which x-ray data may or may not have been used in the optical tomographic reconstruction) and an x-ray tomographic image. In certain embodiments, the tomographic image is an optical tomographic image in which x-ray data is used along with optical data in an optical tomographic reconstruction (and which is not necessarily a composite of an optical tomographic image and an x-ray tomographic image). In certain embodiments, the tomographic image is an optical tomographic image in which x-ray data is used along with optical data in an optical tomographic reconstruction and which is a composite of an optical tomographic image and an x-ray tomographic image.

In certain embodiments, the x-ray source, the x-ray detector, the light source, and the light detector are radially disposed about the imaging chamber. There may be a plurality of x-ray sources, x-ray detectors, light sources, and/or light detectors. The x-ray source, x-ray detector, light source, and light detector may be mounted on a gantry that is rotatable about the imaging chamber.

The light source may be configured to direct excitation light into the object at multiple locations and/or the x-ray source may be configured to direct x-ray radiation into the object at multiple locations by operation of one or more of the following: by rotation of the gantry about the imaging chamber; by fine scanning of a light head of the light source at one or more gantry locations; and/or by passive splitting of a single beam from the light source into multiple beams.

In certain embodiments, the x-ray source is configured to direct x-ray radiation into the object at multiple locations. The code may comprise instructions to create a three-dimensional optical absorption map of the target volume based at least in part on the detected x-ray radiation and to use the optical absorption map in optical tomographic reconstruction to create an optical tomographic image. For example, the three-dimensional optical absorption map may be a collection of absorption coefficients corresponding to a plurality of segmented regions of the target volume.

The system may feature a subsystem for creation of a surface model to be used in the optical tomographic reconstruction. For example, the code may include instructions to create a surface model of at least a portion of the object based at least in part on the detected x-ray radiation and to use the surface model in optical tomographic reconstruction to create an optical tomographic image. The surface model may provide one or more boundary conditions used in the optical tomographic reconstruction.

Alternately, the surface model may be based at least in part on optical data instead of (or in addition to) x-ray data. For example, the system may include a coordinate light source and sensor configured to map at least a portion of a three-dimensional surface of the object. The code may then include instructions to use the surface model in optical tomographic reconstruction, for example, by providing one or more boundary conditions.

The code may include instructions to use detected x-ray radiation to create an x-ray tomographic image (e.g., a three-dimensional anatomical dataset), which can be registered with the tomographic image to create a composite (e.g., combined) image.

In preferred embodiments, the light source is configured to direct excitation light into the object at multiple locations. The excitation light may have wavelength within a range, for example, from 550 nm to 1300 nm; from 575 nm to 1200 nm; from 600 nm to 1100 nm; from 625 nm to 1000 nm; or from 650 nm to 900 nm. The excitation light may include continuous wave light, time resolved light, and/or intensity modulated light. The detected light preferably includes excitation light from the light source that has been transmitted through the object and fluorescent light emitted from one or more fluorophores within the object. Data corresponding to the excitation light transmitted through the object, or intrinsic light, can be used to correct/calibrate captured fluorescent measurements, thereby providing more accurate tomographic images. The one or more fluorophores emit fluorescent light as a result of excitation by the excitation light. Background fluorescence may be accounted for by obtaining background measurements and processing data corresponding to the captured fluorescent light accordingly.

The one or more fluorophores may include an endogenous fluorophore and/or an exogenous (administered/delivered) probe. The one or more fluorophores may include one or more examples of one or more of the following: a molecular probe, an activatable probe, an enzyme-activatable probe, a quantum dot-based imaging probe, a nanoparticle-based imaging probe, a probe targeted to a biomolecule, a wavelength shifting beacon, a multicolor fluorescent probe, a probe with high binding affinity to a target, a non-specific imaging probe, labeled cells (e.g., genetically encoded fluorescent or bioluminescent cells), x-ray contrast agent, magnetic resonance contrast agent, a dual modality agent, an optical/CT dual modality agent (e.g., an optical agent physically or chemically bound to a CT agent), an optical/MR dual modality agent (e.g., an optical agent physically or chemically bound to an MR agent), a lanthanide metal-ligand probe, and/or any combination thereof. The one or more fluorophores may include a probe targeted to a biomarker, a molecular structure, a mineral (e.g., hydroxyapatite), and/or a biomolecule. Where the probe is targeted to a biomolecule, the biomolecule may include one or more examples of one or more of the following: a cell type, an antibody, a protein, a glycoprotein, a cell receptor, a neurotransmitter, an integrin, a growth factor, a cytokine, a lymphokine, a lectin, a selectin, a toxin, a carbohydrate, an internalizing receptor, an enzyme, a protease, a virus, a bacteria, a microorganism, and/or any combination thereof. It is preferred that the code includes instructions to process data corresponding to both the detected excitation light transmitted through the object and the detected fluorescent light emitted from the one or more fluorophores within the object to create the tomographic image of the target volume.

The system may include a plurality of x-ray sources configured to direct x-ray radiation into the object and corresponding x-ray detectors configured to detect x-ray radiation transmitted through the object (e.g., x-ray source-detector pairs), the x-ray sources and x-ray detectors disposed about the imaging chamber. In certain embodiments, the plurality of x-ray sources have different beam energies allowing discrimination/contrast between soft and hard tissue.

In certain embodiments, the system includes a display for viewing the tomographic image. In certain embodiments, the light detector is or includes a CCD camera and/or a time-gated intensified CCD camera (e.g., an iCCD camera).

The optical subsystem (e.g., made up of the light source, light detector, and associated electronics) of the combined x-ray/optical tomography system may be a "contact" or a "non-contact" optical system. Non-contact systems are preferred because they do not require either direct (e.g. physical) contact or optical contact between the light detector and the object to be imaged, and non-contact systems do not require direct contact or optical contact between the light source and the object to be imaged. An example of optical contact would include use of an index-matching medium between the sensor and the surface of the object being imaged. Non-contact systems do not require use of an index-matching medium. An optical system is considered herein to be a contact system when a receiving portion of the light detector (and/or an emitting portion of the light source) nearest to the surface of the object being imaged is in contact with the surface of the object or the surface of the index matching medium, or is no more than about 1 mm from the surface of the object or the surface of the index matching medium. In certain embodiments featuring a contact optical subsystem, the receiving portion of the light detector (and/or an emitting portion of the light source) is less than about 0.5 mm, less than about 0.3 mm, less than about 0.2 mm, or less than about 0.1 mm from the surface of the object or the surface of the index matching medium.

It is preferred that the optical subsystem of the combined x-ray/optical tomographic system be a non-contact optical system. An optical system is considered herein to be a non-contact system where a receiving portion of the light detector (and/or an emitting portion of the light source) nearest to the surface of the object being imaged is greater than about 1 mm from the surface of the object (or the surface of an index matching medium). In certain embodiments featuring a non-contact optical subsystem, the receiving portion of the light detector (and/or an emitting portion of the light source) nearest to the surface of the object being imaged (or the surface of an index matching medium) is greater than about 2 mm, greater than about 3 mm, greater than about 5 mm, greater than about 7 mm, greater than about 9 mm, greater than about 1 cm, greater than about 2 cm, greater than about 3 cm, greater than about 4 cm, or greater than about 5 cm from the surface of the object.

The optical subsystem (e.g., made up of the light source, light detector, and associated electronics) of the combined x-ray/optical tomography system may be a free-space optical system. Free-space optical subsystems do not require the presence of an index-matching fluid between the imaging chamber wall and the object to be imaged. In free-space systems, a non-turbid medium such as air is located between the receiving portion of the light detector (and/or the emitting portion of the light source) and the surface of the object. In certain embodiments—for example, in embodiments in which free space algorithms are not used in the optical tomographic reconstruction—an index-matching fluid is located between the receiving portion of the light detector (and or the emitting portion of the light source) and the surface of the object.

In another aspect, the invention relates to a method of imaging a target volume of an object, the method including the steps of directing x-ray radiation into the object at multiple locations; detecting x-ray radiation transmitted through the object; directing excitation light into the object at multiple locations; detecting excitation light transmitted through the object; detecting fluorescent light emitted from one or more fluorophores within the object; and processing data corresponding to the detected x-ray radiation transmitted through the object, the detected excitation light transmitted through the object, and the detected fluorescent light emitted from the one or more fluorophores within the object to provide one or more tomographic images of the target volume of the object. The method may further include the step of displaying the tomographic image. The object may be, for example, an animal, for example, a mammal, or a human. The description of embodiments in the preceding paragraphs can be applied to this aspect of the invention, as well.

In certain embodiments, the detected fluorescent light from the one or more fluorophores was emitted as a result of excitation by the excitation light. The excitation light may have a peak wavelength within a range, for example, from 550 nm to 1300 nm; from 575 nm to 1200 nm; from 600 nm to 1100 nm; from 625 nm to 1000 nm; or from 650 nm to 900 nm. The excitation light may include continuous wave light, time resolved light, and/or intensity modulated light. The excitation light may include laser light. Preferably, the excitation light includes narrow-bandwidth light. The excitation light may include light of two or more peak wavelengths corresponding to excitation wavelengths of different fluorophores (e.g., administered, fluorescent molecular probes) within the object. The peak wavelength of the fluorescent light emitted following excitation by the excitation light may be from about 10 to about 50 nm longer than the peak wavelength of the excitation light, from about 15 to about 40 nm longer than the peak wavelength of the excitation light, or from about 20 to about 30 nm longer than the peak wavelength of the excitation light. Preferably, the peak wavelength of the detected fluorescent light is different than the peak wavelength of the excitation light, for example, to facilitate discrimination between excitation and emission light. The one or more fluorophores may include a plurality of probes administered to the object, each probe having corresponding peak excitation and emission wavelengths. The step of directing excitation light into the object may include directing narrow bandwidth excitation light into the object at multiple locations.

The detected light preferably includes excitation light from the light source that has been transmitted through the object and fluorescent light emitted from one or more fluorophores within the object. Data corresponding to the excitation light transmitted through the object, or intrinsic light, can be used to correct/calibrate captured fluorescent measurements, thereby providing more accurate tomographic images. The one or more fluorophores emit fluorescent light as a result of excitation by the excitation light. Background fluorescence may be accounted for by obtaining background measurements and processing data corresponding to the captured fluorescent light accordingly. For example, the method may include the step of detecting a background signal, where the processing step includes generating a corrected measurement of the detected fluorescent light and/or a corrected measurement of the detected excitation light using data corresponding to the detected background signal, and using the corrected measurement(s) in the optical tomographic reconstruction. In certain embodiments, the processing step includes generating a corrected measurement of the detected fluorescent light and a corrected measurement of the detected excitation light using data corresponding to the detected background light, generating a calibrated fluorescent measurement from the corrected fluorescent measurement and the corrected excitation light measurement, and using the calibrated fluorescent measurement in the optical tomographic reconstruction.

The one or more fluorophores may include an endogenous fluororphore and/or an exogenous (administered/delivered) fluorophore. The one or more fluorophores may include one or more examples of one or more of the following: a molecular probe, an activatable probe, an enzyme-activatable probe, a quantum dot-based imaging probe, a nanoparticle-based imaging probe, a probe targeted to a biomolecule, a wavelength shifting beacon, a multicolor probe, a probe with high binding affinity to a target, a non-specific imaging probe, labeled cells (e.g., genetically encoded fluorescent or bioluminescent cells), x-ray contrast agent, magnetic resonance contrast agent, a dual modality agent, an optical/CT dual modality agent (e.g., an optical agent physically or chemically bound to a CT agent), an optical/MR dual modality agent (e.g., an optical agent physically or chemically bound to an MR agent), a lanthanide metal-ligand probe, and/or any combination thereof. The one or more fluorophores may include a probe targeted to a biomarker, a molecular structure, a mineral (e.g., hydroxyapatite), and/or a biomolecule. Where the probe is targeted to a biomolecule, the biomolecule may include one or more examples of one or more of the following: a cell type, an antibody, a protein, a glycoprotein, a cell receptor, a neurotransmitter, an integrin, a growth factor, a cytokine, a lymphokine, a lectin, a selectin, a toxin, a carbohydrate, an internalizing receptor, an enzyme, a protease, a virus, a bacteria, a microorganism, and/or any combination thereof.

In certain embodiments, the x-ray radiation, the excitation light, and the fluorescent light are detected substantially simultaneously. In certain embodiments, the x-ray radiation is detected alternately and regularly with the excitation light and/or the fluorescent light (e.g., in an interleaved fashion from one gantry position to the next, with alternating x-ray radiation detection and light detection).

The processing step may include simulating photon propagation at the excitation wavelength and simulating photon propagation at the emission wavelength in an optical tomographic reconstruction.

Data corresponding to the detected light may be used as input in the optical tomographic reconstruction, for example, in an iterative process. The processing step may further include processing data corresponding to the detected x-ray radiation to create a three-dimensional optical absorption map in the target volume and using the optical absorption map in the optical tomographic reconstruction. The optical absorption map may include absorption coefficients corresponding to a plurality of segmented regions of the target volume. The regions may be segmented based at least in part on the detected x-ray radiation.

Data corresponding to the detected x-ray radiation may be used to create a surface model of at least a portion of the object, and the surface model used in the optical tomographic reconstruction. The surface model may provide one or more boundary conditions used in the optical tomographic reconstruction.

The processing step may further include creating an anatomical dataset (e.g., a three-dimensional x-ray tomographic image) using the detected x-ray radiation and registering the anatomical dataset with the optical tomographic image to create a composite or combined image. The tomographic image(s) may visually indicate a spatial distribution of a quantity (e.g., concentration) of at least one of the one or more fluorophores within the target volume of the object.

The method may further include the step of using the tomographic image(s) (either separately or in combination)

to perform one or more of the following: identifying an area of disease; distinguishing between diseased and normal tissue; localizing diseased tissue; detecting a boundary of a lesion; detecting a tumor; locating a boundary of a tumor; localizing a cell type; and/or characterizing a disease. Where the method includes the step of using one or more of the tomographic images to identify an area of disease, the disease may include at least one or more examples of one or more of the following: inflammation, cancer, cardiovascular disease, dermatologic disease, ophthalmic disease, infectious disease, immunologic disease, central nervous system disease, inherited disease, metabolic disease, environmental disease, and/or bone-related disease.

In certain embodiments, the steps of the method are repeated to obtain a plurality of tomographic images. The method is conducive to obtaining a plurality of images, for example, because radiopharmaceuticals do not need to be used and radiotoxicity is not a concern, unlike in nuclear tomographic systems.

For example, in certain embodiments, the plurality of tomographic images are obtained as a function of time following administration of one or more probes including at least one of the one or more fluorophores. The plurality of tomographic images may be used, for example, to monitor localization of a cell type, monitor expression of a gene, monitor progression of a disease, and/or monitor a therapeutic response, for example, in drug development.

The step of monitoring localization of a cell type may include one or more examples of one or more of the following cell types: T-cells, tumor cells, immune cells, stem cells, and/or any combination thereof. The method may include the step of monitoring expression of a gene, where the gene encodes a fluorescent protein detected as one of the one or more fluorophores within the object. The step of monitoring therapeutic response may include performing one or more of the following using a plurality of tomographic images: determining efficacy of an administered pharmacological substance; customizing dosage of a pharmacological substance; formulating a pharmacological substance; customizing a formulation of a pharmacological substance; determining pharmacokinetic parameters of a pharmacological substance; and/or customizing a combination of pharmacological substances for the treatment of a disease.

In yet another aspect, the invention relates to a method of imaging a target volume of an object, the method including the steps of directing x-ray radiation into the object at multiple locations; detecting x-ray radiation transmitted through the object; directing light into the object at multiple locations; detecting light transmitted through and/or emitted from the object; and processing data corresponding to both the detected x-ray radiation and the detected light in an optical tomographic reconstruction to provide an optical tomographic image of the target volume of the object. The description of embodiments in the preceding paragraphs can be applied to this aspect of the invention, as well.

In certain embodiments, the processing step includes processing data corresponding to the detected x-ray radiation to create a three-dimensional optical absorption map in the target volume and using the optical absorption map in the optical tomographic reconstruction. The optical absorption map may include absorption coefficients corresponding to a plurality of segmented regions of the target volume. The processing step may further include processing data corresponding to the detected x-ray radiation and/or the detected light to create a surface model of at least a portion of the object and using the surface model in the optical tomographic reconstruction, for example, where the surface model provides one or more boundary conditions used in the optical tomographic reconstruction.

In certain embodiments, the processing step includes creating a three-dimensional anatomical dataset (e.g., a three-dimensional x-ray tomographic image containing anatomical information) using the detected x-ray radiation and combining, compositing, and/or displaying the anatomical dataset with the optical tomographic image. In certain embodiments, the processing step includes processing data corresponding to the detected x-ray radiation to create a three-dimensional optical absorption map in the target volume and a surface model of at least a portion of the object and using the optical absorption map and the surface model in the optical tomographic reconstruction. The method may further include creating a three-dimensional anatomical dataset (e.g., an x-ray tomographic image) using the detected x-ray radiation and registering the anatomical dataset with the optical tomographic image to create a composite or combined image.

BRIEF DESCRIPTION OF DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

FIG. 5 is a schematic diagram of the optical axis of a combined x-ray/optical tomographic imaging system, showing a multi-position scan head and multi-position fluorescence and excitation filter wheel, according to an illustrative embodiment of the invention.

DETAILED DESCRIPTION

Figure 1:
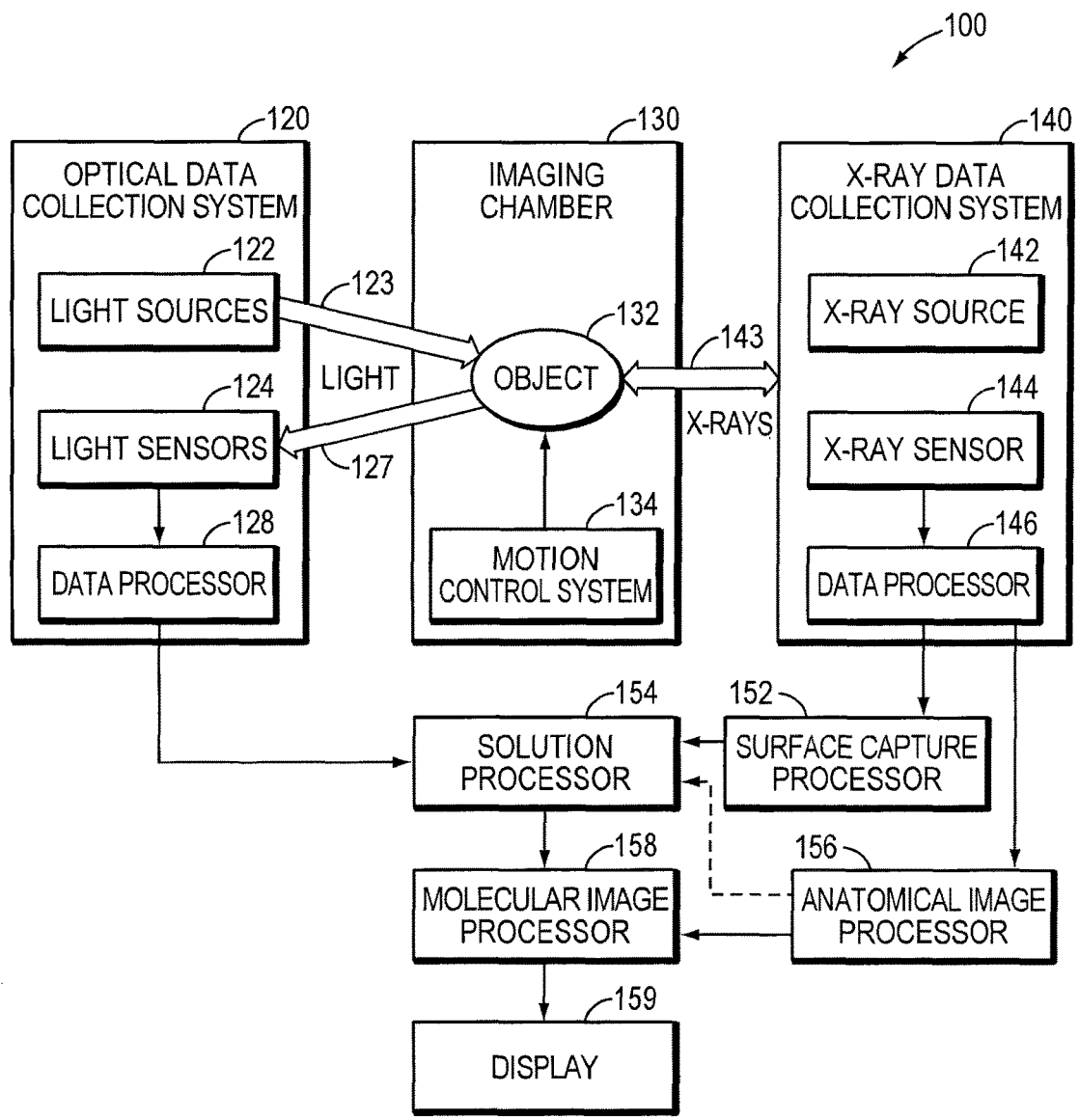
FIG. 1 is a block diagram of a combined x-ray and optical tomographic system, according to an illustrative embodiment of the invention.

It is contemplated that methods, systems, and processes described herein encompass variations and adaptations developed using information from the embodiments described herein.

Throughout the description, where systems and compositions are described as having, including, or comprising specific components, or where processes and methods are described as having, including, or comprising specific steps, it is contemplated that, additionally, there are systems and compositions of the present invention that consist essentially of, or consist of, the recited components, and that there are processes and methods of the present invention that consist essentially of, or consist of, the recited processing steps.

The mention herein of any publication, for example, in the Background section, is not an admission that the publication serves as prior art with respect to any of the claims presented herein. The Background section is presented for purposes of clarity and is not meant as a description of prior art with respect to any claim.

Headers are used herein to aid the reader and are not meant to limit the interpretation of the subject matter described.

As used herein, the term "image" is understood to mean a visual display or any data representation that may be interpreted for visual display. For example, a three-dimensional image may include a dataset of values of a given quantity that varies in three spatial dimensions. A three-dimensional image (e.g., a three-dimensional data representation) may be displayed in two-dimensions (e.g., on a two-dimensional screen, or on a two-dimensional printout). The term "tomographic image" may refer, for example, to an optical tomographic image, an x-ray tomographic image, an optical tomographic image created using x-ray data in the optical tomographic reconstruction, an x-ray tomographic image created using optical data in the x-ray tomographic reconstruction, a composite of an optical tomographic image and an x-ray tomographic image, and/or a combination of an optical tomographic image with an x-ray tomographic image.

As used herein, the term "map" is understood to mean a visual display, or any data representation that may be interpreted for visual display, which contains spatially-correlated information. For example, a three-dimensional map of a given volume may include a dataset of values of a given quantity that varies in three spatial dimensions throughout the volume, and the three-dimensional map may be displayed in two-dimensions.

Optical tomographic systems require construction of a model of light propagation through the object being imaged. Such models generally invoke assumptions of an average optical absorption coefficient and an average optical scattering coefficient for the object being imaged at the wavelengths of imaging, either measured or known a priori. These average values are provided to the optical models either directly or indirectly as part of a diffusion coefficient expression.

A benefit of the present invention stems from the use of x-ray tomography in the combined x-ray/optical tomography system, which results, for example, in the following three performance enhancements: (1) the x-ray tomographic system measurement and reconstruction generates a three-dimensional map of attenuation which can be related to a corresponding three-dimensional map of optical absorption; (this three-dimensional map of optical absorption provides a far more accurate and finer-grained input to the optical tomography algorithm); (2) the x-ray tomographic system measurement and reconstruction also generates a three-dimensional surface model of the object, which provides the optical tomography algorithm with the boundary conditions necessary for its computation; (3) the x-ray tomographic system reconstruction provides a three-dimensional high-resolution anatomical reference dataset, on which can be overlaid the optical tomography reconstruction.

FIG. 1 is a block diagram 100 of a combined x-ray and optical tomographic system, according to an illustrative embodiment of the invention. The combined tomography system 100 includes an optical data collection system 120, a subject imaging chamber 130, and an x-ray data collection system 140. The optical data collection system 120 has one or more light sources 122 spaced from an object 132 under study or examination. Each of the one or more light sources 122 projects light 123 toward the object 132. Portions 127 of the light 123 which pass through the object 132 are received by one or more light sensors 124 which are disposed proximate to, but spaced apart from, the object 132 (in non-contact embodiments). The sensors 124 are disposed about the object 132 such that the sensors 124 can receive light, which propagates through the object 132. Since the one or more light sensors 124 are spaced apart from the object, the light propagates in free space prior to reaching the sensors 124. The separation between the object 132 and the light sensors 124 and the separation between the object 132 and the light sources 122 are selected in accordance with a variety of factors including, for example, a distance that can achieve a proper focal depth while maximizing light collection capacity. For example, the separation between the surface of the object 132 and the end(s) of the light sensor(s) (detectors) 124 nearest the surface of the object may be about 1 mm, about 2 mm, about 3 mm, about 5 mm, about 7 mm, about 1 cm, about 2 cm, about 3 cm, about 5 cm, about 10 cm, about 15 cm, about 20 cm, about 25 cm, greater than about 1 mm, greater than about 2 mm, greater than about 3 mm, greater than about 5 mm, greater than about 7 mm, greater than about 1 cm, greater than about 2 cm, greater than about 3 cm, greater than about 5 cm, greater than about 10 cm, greater than about 15 cm, greater than about 20 cm, or greater than about 25 cm. The separation between the surface of the object 132 and the end(s) of the light source(s) 124 nearest the surface of the object may be about 1 mm, about 2 mm, about 3 mm, about 5 mm, about 7 mm, about 1 cm, about 2 cm, about 3 cm, about 5 cm, about 10 cm, about 15 cm, about 20 cm, about 25 cm, greater than about 1 mm, greater than about 2 mm, greater than about 3 mm, greater than about 5 mm, greater than about 7 mm, greater than about 1 cm, greater than about 2 cm, greater than about 3 cm, greater than about 5 cm, greater than about 10 cm, greater than about 15 cm, greater than about 20 cm, or greater than about 25 cm, for example.

The one or more light sensors 124 provide corresponding light sensor signals (e.g. in the form of electrical or other types of signals) to a data processor 128. The data processor 128 digitizes, formats, and combines the digitized and formatted light sensor signals into vectors (or other data format) for subsequent processing.

In certain embodiments, the light sensors 124 are also adapted to receive fluorescent light generated by fluorophores internal to the object 132, for example, from optical probes, including targeted or molecular optical probes injected (or otherwise administered) into the object 132 which tend to coalesce in particular structures or molecules within the object 132.

The optical data collection system 120 is coupled to a solution processor 154 and, in an exemplary embodiment (FIG. 1), the optical data collection system 120 provides measured optical data to the solution processor 154 through the data processor 128. The solution processor 154 provides a solution to an "image problem" in the form of image data corresponding to internal structures in the object 132. The solution procedure performed by the solution processor 154 is described in more detail below, and uses optical tomographic techniques described in International (PCT) Patent Application Publication Nos. WO2003/102558 and WO2004/072906, which are incorporated by reference herein, in their entirety.

Figure 2:
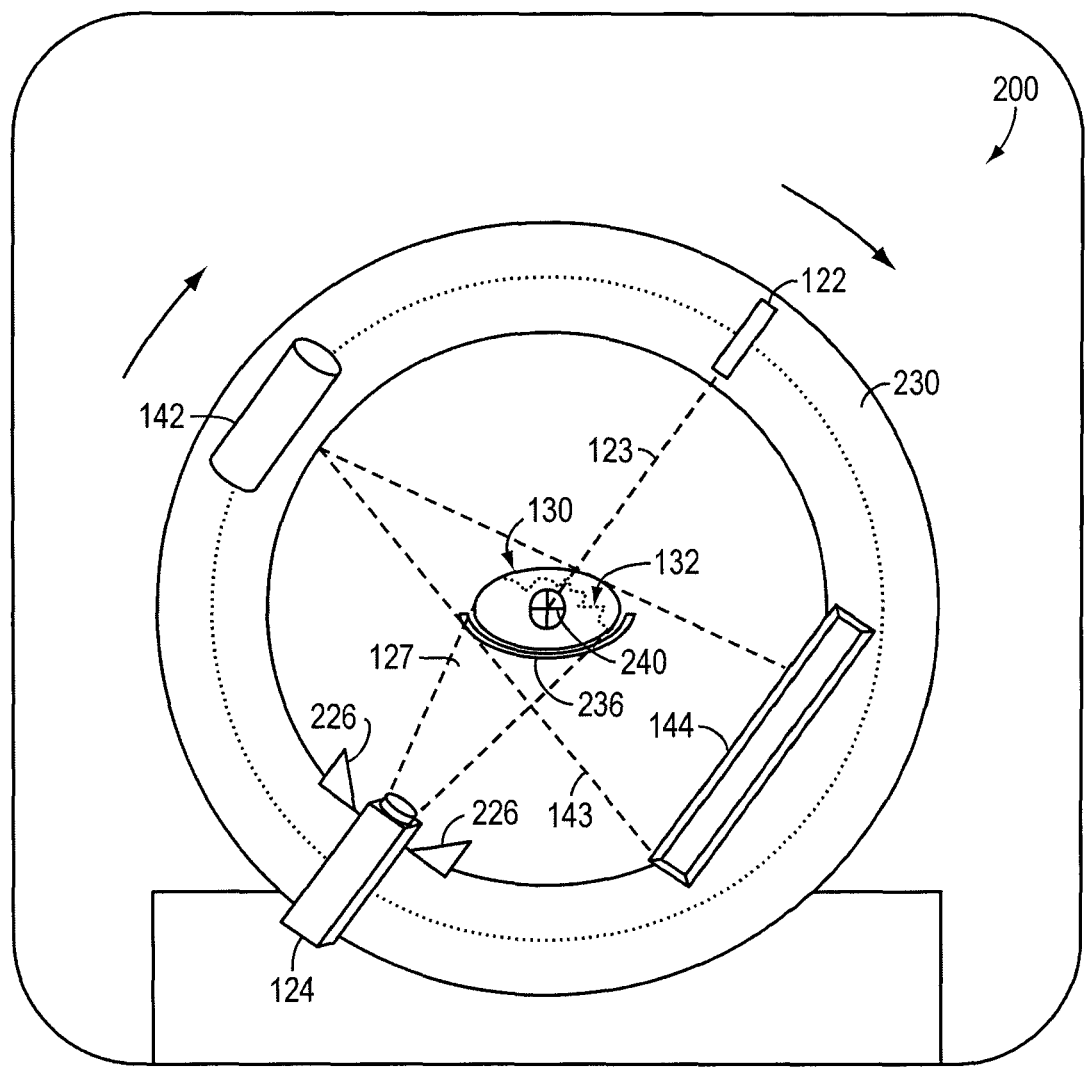
FIG. 2 is a schematic diagram of a combined x-ray and optical tomographic system with x-ray and optical components mounted on a gantry that rotates about an imaging chamber in which the subject is placed, according to an illustrative embodiment of the invention.
Figure 3:
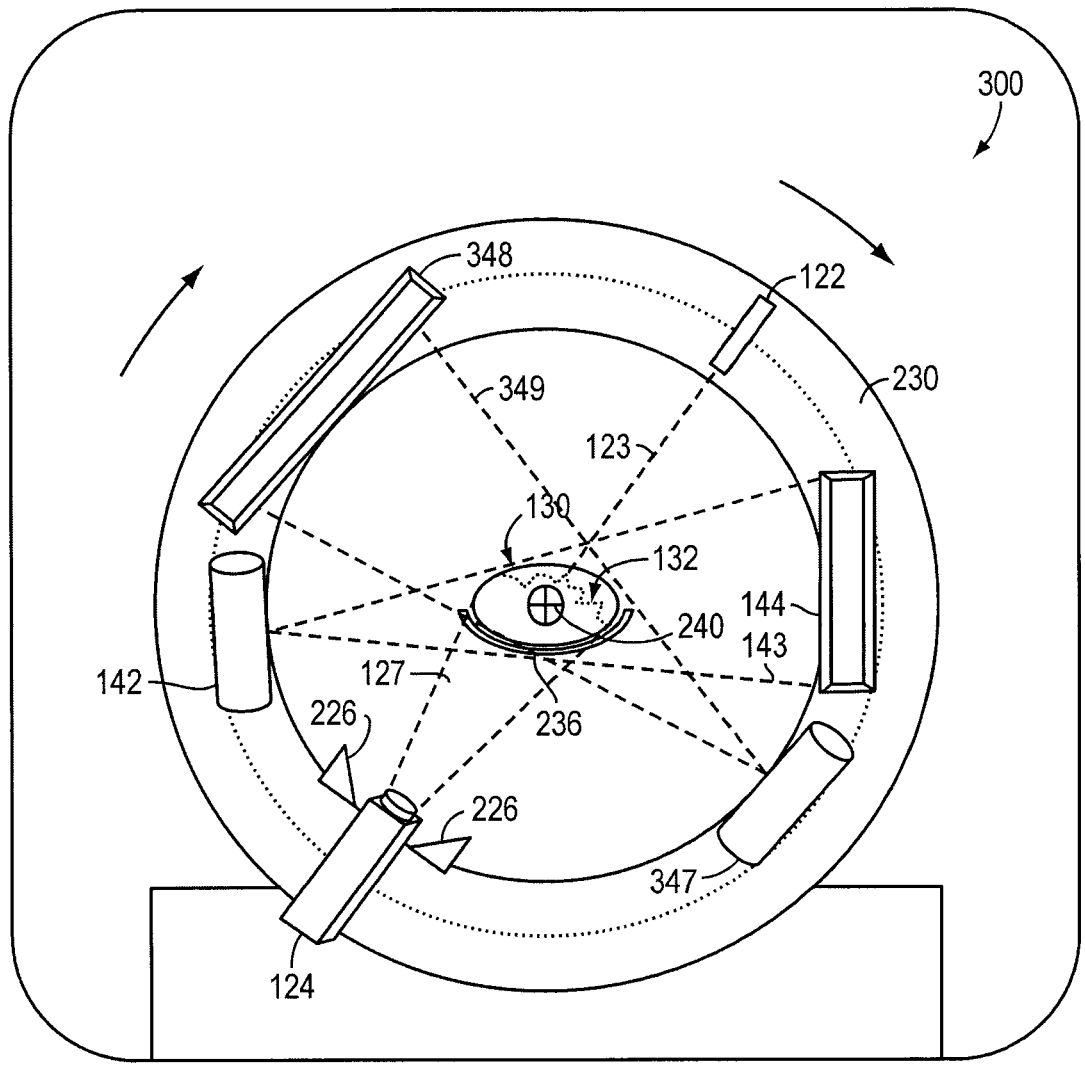
FIG. 3 is a schematic diagram of a combined dual-energy x-ray/optical tomographic imaging system featuring non-quadrature axis arrangement, according to an illustrative embodiment of the invention.

FIG. 2 is a schematic diagram of the combined x-ray and optical tomographic system 200 with x-ray and optical components mounted on a gantry 230 that rotates about an imaging chamber 130 in which the subject is placed. The combined tomography system 200 also includes an imaging chamber 130, shown pictorially in an exemplary embodiment (FIG. 2). The system 200 includes a rotating gantry subsystem 230 around the rim of which are mounted light sources 122 and 226, light detectors 124, x-ray source 142 and x-ray detector 144. Light source 226 is optional, and may provide front illumination for capturing image(s) of the object for monitoring, focusing, or other display purposes. The imaging axes 123 and 143 of the optical and x-ray subsystems respectively can be arranged in a number of different configurations, for example, the quadrature mounting as shown in FIG. 2. The configuration between the optical and x-ray axes is not limited to quadrature mounting, but could be based on any arbitrary angle, for example, in the system 300 shown in FIG. 3. Furthermore, as FIG. 3 indicates, more than one x-ray axis could be provided, for example, a dual-energy x-ray subsystem employing two x-ray sources (142, 347) and two x-ray detectors (144, 348) may be used. Advantages of such a system include the use of different x-ray beam energies simultaneously for different contrast levels, in addition to improved scan speed and temporal resolution. The object 132 under study or evaluation is positioned on a sliding support 236 such that the isocenter of the gantry 240 is contained within the object 132.

Figure 4:
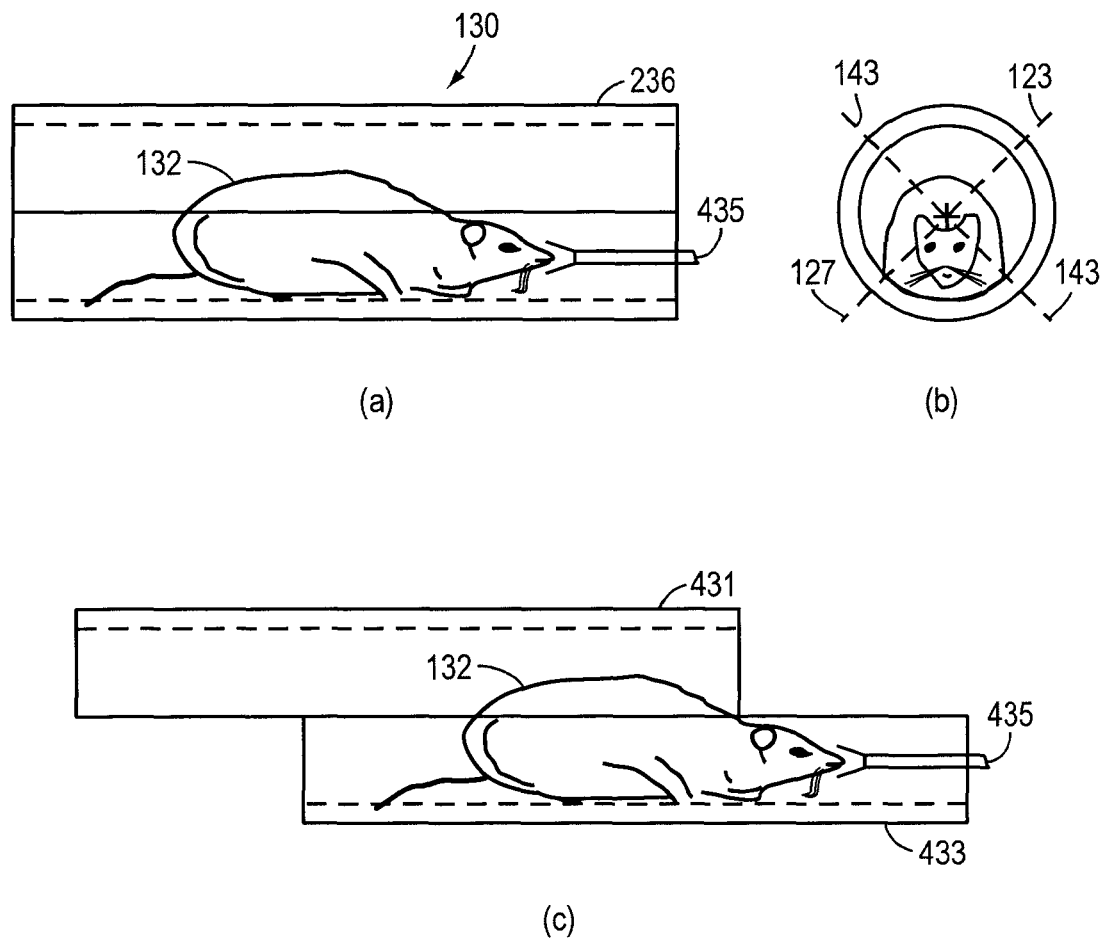
FIG. 4 is a schematic diagram of an imaging chamber of a combined x-ray/optical tomographic imaging system in which use of a free-space tomographic algorithm obviates the need for index matching fluid in the imaging chamber, according to an illustrative embodiment of the invention.

FIG. 4 is a schematic diagram of an imaging chamber 130 of a combined x-ray/optical tomographic imaging system in which use of a free-space tomographic algorithm obviates the need for index matching fluid in the imaging chamber 236. FIG. 4 shows the prone position of the subject being imaged (e.g., a mouse) 132, the two axes of detection (123/127 and 143), and an anesthesia delivery cone 435. The material and fabrication of the sliding support 236 is designed so as not to impede either the optical or x-ray radiation, and the linear motion of the sliding support 236 is controlled by a motion control system 134. Examples of suitable materials include anti-reflection coated glass and polycarbonate. The support 236 is designed to facilitate subject placement and retrieval by means of sliding top 431 and bottom 433 halves (FIG. 4(a), 4(c)). The top half 431 of the object support is not strictly necessary, but desirable in order to reduce angular sensitivity of the x-ray readout and ensure isometricity. The support 236 is also designed to integrate the mounting of an inhalation anesthesia delivery system 435. Examples of such inhalation anesthesia systems include halothane or isofluorane systems. The angular range of the imaging chamber 130, the number of imaging locations within that range for each of the optical 120 and x-ray 140 data collection systems, the linear range and sampling pitch of the object support 236, and the exposure parameters are selected in accordance with relevant factors, for example, the dimensions of the desired field of view for tomographic coverage, the desired resolution for tomographic reconstruction, and the allowable x-ray dosage for the object 132.

FIG. 5 is a schematic diagram 500 of the optical subsystem 120 of a combined x-ray/optical tomographic imaging system, showing a multi-positioned scanhead 122 and multi-position fluorescence and excitation filter wheel 529. Representative values of the excitation wavelength of the light sources 122, e.g., in the low-absorption range of red/NIR for biological tissue, are in the 650 nm-900 nm range. These values provide good tissue penetration, as they avoid the absorption peaks of hemoglobin (on the shorter end of the range) and water (on the longer end of the range). Wavelengths of emission for typical fluorescent molecular probes are Stokes-shifted by 20-30 nm from the excitation wavelengths towards the longer wavelength range of the spectrum. By making use of narrow-band excitation light sources 122, it is possible to operate the optical subsystem of a combined optical/x-ray tomographic system at multiple wavelengths, either simultaneously or sequentially, corresponding to multiple molecular probes designed for these wavelengths, thereby increasing the correlative power of the molecular readout and resolution and/or accuracy of the tomographic image. Examples of narrow-band excitation light sources 122 which may be used in the optical subsystem 120 include high-power lasers where the optical power emitted from the light source is in excess of 50 mW-100 mW, such as semiconductor laser diodes (for example GaAlAs diodes), solid-state lasers, gas lasers and tunable lasers (for example Ti-Sapphire). To enable such spectral multiplexing, it is necessary to isolate each spectral band by the use of appropriate optical filters centered on the respective channels. Typical bandpass ranges of these filters are in the range of 10 nm full-width half-maximum (FWHM). Optical filters can be discrete optical elements at fixed wavelengths, such as filters with multi-cavity interference coatings; alternatively, filters can consist of tunable electro-optical components, such as tunable liquid-crystal filters. It is considered good optical practice to provide excitation-light filters in front of each light source even if no optical multiplexing is being considered. It is also preferred to provide fluorescent-light filtration in front of the detectors in all cases. Optical filters are mounted in a filterwheel assembly 529, the operation of which can be automated in the system to ensure that the appropriate filter is placed in front of the detectors at the right time (FIG. 5(b)). Light detectors 124 can consist of charge-coupled detectors (CCD) or photo-multiplier tubes (PMT), for example. Light source assemblies are typically mounted on a fixed surface away from the rotating gantry 230 in the tomographic system, with the light emitted from the source(s) relayed by optical fiber cable(s) to a scan-head 122 mounted on the gantry 230. The scan head 122 can have one or multiple micro-collimating optical elements (FIG. 5(c)) to shape the light beam(s) exiting the fiber(s) and position it on the surface of the object 132 at one or multiple positions. The exemplary scan head 122 is shown in FIG. 5(c) in front and side views 122A, 122B. The tomographic gantry 230 rotates around the object 132, thereby providing multiple angular projections (corresponding to different gantry positions) for each of the optical and x-ray sub-systems. At each of these angular positions (at each gantry position), it is possible to acquire one or multiple images corresponding to one or multiple source locations in raster-scan fashion. Typical values of the scan data set are on the order of 100-200 angular positions for the x-ray subsystem, 15-30 angular positions for the optical subsystem, and 3-5 source locations for each angular position of the optical subsystem. The scan head 122 illustrated in FIG. 5 shows by way of example a five-element arrangement.

The combined tomography system 100 of FIG. 1 also includes an x-ray data collection system 140 having one or more x-ray sources 142 spaced from an object 132 under study. Each of the one or more x-ray sources 142 projects x-rays 143 towards the object 132. Portions of the x-rays 143 which pass through the object 132 are received by one or more x-ray sensors 144 which are disposed proximate, but spaced apart from, the object 132. Sensors 144 (detectors) are disposed about the object 132 such that the sensors 144 can receive x-ray radiation, which propagates through the object 132. The separation between the object 132 and the x-ray sensors 144 (and/or the separation between the object 132 and the x-ray sources 142) is selected in accordance with a variety of factors, for example, the distance may be selected to achieve a proper field of view, while minimizing the x-ray dose imparted to the object 132. For example, the separation between the surface of the object 132 and the end(s) of the x-ray sensor(s) (detectors) 144 nearest the surface of the object may be about 1 mm, about 5 mm, about 1 cm, about 5 cm, about 10 cm, about 20 cm, about 40 cm, about 50 cm, about 100 cm, greater than about 1 mm, greater than about 5 mm, greater than about 1 cm, greater than about 5 cm, greater than about 10 cm, greater than about 20 cm, or greater than about 50 cm. The separation between the surface of the object 132 and the end(s) of the x-ray source(s) 142 nearest the surface of the object may be about 1 mm, about 5 mm, about 1 cm, about 5 cm, about 10 cm, about 20 cm, about 40 cm, about 50 cm, about 100 cm, greater than about 1 mm, greater than about 5 mm, greater than about 1 cm, greater than about 5 cm, greater than about 10 cm, greater than about 20 cm, or greater than about 50 cm, for example. The one or more x-ray sensors 144 provide corresponding x-ray sensor signals (e.g. in the form of electrical or other types of signals) to a data processor 146. The data processor 146 digitizes, formats, and combines the digitized and formatted x-ray sensor signals into vectors for subsequent processing.

Figure 6:
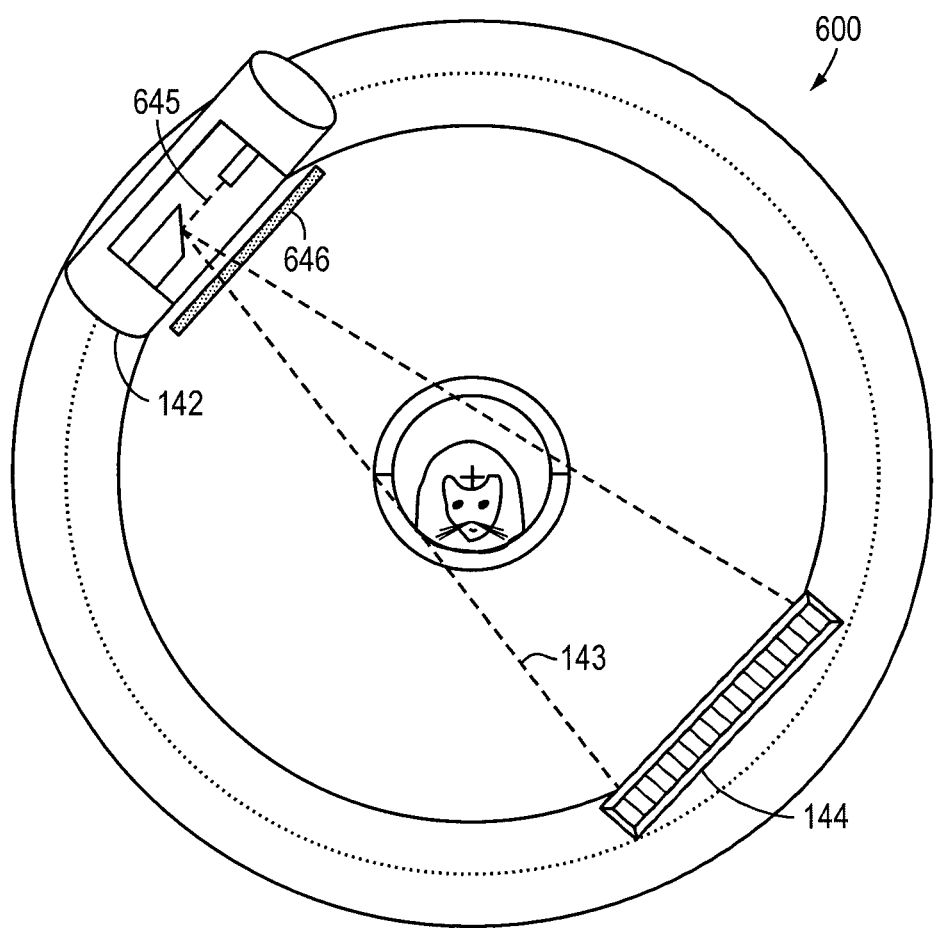
FIG. 6 is a schematic diagram of the x-ray axis of a combined x-ray/optical tomographic imaging system, showing a two-dimensional flat-panel x-ray detector and a microfocus x-ray source, according to an illustrative embodiment of the invention.

FIG. 6 is a schematic diagram of an x-ray tomographic data collection subsystem 140 of a combined x-ray/optical tomographic imaging system, showing a two-dimensional flat-panel x-ray detector 144 and a micro-focus x-ray source 142. Suitable x-ray sources 142 operate at a range of beam energies appropriate for small animal imaging, typically in the range of 20-50 kV, to provide acceptable tissue contrast. For tomographically reconstructed micro-CT resolutions on the order of 100 μm, packaged x-ray tubes with micro-focus focal spots 645 on the order of 35 μm are appropriate. It is also important to reduce the x-ray radiation dose by blocking the beam when not acquiring, for example, with the use of a shutter 646. A shutter is preferred over switching the actual x-ray source on and off, due to the slow response time and thermal equilibrium time constant of the latter approach. Fast response times on the order of milliseconds, good x-ray stopping power and cone beam angles of 10-20 degrees are provided by commercially available x-ray shutters. X-ray detector 144 shown in FIG. 6 is a two-dimensional flat array suitable for modified Feldkamp cone beam reconstructions.

Examples of such detectors include CsI-coupled CMOS solid-state photodiode arrays with high detector quantum efficiencies, low electrical noise, and high spatial resolution. Typical dimensions for the active areas of such detectors are in the range of 50 mm-125 mm on the side, with pixel dimensions in the 50 µm-100 µm range. Such detectors are capable of imaging rates on the order of 5-30 frames per second at low read-out noise and dynamic range of 2000-4000 or higher.

The x-ray data collection system 140 of FIG. 1 is coupled to an anatomical image processor 156 and, in an exemplary embodiment, the x-ray data collection system 140 provides measured x-ray data to the anatomical image processor 156 through the data processor 146. The anatomical image processor 156 computes a three-dimensional computed axial tomographic (CAT) solution corresponding to internal structures in the object 132. In one embodiment shown in FIG. 1, the anatomical image processor 156 provides this three-dimensional CAT solution to the molecular image processor 158 as an anatomical reference for image registration purposes. As indicated by dashed line 157 in FIG. 1, in certain embodiments, the anatomical image processor 156 optionally provides data to the solution processor 154 in the form of a three-dimensional map of optical absorption to enhance the performance of the optical tomographic algorithm. These enhancements may include, for example, the generation of adaptive mesh sizes to increase computational efficiency, and the use of model-based optical coefficient look-up to improve optical tomographic reconstruction and image quality.

The same x-ray data collection system hardware 140 may be used to provide data for the surface capture processor 152. The surface capture processor 152 generates a model (e.g., a mathematical description) of at least a portion of the surface of the object 132 under examination. As used herein, the term "mathematical description" is understood to include an algorithmic description formed by equations, a numerical description formed by numbers, or both, and is also herein referred to as a model of the surface of the object. Any of a variety of surface capture systems can be used to generate the model of the surface of the object 132. Surface capture systems that employ x-ray and/or light radiation are advantageously used, since hardware for x-ray and light transmission and detection are included in the combined x-ray/optical tomographic system.

Figure 7:
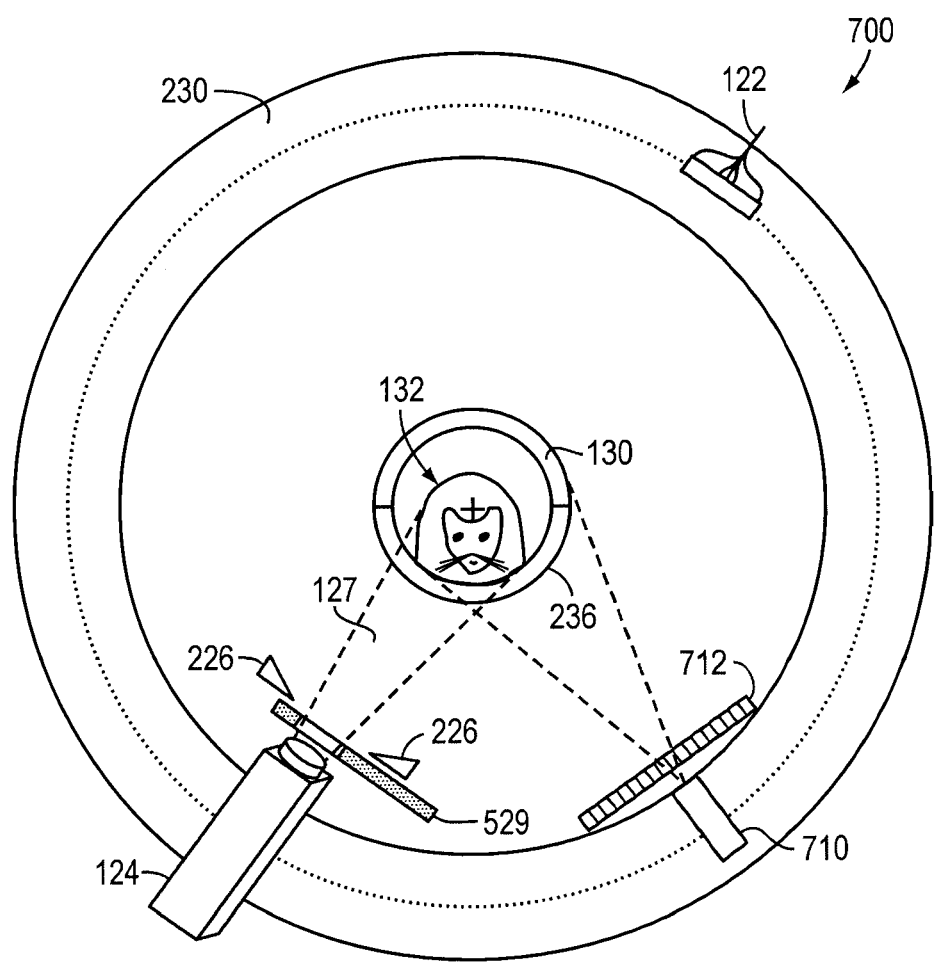
FIG. 7 is a schematic diagram of an optical three-dimensional surface capture subsystem, as part of an optical tomographic imaging system, according to an illustrative embodiment of the invention.

FIG. 7 is a schematic diagram 700 of an optical three-dimensional surface capture system, employing at least some of the hardware of the optical tomographic imaging subsystem 120 of FIG. 5, including the light detector 124 and filter assembly 529. However, an optical surface capture system may be employed with its own source and detector components dedicated for surface capture. As shown in FIG. 7, an additional light source 710 and optional filter 712 may be used, arranged in angular relation to the light detector 124 to provide optimized capture of the surface of the object 132 being imaged. A designated light source as shown at reference 710 may be used exclusively for surface capture, the light source 710 may be used in conjunction with tomography light source(s) 122 for surface capture, or the tomography light source(s) 122 may be used for both surface capture and optical tomography.

The surface capture system 152 (e.g., FIG. 1) is coupled to a solution processor 154. The solution processor 154 generates one or more optical models, as described herein in more detail. Where the object 132 is diffuse to the propagation of the light through the object 132 (e.g., where the object 132 is composed of a turbid medium, such as animal or human tissue), a first optical model generated by the solution processor 154 can model the light 123, 127 that is transmitted through the object 132. Furthermore, the first optical model can assume that the object 132 is not only diffuse but also that the object 132 is homogeneous vis-à-vis propagation of the light 123, 127 within the object. In other words, the first optical model can assume that the object 132 has no internal structures. One or more additional optical models, referred to herein collectively as a second optical model, can be generated by the solution processor 154 and include, for example, a model of the light 127 as it passes from inside of the object through the surface of the object, a model of the light 127 as it propagates through free space toward the one or more light sensors 124, and a model of optical characteristics of each of the one or more light sensors 124.

The one or more electrical signals provided by the data processor 128 can correspond to measured optical data associated with the light 123, 127 which has propagated through the object 132 and through free space before being collected by the one or more light sensors 124. The one or more models provided by the surface capture processor 152 can correspond to a theoretically derived "expected" response of the one or more light sensors 124 assuming that the object 132 is both internally diffuse and also homogeneous, e.g., having no internal structures. Where the object 132 does in fact have internal structures and is not internally homogeneous (e.g., as with an animal or human subject), the solution processor 154 is presented with an "image problem" of the form: measurements=(theoretical predictions)× (unknown distribution) where the measurements are provided by the optical data collection system 120 and the x-ray data collection system 140. The solution processor 154 solves for the unknown distribution in order to establish physical positions and characteristics of the internal structures of the object 132. The solution processor 154 provides an output to a molecular image processor 158, which overlays the optical molecular tomographic dataset (computed, for example, with an optical attenuation map and/or surface model provided by x-ray data) with the x-ray computer axial tomographic dataset. The molecular image processor 158, in turn, provides data to a display 159, which displays tomographic images of the internal structure of the object 132 (e.g., 3-D images displayed on a 2-D display screen). The solution processor 154 is described more fully in conjunction with FIG. 8.

Figure 8:
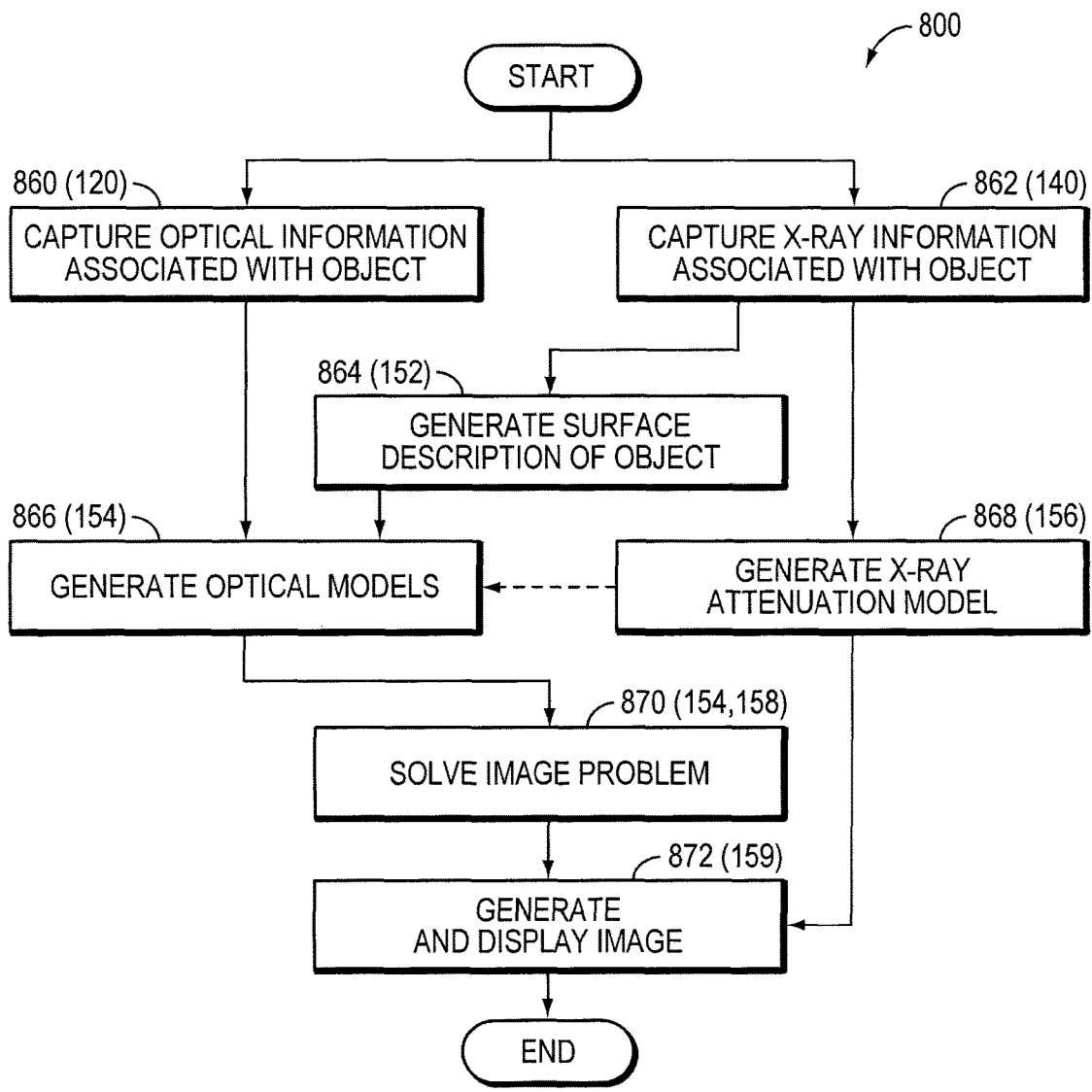
FIG. 8 is a flow chart indicating steps in a process for imaging an object with a combined x-ray and optical tomographic system, according to an illustrative embodiment of the invention.

FIG. 8 is a flow chart 800 indicating steps in a process for imaging an object with a combined x-ray and optical tomographic system, such as shown in FIG. 1 and FIG. 2. Elements of the system of FIG. 1 involved in the steps of the process 800 of FIG. 8 are indicated in parenthesis in FIG. 8. In FIG. 8, rectangular elements are herein denoted "processing blocks" and represent processor instructions or groups of instructions (e.g., computer programming code), which may be executed by a processing device (e.g., a personal computer, a general purpose computer, or any other type of suitable processor). Alternatively, the processing blocks represent steps performed by functionally equivalent circuits such as a digital signal processor circuit or an application specific integrated circuit (ASIC). It should be appreciated that the flow diagram of FIG. 8 does not depict the syntax of any particular programming language. Rather, the flow diagram illustrates the functional information one of ordinary skill in the art requires to fabricate circuits or to generate computer software or other instruction sets needed to perform the processing required as described herein.

The flow diagram of FIG. 8 illustrates an exemplary process to generate a dual modality optical/x-ray tomographic image. In processing blocks 860 and 862, optical and x-ray information, respectively, associated with an object, for example the object 132 of FIG. 1, is captured. The optical information can include, for example, information provided by the light sensors 124 of FIG. 1, and the x-ray information includes, similarly, information provided by the x-ray sensor 144 of FIG. 1. In block 868, a three-dimensional CAT model of the internal structure of the object 132 is generated from the x-ray data using standard techniques of computed tomography such as the filtered backprojection algorithm and the modified Feldkamp algorithm. Processing also proceeds to block 864 in which a surface model (e.g., a three-dimensional mathematical description) of the surface of the object 132 is generated. As discussed herein, there are various ways to generate the three-dimensional mathematical description of the surface, including, for example, optical and/or x-rays methods, such as structured light and/or tomographic methods.

Optical models can be generated as shown in processing block 866. These models describe the light transmission through the object, through the surface of the object, in free space around the object, and characteristics of light sensors used to capture the optical information in block 860. These models and optical information associated with the object are then used to solve an image problem as shown in block 870. As described above, the image problem can have the form: measurements=(theoretical predictions)×(unknown distribution), where the measurements are provided by the processing block 860 and the theoretical predictions are provided by the optical models at processing block 866. Even for a homogeneous object, light does not propagate in straight lines when passing through an object, which is diffuse to the propagation of the light (e.g., a turbid medium). A variety of techniques are known which can provide a model of the light field in a diffuse/turbid object, such as those described below and described in International (PCT) Patent Application Publication Nos. WO 2003/102558 and WO 2004/072906, the texts of which are incorporated herein by reference, in their entirety. Alternatively, analytical solutions of the diffusion equations based on Green's function solutions of homogeneous media, combined with first or high-order reflections from the surface elements as when using the Kirchoff approximation or the boundary element method can be used. While certain methods described herein represent a first order approximation to the heterogeneous problem, the Green's function solutions can be updated iteratively or can use a-priori information to represent solutions that model heterogeneous media as well. In one embodiment, an optical model can be calculated based on analytical methods, for example the Born or Rytov approximation. However different light field models of light in the diffuse medium based on analytical or numerical methods can also be used. Once the image problem is solved, processing flows to processing block 872 of FIG. 8, where the x-ray tomographic dataset is overlaid on the optical tomographic dataset, and a composite tomographic image is generated and displayed.

Figure 9:
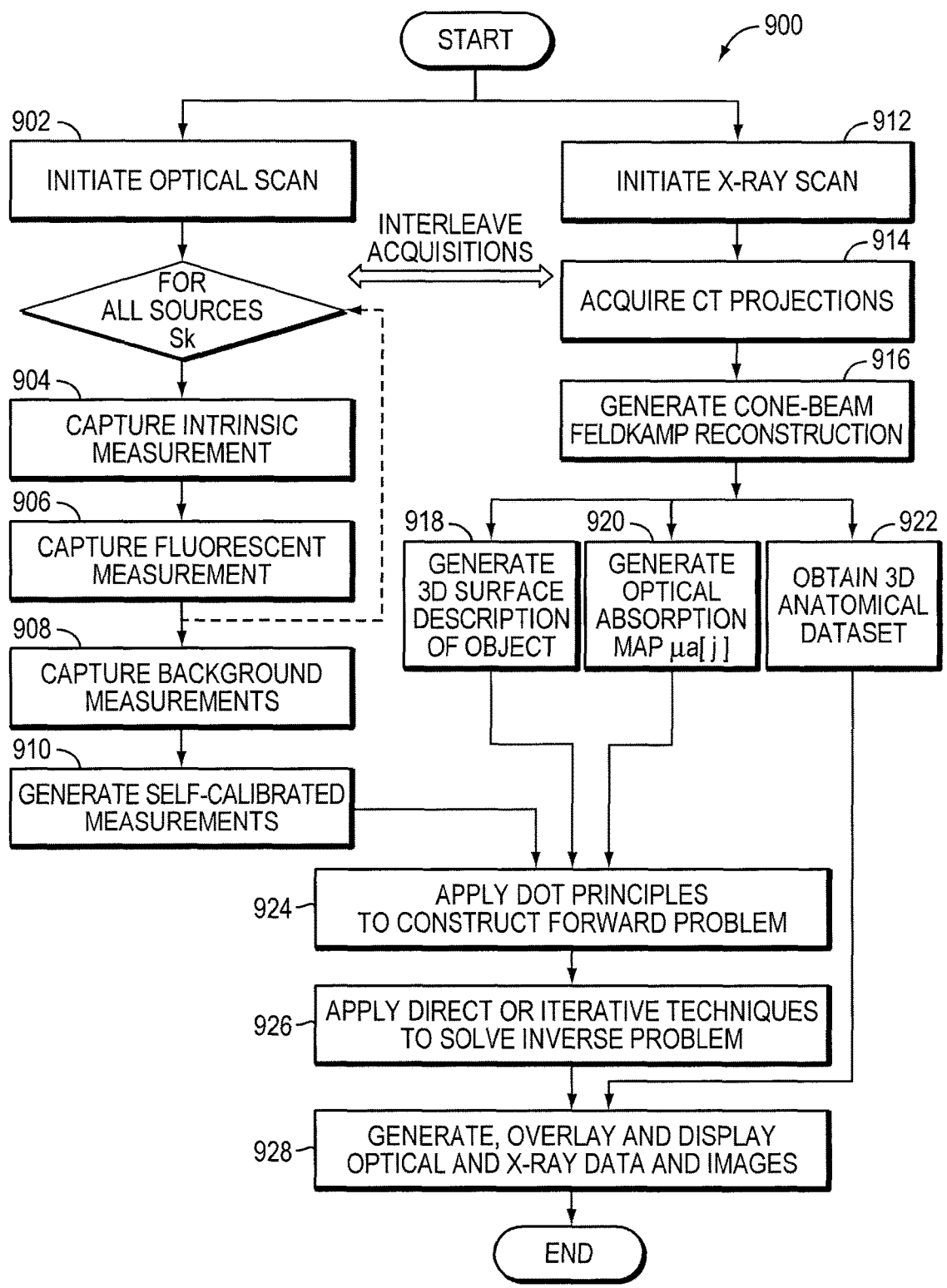
FIG. 9 is a flow chart indicating steps in a process for imaging an object with a combined free-space x-ray/optical tomographic system, according to an illustrative embodiment of the invention.

FIG. 9 is a flow chart indicating steps in a process for imaging an object with a combined x-ray/optical tomographic system, wherein x-ray radiation is detected and two kinds of light are detected from the object—(i) excitation light transmitted through the object (intrinsic measurement), and (ii) fluorescent light emitted by a fluorophore within the object (e.g., after excitation of the fluorophore by the excitation light). Data corresponding to the excitation light transmitted through the object, or intrinsic light, can be used to correct/calibrate captured fluorescent measurements, thereby providing more accurate tomographic images. The one or more fluorophores emit fluorescent light as a result of excitation by the excitation light. Background fluorescence may be accounted for by obtaining background measurements and processing data corresponding to the captured fluorescent light accordingly. In the system of FIG. 9, both an optical scan 902 and x-ray scan 912 are initiated and data is acquired in an interleaved fashion (e.g., an optical scan is obtained at a given gantry 230 position, then an x-ray scan is obtained at the gantry position, the gantry rotates to a second position, and a new optical scan and x-ray scan are obtained, and so on). In certain embodiments, it is not necessary that both an x-ray scan and an optical scan be performed at a given gantry postion. For example, an x-ray scan may be conducted at each gantry location while an optical scan may be conducted less frequently, for example, at every $2^{nd}$, $3^{rd}$, $4^{th}$, $5^{th}$, $10^{th}$, $15^{th}$ gantry location (or at any other interval), or an optical scan may be conducted at each gantry location while an x-ray scan is conducted less frequently. Aspects of the FMT (fluorescence molecular tomography) portion of the x-ray/optical tomographic system are described in U.S. Patent Application Publication No. US2004/0015062, the text of which is incorporated by reference herein. As described with respect to FIG. 9, an intrinsic measurement (e.g., excitation light transmitted through the object) and a fluorescent measurement is captured in steps 904 and 906, e.g., using a filter wheel to alternately tune to the excitation wavelength and fluorescence emission wavelength(s) of each detected fluorophore. Where there are multiple light sources $S_k$ (or multiple locations of light source(s)), an intrinsic measurement and a fluorescent measurement are obtained for each of the multiple light sources $S_k$. Background measurements are obtained in step 908, and self-calibrated measurements determined in step 910.

On the x-ray side of the system 900 of FIG. 9, CT projections are acquired by directing x-ray radiation into the object and detecting x-ray radiation transmitted through the object 914 at a plurality of positions. Step 916 is the generation of a con-beam Feldkamp reconstruction, as practiced in x-ray tomography to create an x-ray tomographic image. The data can then be used in step 918 to generate a 3D surface description of the object, in step 920 to generate an optical absorption map $\mu_{a[j]}$, and/or in step 922 to obtain a 3D anatomical dataset.

Optical data and x-ray data are combined in step 924 where the 3D surface description provides boundary conditions and the optical absorption map provides parameters used in application of DOT principles to construct the forward problem in optical tomography using the optical data. Direct or iterative techniques 926 can then be used to solve the inverse problem. In step 928, the optical tomographic image (which reflects not only the optical data but also the x-ray data via the surface description and/or optical absorption map) is generated, and a composite may be created by overlaying the tomographic image with the 3D anatomical dataset. The image may then be displayed, printed, stored, or otherwise fixed in a tangible medium.

Further detail regarding a particular embodiment of the creation and use of the optical absorption map generated in step 920 of the system 900 of FIG. 9 is described as follows. Using established boundary detection and/or image segmentation procedures applied to the x-ray CAT dataset, different parts of the tissue under examination may be delineated.

These different regions are assigned a perturbative index to their absorption coefficient as a departure from the average background absorption coefficient:

$$(\mu_a)_i = \mu_a \cdot (1+\delta_i) \quad (1)$$

where $\mu_a$ is the average background absorption coefficient, $(\mu_a)_i$ is the absorption coefficient assigned to region i and $\delta_i$ is the perturbation in optical absorption assigned to region i, evaluated to be of the form:

$$\delta_1 = \frac{1}{N \cdot (HU)_b} \cdot \sum_{j=1}^{N} (HU)_j \quad (2)$$

where $(HU)_b$ is an x-ray CAT-derived measure of density for average background tissue in Hounsfield Units, $(HU)_j$ is a similarly-derived measure of density for every CAT-reconstructed voxel in the region i (where region i comprises N voxels). The distribution of $(\mu_a)$ absorption coefficients throughout the cavity being imaged is now used instead of an assumed average absorption coefficient $\mu_a$ in the forward model of photon propagation, yielding a more accurate solution to the problem of fluorescence distribution. As an additional benefit of the optical/x-ray CAT coupling and image segmentation approach, faster convergence of the fluorescent tomography reconstruction is accomplished by assuming fluorophore concentration $C_k=0$ in tissue regions outside the target areas, based on knowledge of the physiology.

Figure 10A:
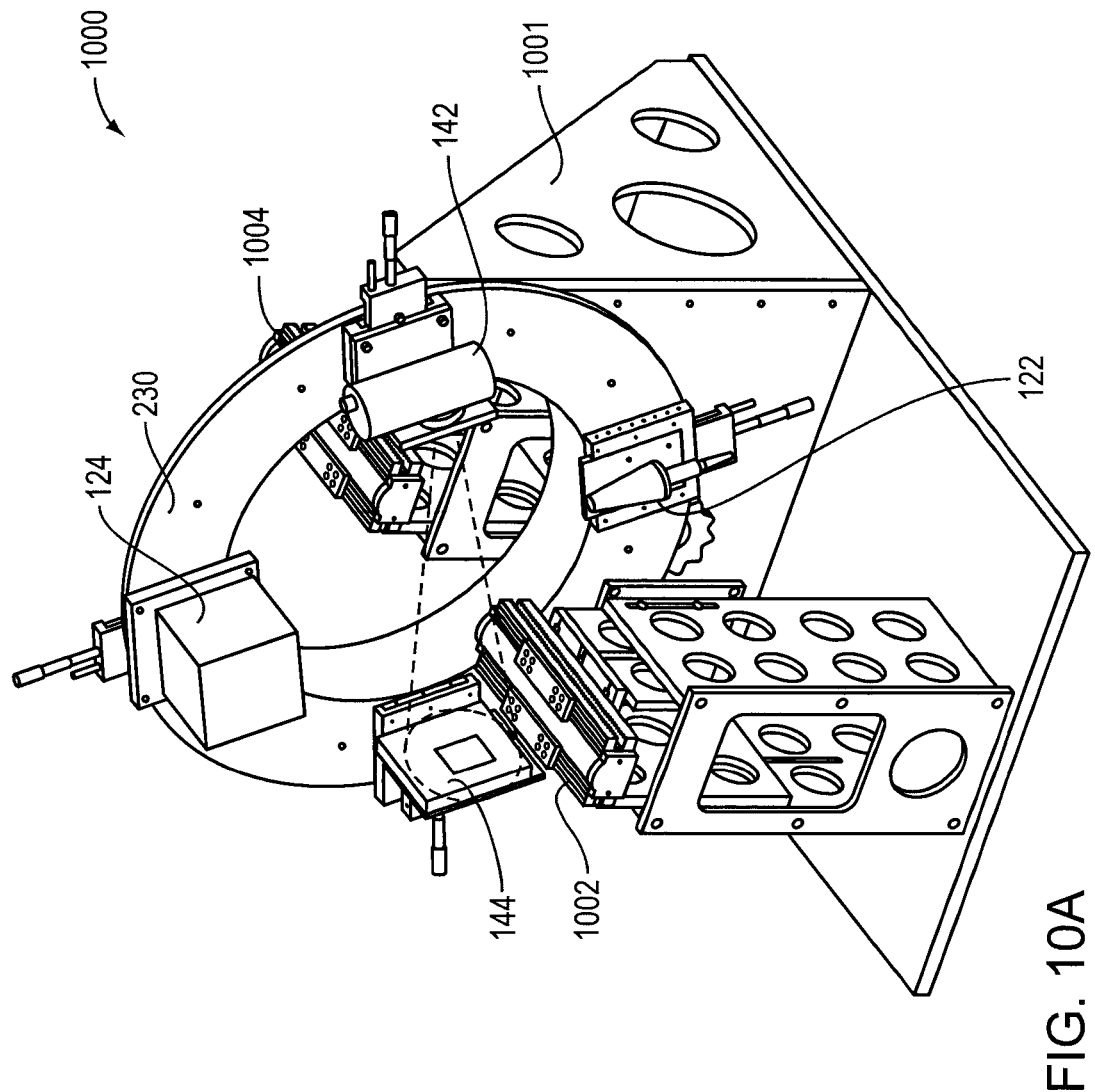
FIGS. 10A and 10B are CAD drawings of a combined x-ray and optical tomographic system with x-ray and optical components mounted on a rotating gantry, according to an illustrative embodiment of the invention.
Figure 10B:
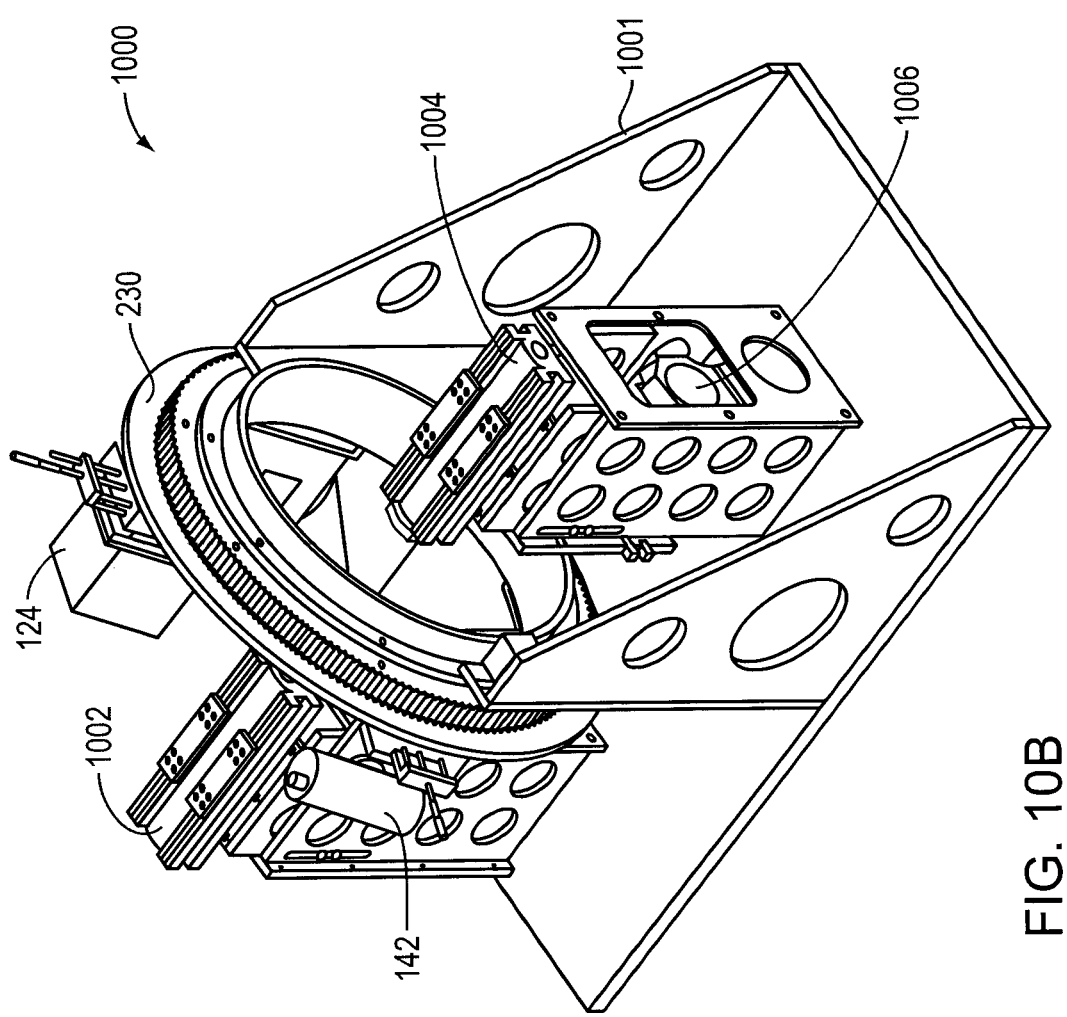

FIGS. 10A and 10B are CAD drawings showing two views of a combined x-ray and optical tomographic system with x-ray and optical components mounted on a rotating gantry 130. The system 1000 includes a rotating gantry 230 around the rim of which are mounted light source 122, light detector 124, x-ray source 142 and x-ray detector 144. The imaging axes of the optical and x-ray subsystems respectively can be arranged in a number of different configurations, for example, the quadrature mounting as shown in FIGS. 10A and 10B. The configuration between the optical and x-ray axes is not limited to quadrature mounting, but could be based on any arbitrary angle. Furthermore, more than one x-ray axis could be provided, for example, a dual-energy x-ray subsystem employing two x-ray sources and two x-ray detectors may be used. The object under study or evaluation is positioned in an imaging chamber (not shown) positioned within the center opening of the gantry 230. The assembly can be mounted on a support 1001. Positioning elements 1002 and 1004 allow adjustment of the imaging chamber in the plane perpendicular to the plane of the imaging axes, thereby facilitating the imaging of different cross-sectional volumes of the object being examined. FIG. 10B shows a motor 1006 for rotating the gantry 230.

The present invention further provides methods of in vivo imaging including the steps of administering to a subject an optical imaging probe; allowing time for the optical imaging probe to distribute in the subject; positioning the subject in a combined imaging system; collecting the x-ray and optical tomographic data sets sequentially or simultaneously; and displaying the tomographic datasets as x-ray and optical images either alone or fused. Elements of the systems described herein may be used in this method. The steps can also be repeated at predetermined interval, thereby allowing for the evaluation of the subject over time. The subject may be a vertebrate animal, for example, a mammal, including a human.

In certain embodiments, the invention features an in vivo imaging method for selectively imaging a subject containing two or more imaging probes simultaneously, wherein two or more imaging probes are administered to a subject, either at the same time or sequentially. The imaging probes can be any combination of optical or x-ray imaging agents. A single imaging agent may serve as both an optical and X-ray imaging agent, e.g., dual imaging agent. The method therefore allows the recording of multiple biological processes, functions or targets. The methods of the invention can be used to determine a number of indicia, including tracking the localization of the imaging probes in the subject over time or assessing changes or alterations in the metabolism and/or excretion of the imaging probes in the subject over time. The methods can also be used to follow therapy for such diseases by imaging molecular events and biological pathways modulated by such therapy, including but not limited to determining efficacy, optimal timing, optimal dosing levels (including for individual patients or test subjects), pharmacodynamic parameters, and synergistic effects of combinations of therapy.

The invention can be used to help a physician, surgeon, or other medical personnel to identify and characterize areas of disease, such as arthritis, cancers, metastases or vulnerable or unstable plaque, to distinguish diseased and normal tissue, such as detecting tumor margins that are difficult to detect.

The methods of the invention can also be used in the detection, characterization and/or determination of the localization of a disease, especially early disease, the severity of a disease or a disease-associated condition, the staging of a disease, and monitoring and guiding various therapeutic interventions, such as surgical procedures, and monitoring and/or development of drug therapy and delivery, including cell based therapies. The methods of the invention can also be used in prognosis of a disease or disease condition. Examples of such disease or disease conditions include inflammation (e.g., inflammation caused by arthritis, for example, rheumatoid arthritis), cancer (e.g., colorectal, ovarian, lung, breast, prostate, cervical, skin, brain, gastrointestinal, mouth, esophageal, bone, including metastases), cardiovascular disease (e.g., atherosclerosis and inflammatory conditions of blood vessels, ischemia, stroke, thrombosis), dermatologic disease (e.g., Kaposi's Sarcoma, psoriasis), ophthalmic disease (e.g., macular degeneration, diabetic retinopathy), infectious disease (e.g., bacterial, viral, fungal and parasitic infections, including Acquired Immunodeficiency Syndrome), immunologic disease (e.g., an autoimmune disorder, lymphoma, multiple sclerosis, rheumatoid arthritis, diabetes mellitus), central nervous system disease (e.g., a neurodegenerative disease, such as Parkinson's disease or Alzheimer's disease), inherited diseases, metabolic diseases, environmental diseases (e.g., lead, mercury and radioactive poisoning, skin cancer), and bone-related disease (e.g., osteoporosis, primary and metastatic bone tumors, osteoarthritis). The methods of the invention can therefore be used, for example, to determine the presence of tumor cells and localization and metastases of tumor cells, the presence and localization of inflammation, including the presence of activated macrophages, for instance in atherosclerosis or arthritis, the presence and localization of vascular disease including areas at risk for acute occlusion (e.g., vulnerable plaques) in coronary and peripheral arteries, regions of expanding aneurysms, unstable plaque in carotid arteries, and ischemic areas, and stent thrombosis. The methods and compositions of the invention can also be used in identification and evaluation of cell death, injury, apoptosis, necrosis, hypoxia and angiogenesis. The methods and compositions of the invention can also be used in for monitoring trafficking and localization of certain cell types, including T-cells, tumor cells, immune cells, stem cells, and other cell types. In particular, this method may be used to monitor cell based therapies.

In certain embodiments, the systems and methods described herein can be used to image endogenous fluorescence in a subject. For example, a gene encoding a fluorescent protein, such as green or red fluorescent protein, can be included adjacent to a gene of interest that is to be expressed in an animal or human subject using standard gene therapy and transgenic techniques. The expression of the gene of interest can be determined indirectly by imaging the fluorescent protein. If this protein is expressed, then the gene of interest has also been expressed.

Imaging Probes

The combined imaging system, for example, the system of FIG. 9, can be used with a number of different imaging probes, for example, (1) probes that become activated after target contact (e.g., binding or interaction) (Weissleder et al., *Nature Biotech.*, 17:375-378, 1999; Bremer et al., *Nature Med.*, 7:743-748, 2001); (2) wavelength shifting beacons (Tyagi et al., *Nat. Biotechnol.*, 18:1191-1196, 2000); (3) multicolor (e.g., fluorescent) probes (Tyagi et al., *Nat. Biotechnol.*, 16:49-53, 1998); (4) probes that have high binding affinity to targets, e.g., that remain within a target region while non-specific probes are cleared from the body (Achilefu et al., *Invest. Radiol.*, 35:479-485, 2000; Becker et al., *Nature Biotech.* 19:327-331, 2001; Bujai et al., *J. Biomed. Opt.* 6:122-133, 2001; Ballou et al. *Biotechnol. Prog.* 13:649-658, 1997; and Neri et al., *Nature Biotech.* 15:1271-1275, 1997); (5) quantum dot or nanoparticle-based imaging probes, including multivalent imaging probes; (6) non-specific imaging probes e.g., indocyanine green, AngioSense (VisEn Medical); (7) labeled cells (e.g., such as cells labeled using exogenous fluorophores such as VivoTag 680, nanoparticles, or quantum dots, or by genetically manipulating cells to express fluorescent or luminescent proteins such as green or red fluorescent protein; and/or (8) X-ray or MR contrast agents such as gadolinium, metal oxide nanoparticles or X-ray contrast agents including iodine based imaging agents. The relevant text of the above-referenced documents are incorporated by reference herein. Another group of suitable imaging probes are lanthanide metal-ligand probes. Fluorescent lanthanide metals include europium and terbium. Fluorescence properties of lanthanides are described in Lackowicz, 1999, Principles of Fluorescence Spectroscopy, $2^{nd}$ Ed., Kluwar Academic, New York, the relevant text incorporated by reference herein. In the methods of this invention, the imaging probes can be administered systemically or locally by injecting an imaging probe or by topical or other local administration routes, such as "spraying".

In particular, molecular imaging probes are a preferred type of imaging probe. A molecular imaging probe is a probe that is targeted to a biomarker, molecular structure or biomolecule, such as a cell-surface receptor or antigen, an enzyme within a cell, or a specific nucleic acid, e.g., DNA, to which the probe hybridizes. Biomolecules that can be targeted by imaging probes include, for example, antibodies, proteins, glycoproteins, cell receptors, neurotransmitters, integrins, growth factors, cytokines, lymphokines, lectins, selecting, toxins, carbohydrates, internalizing receptors, enzyme, proteases, viruses, microorganisms, and bacteria.

In certain embodiments, optical imaging probes have excitation and emission wavelengths in the red and near infrared spectrum in the range 550-1300 or 400-1300 nm or about 440 and about 1100 nm, between about 550 and about 800 nm, between about 600 and about 900 nm. Use of this portion of the electromagnetic spectrum maximizes tissue penetration and minimizes absorption by physiologically abundant absorbers such as hemoglobin (<650 nm) and water (>1200 nm). Optical imaging probes with excitation and emission wavelengths in other spectrums, such as the visible and ultraviolet light spectrum, can also be employed in the methods of the present invention. In particular, fluorophores such as certain carbocyanine or polymethine fluorescent fluorochromes or dyes can be used to construct optical imaging agents, e.g. U.S. Pat. No. 6,747,159 to Caputo et al. (2004); U.S. Pat. No. 6,448,008 to Caputo et al. (2002); U.S. Pat. No. 6,136,612 to Della Ciana et al. (2000); U.S. Pat. No. 4,981,977 to Southwick, et al. (1991); U.S. Pat. No. 5,268,486 to Waggoner et al. (1993); U.S. Pat. No. 5,569,587 to Waggoner (1996); U.S. Pat. No. 5,569,766 to Waggoner et al. (1996); U.S. Pat. No. 5,486,616 to Waggoner et al. (1996); U.S. Pat. No. 5,627,027 to Waggoner (1997); U.S. Pat. No. 5,808,044 to Brush, et al. (1998); U.S. Pat. No. 5,877,310 to Reddington, et al. (1999); U.S. Pat. No. 6,002,003 to Shen, et al. (1999); U.S. Pat. No. 6,004,536 to Leung et al. (1999); U.S. Pat. No. 6,008,373 to Waggoner, et al. (1999); U.S. Pat. No. 6,043,025 to Minden, et al. (2000); U.S. Pat. No. 6,127,134 to Minden, et al. (2000); U.S. Pat. No. 6,130,094 to Waggoner, et al. (2000); U.S. Pat. No. 6,133,445 to Waggoner, et al. (2000); also WO 97/40104, WO 99/51702, WO 01/21624, and EP 1 065 250 A1; and Tetrahedron Letters 41, 9185-88 (2000); all of the above incorporated by reference herein.

Exemplary fluorochromes for optical imaging probes include, for example, the following: Cy5.5, Cy5 and Cy7 (GE Healthcare); AlexaFlour660, AlexaFlour680, and AlexaFluor750 (Invitrogen); VivoTag680, VivoTag-S680, VivoTag-S750 (VisEn Medical); Dy677, Dy682, Dy752 and Dy780 (Dyomics); DyLight547, and/or DyLight647 (Pierce).

Aspects of the following two section, "Data Processing—Contact and Non-contact Optical Tomographic Systems" and "Data Processing—Free Space Optical Tomographic Systems" may be applied to optical tomography and/or x-ray tomography (application to x-ray tomography may be made even though description in the following two sections is in terms of optical tomography) and may be applied in the above-described embodiments, for example, in the processors of FIG. 1 and in the steps of FIG. 8 and FIG. 9.

Data Processing—Contact and Non-Contact Optical Tomographic Systems

Optical tomography recovers the optical properties, location, and shape of objects buried inside a specific volume by solving equations that describe light propagation through diffuse medium, such as biological tissue. As used herein, the terms "diffuse medium" or "diffusive medium" are used interchangeably and are understood to mean media where waves suffer multiple scattering events with small particles (the scatterers) within an otherwise homogeneous medium, randomizing their phase; in this case it is the average wave intensity that is studied. The average wave intensity will follow the diffusion equation, behaving in itself as a "diffuse wave" and interacting with surfaces and boundaries. The terms "non-diffuse medium" or "non-diffusive medium" are used interchangeably and are defined to mean media where waves do not suffer multiple scattering events with scatterers within the medium and maintain their phase; within these media, waves will interact and suffer multiple scattering events with surfaces and boundaries. Analytical solutions are available only for a small number of simple geometries of the air/tissue boundaries, such as cylinders, spheres, and slabs. Due to the lack of an appropriate theoretical method for more complex boundaries, numerical methods need to be used. Numerical methods offer practical simplicity but also significant computational burden, especially when large three-dimensional reconstructions are involved. Such methods include the finite element method (FEM), finite differences (FD), and the extinction theorem (ET) or Boundary Element Method (BEM).

Generally, optical tomographic analysis is divided into two steps. The first step is solving the "forward problem," in which a solution of the wave transport or "diffusion" equation, is used to describe the wave propagation through a medium with assumed optical or other wave-transmitting properties, e.g., tissue, and is used to predict the intensity of light detected emerging from this medium. In a preferred embodiment, the "diffusion equation" is $$\nabla\{D\nabla U\} + \frac{1}{c}\frac{\partial U}{\partial t} - \mu_a U = S,$$

where D is the diffusion coefficient which may be time, frequency, absorption, scattering and/or spatially-dependent, c is the speed of light in the medium, U is the average intensity or the energy density, $\mu_a$ is the absorption coefficient, and S is the source function which represents the intensity and flux distribution within the medium. As used herein, the terms "average intensity" and "energy density" can be used interchangeably, as can the terms "flux" and "fluence". The second step is solving the "inverse problem," in which the optical or other wave-transmitting properties of the medium are updated to minimize the errors observed between the predicted and measured fields.

There are several ways to solve the forward problem (by obtaining analytical and numerical solutions of the diffusion equation) and inverse problem (direct inversion, $\chi^2$-based fits, and algebraic reconstruction techniques).

Green's Function

Figure 11:
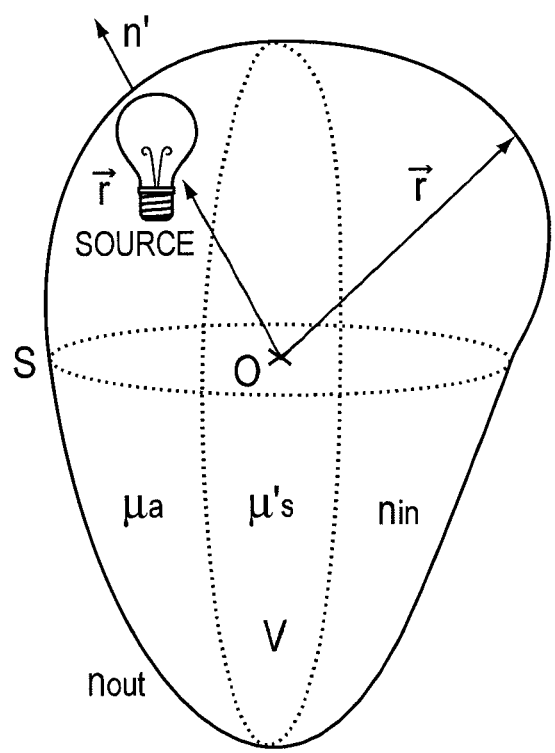
FIG. 11 depicts a surface-bounded volume of arbitrary geometry used to model a target volume of an object being imaged in an optical tomographic system, according to an illustrative embodiment of the invention; the optically diffuse volume V is surrounded by a boundary surface S of arbitrary two-dimensional or three-dimensional shape.

FIG. 11 illustrates a general imaging model where there is a diffusive volume V delimited by surface S, which can be imaged. This diffusive medium is characterized by its absorption coefficient $\mu_a$, the diffusion coefficient D, and the refractive index $n_{in}$ and is surrounded by a non-diffusive medium of refractive index $n_{out}$. Generally, any time-dependent fluctuation of the average intensity U at any point in space r can be expressed in terms of its frequency components through its Fourier transform as:

$$U(r, t) = \int_{-\infty}^{+\infty} U(r, \omega)\exp[-i\omega t]d\omega \qquad (1)$$

If in such a medium the light source is modulated at a single frequency $\omega$, the average intensity is:

$$U(r,t) = U(r,\omega)\exp[-i\omega t] \qquad (2)$$

Function U(r, t) in Eq. (2) and the functions U(r,$\omega$) in Eq. (1) represent diffuse photon density waves (DPDW) (Boas et al, (1995) *Phys. Rev. Lett.* 75:1855-1858, and obeys the Helmholtz equation with a wave number $\kappa=(-\mu_a/D+i\omega/cD)^{1/2}$, where c is the speed of light in the medium. The unknown function U(r, t) can be obtained if a so-called Green function that models light propagation within the medium from a point source to a point detector is known. Since all regimes: CW, frequency domain, and time-domain, can be expressed in terms of Eq. (1), all expressions will be derived in the frequency domain without loss of generality, and in most cases a time or frequency dependence will be assumed and not included implicitly.

In an infinite geometry (no air/tissue boundary), the so-called homogenous Green's function g(r) is obtained by solving Eq. (3):

$$\nabla^2 g(\kappa|r_s - r_d|) + \kappa^2 g(\kappa|r_s - r_d|) = -\frac{4\pi}{D}\delta(r_s - r_d), \qquad (3)$$

written here in the frequency domain (omitting time- and/or frequency dependent terms). $r_s$ is the position of the source, $r_d$ is the position of the detector, $\nabla^2$ denotes the Laplacian operator $$\nabla^2 = \frac{\partial^2}{\partial x^2} + \frac{\partial^2}{\partial y^2} + \frac{\partial^2}{\partial z^2},$$

and $\delta(r_s-r_d)$ is the Dirac's delta-function (G. B. Arfken and H. J. Weber, Mathematical Methods for Physicists (Academic Press, New York, 1995). The solution of (3) in 3D is given by Eq. (4):

$$g(\kappa|r_s - r_d|) = \frac{\exp[i\kappa|r_s - r_d|]}{D|r_s - r_d|}. \qquad (4)$$

Considering the geometry of the problem, a complete Green's function $G(r_s,r_d)$ can be defined, which models propagation of the diffuse photon waves from a point source to a point detector inside an arbitrarily shaped diffusive volume taking into account all boundaries present. By means of this complete Green's function the average intensity at a point $r_d$ inside the medium is defined as:

$$U(r_d) = \frac{1}{4\pi}\int_V S(r')G(r', r_d)dr', r_d \in V \qquad (5)$$

where S(r') is the source term (i.e., the strength of the light source at position r' given in units of energy density), and V is the volume occupied by the diffusive medium.

In infinite space the equation is $G(r_s,r_d)=g(\kappa|r_s-r_d|)$. Preferably, the source and detector are both inside the volume V.

For a homogeneous diffusive volume limited by surface S, i.e., a volume of spatially invariant absorption and scattering coefficients inside S, the solution to Eq. (5) for arbitrary geometries of S can be expressed in terms of a surface integral by means of Green's Theorem (Ripoll et al, *J. Opt. Soc. Am.* A 17:1671-1681, 2000) as:

$$G(r_s, r_d) = g(\kappa|r_s - r_d|) - \qquad (6)$$
$$\frac{1}{4\pi}\int_S\left[G(r_s r')\frac{\partial g(\kappa|r'-r_d|)}{\partial n'} - g(\kappa|r'-r_d|)\frac{\partial G(r_s, r')}{\partial n'}\right]dS',$$

where n is the surface normal pointing into the non-diffusive medium. The boundary condition between the diffusive and non-diffusive medium (Aronson, J. Opt. Soc. Am. A 16 (5):

1066-1071, 1999; Aronson R, *J. Opt. Soc. Am.* A 12, 2532 1995; Ishimaru A., Wave Propagation and Scattering in Random Media, New York: IEEE press 1997) is:

$$G(r_s, r')|_S = -C_{nd} Dn \cdot \nabla G(r_s, r')|_S, r' \in S \quad (7)$$

Introducing Eq. (7) into Eq. (6) we obtain:

$$G(r_s, r_d) = g(\kappa |r_s - r_d|) + \quad (8)$$
$$\frac{1}{4\pi} \int_S \left[ C_{nd} D \frac{\partial g(\kappa |r' - r_d|)}{\partial \hat{n}'} + g(\kappa |r' - r_d|) \right] \frac{\partial G(r_s, r')}{\partial \hat{n}'} dS'.$$

where $C_{nd}$ is a total reflectivity of the boundary surface S, integrated over all angles, and expressed through the Fresnel reflection coefficients r as:

$$C_{nd} = \frac{2 - R_J^{1 \to 0} - R_J^{0 \to 1}}{R_U^{0 \to 1}}$$

where $$R_J^{1 \to 0} = \int_0^1 [1 - |r_{10}(\mu)|^2] \mu^2 d\mu$$

$$R_J^{0 \to 1} = \int_0^1 [1 - |r_{01}(\mu)|^2] \mu d\mu$$

$$R_U^{0 \to 1} = \int_0^1 [1 - |r_{01}(\mu)|^2] \mu^2 d\mu$$

and where $\mu = \cos \theta$ for an incidence angle $\theta$, $r_{01}$ and $r_{10}$ represent the reflection coefficients when the incident wave comes from the inner, diffusive medium having an index of refraction $n_{in}$, or outer, non-diffusive medium having an index of refraction $n_{out}$, respectively, and are defined in terms of the parallel and perpendicular polarization components as:

$$|r|^2 = \frac{1}{2}(|r_\perp|^2 + |r_\parallel|^2), \quad r_\perp = \frac{n_{in} \cos \theta_t - n_{out} \cos \theta_i}{n_{in} \cos \theta_i + n_{out} \cos \theta_i},$$

$$r_\parallel = \frac{n_{in} \cos \theta_i - n_{out} \cos \theta_t}{n_{in} \cos \theta_i + n_{out} \cos \theta_t},$$

and where $\cos \theta_t$ is the cosine of the transmitted angle, which is found from Snell's law $n_{out} \sin \theta_t = n_{in} \sin \theta_i$. In Eq. (8) D is the medium's diffusion coefficient, where n is the unity vector normal to surface S and pointing into the non-diffusive medium, and $\kappa$, $r_s$, and $r_d$ are defined above for Eq. (4). Eq. (8) is an integral equation that defines the complete Green function $G(r_s, r_d)$. Substituting a known function $G(r_s, r_d)$ into Eq. (5) allows the average intensity at a point $r_d$ inside the medium $U(r_d)$ to be calculated for a given frequency $\omega$, which, in turn, allows the value of the average intensity of light at point r at time t, U(r, t) represented by Eq. (1) to be calculated.

Kirchhoff Approximation and its Application to Solving the Forward Problem

When many solutions to a forward problem need to be generated, such as in iterative reconstruction schemes, a first-order approximation to Eq. (8), applicable to arbitrary geometries in 3D is needed, both for the sake of computing time and memory. One such approximation applicable to arbitrary geometries is the Kirchhoff Approximation (KA), sometimes also known as the physical-optics or the tangent-plane method (Ogilvy, London, IOP publishing, 1991; Nieto-Vesperinas, Pergamon, N.Y., 1996 the entire teachings of which are incorporated herein by reference), so long as the curvature of the surface under study is larger than the wavelength. The KA therefore only considers first order reflections at an interface decomposed into planar components and in the case of a planar surface yields exact solutions.

Figure 12:
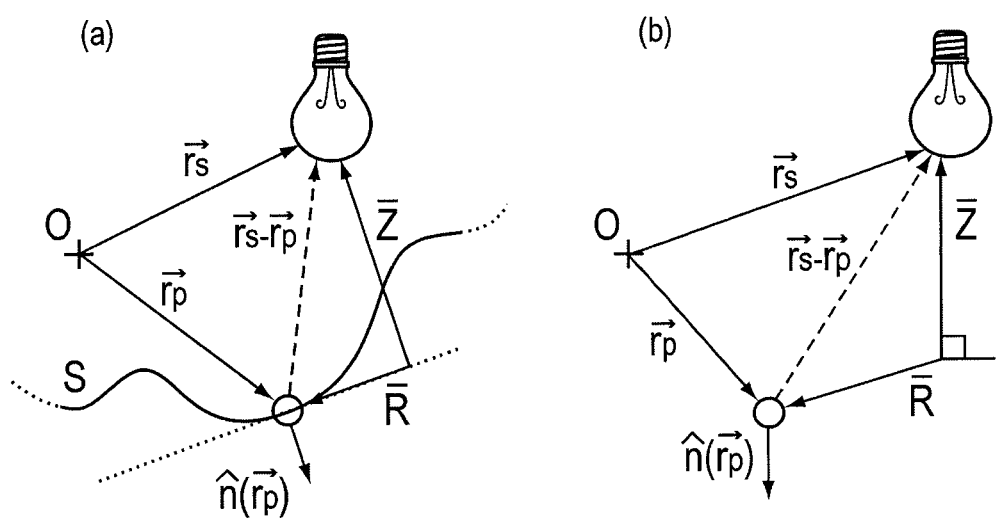
FIG. 12A depicts a vector representation at a surface of an object being imaged in an optical tomographic system, according to an illustrative embodiment of the invention; use of the Kirchhoff Approximation (KA) in solving the forward problem is demonstrated.
FIG. 12B depicts application of the Kirchhoff Approximation (KA), according to an illustrative embodiment of the invention; the KA representation in the coordinates of the tangent plane is shown.

For diffusive point sources, the Kirchhoff Approximation (KA) assumes that the surface is replaced at each point by its tangent plane. Referring to FIG. 12A, where $r_s$ is the position of the source and $r_p$ is an arbitrary point on the surface, the total average intensity U at any point $r_p$ of the surface S is given by the sum of the homogeneous incident intensity $U^{inc}$ and that of the wave reflected from the local plane of normal $n(r_p)$. In terms of the Green's function this is expressed as:

$$G^{KA}(r_s, r_p) = g(\kappa |r_s - r_p|) * [1 + R_{ND}], \quad (9)$$

where * denotes convolution:

$$g(r_s, r_p) * [1 + R_{ND}(r_p)] = \int_{-\infty}^{+\infty} [\delta(r' - r_p) + R_{ND}(r' - r_p)] g(r_s, r') dr'$$

and $R_{ND}$ is the reflection coefficient for diffusive waves defined in Fourier space as (J. Ripoll et al, *J. Opt. Soc. Am.* A 18, 2001):

$$R_{ND}(K) = \frac{iC_{nd}D\sqrt{\kappa^2 - K^2} + 1}{iC_{nd}D\sqrt{\kappa^2 - K^2} - 1}. \quad (10)$$

$g(\kappa |r_s - r_d|)$ is defined by equation (4), $\kappa$, $r_s$, and $r_d$ are defined above for Eq. (3), $C_{nd}$ is defined above for Eq. (7) and (8), and K is the spatial variable in the R=(x,y) plane in the Fourier domain (spatial frequency):

$$R_{ND}(K) = \int_{-\infty}^{+\infty} R_{ND}(R) \exp[iK \cdot R] dR.$$

Taking into consideration the different propagation directions of the incident and reflected wave with respect to the local plane, the gradient of the Green's function is:

$$\frac{\partial G^{KA}(r_s, r_p)}{\partial \hat{n}_p} = \frac{\partial g(\kappa |r_s - r_p|)}{\partial \hat{n}_p} * [1 - R_{ND}], \quad (11)$$

Eqs. (9) and (11) are directly expressed in Fourier space as:

$$G^{KA}(r_s, r_p) = \int_{-\infty}^{+\infty} [1 + R_{ND}(K)] \tilde{g}(K, \bar{Z}) \exp[iK \cdot \bar{R}] dK, \quad (12)$$

$$\frac{\partial G^{KA}(r_s, r_p)}{\partial \hat{n}_p} = \int_{-\infty}^{+\infty} [1 - R_{ND}(K)] \frac{\partial \tilde{g}(k, \bar{Z})}{\partial \bar{Z}} \exp[iK \cdot \bar{R}] dK.$$

where $(\bar{R}, \bar{z})$ are the coordinates of $|r_s - r_p|$ with respect to the plane defined by $\hat{n}(r_p)$ as shown in FIG. 12B, $$\bar{Z} = (r_s - r_p) \cdot [-\hat{n}(r_p)],$$

$$\bar{R} = \bar{Z} - (r_s - r_p). \quad (13)$$

In Eq. (12) the Fourier transform of the 3D homogeneous Green's function g(r) is given by (Goodman J W, Introduction to Fourier Optics. New York: McGraw Hill 1968):

$$g(K, \bar{Z}) = \frac{i}{2pD} \frac{\exp[i\sqrt{k^2 - K^2}\,|\bar{Z}|]}{\sqrt{k^2 - K^2}}, \quad (14)$$

$$\frac{\partial g(K, \bar{Z})}{\partial \bar{Z}} = \frac{1}{2pD}\exp[i\sqrt{k^2 - K^2}\,|\bar{Z}|].$$

where vector K is defined above for Eq. (10). (It should be noted, that a similar expression can be reached for diffusive/diffusive interfaces, by means of the corresponding reflection and transmission coefficients (Ripoll et al., *Opt. Lett.* 24:796-798, 1999)).

N-Order Diffuse Reflection Boundary Method (DRBM)

In most practical cases a more accurate solution of Eq. (8) than the one given by the KA is needed. Thus, this invention describes and teaches the use of an iterative approach that uses an arbitrary number of multiple reflections from the boundary. This approach, called the N-order Diffuse Reflection Boundary Method (DRBM), solves the exact integral Eq. (8) by iteratively decomposing each reflecting event into a sum of the series. Each term in a series is referred herein as an order of reflection. The series can be truncated when the sum meets convergence criteria defined below. Thus, the DRBM method finds the solution of the exact surface integral equation Eq. (8) by representing the solution as a sum of different orders of reflection. In this manner, one can obtain fast solutions to any degree of accuracy by adding orders of reflection. This approach takes into account the shadowing effect due to the higher reflection orders (i.e., the effect caused at those areas where the source is not directly visible due to the presence of the interface), and the high reflectivities at the interfaces (i.e., high values of the reflection coefficient Eq. (10) that introduce multiple scattering interactions at the boundary) can be modeled up to any degree of accuracy. The set of N iterations can be performed without steps of matrix inversion or solving a system of equations. Hence, the computation time of the DRBM is extremely low when compared to a rigorous numerical method such as the ET or BEM, whereas the accuracy is greatly enhanced compared to the KA.

In practice, the number of DRBM orders needed may not exceed two, due to the fact that DPDWs are highly damped (i.e., suffer from strong absorption on propagation) so that multiple scattering of DPDWs along the boundary rarely takes place. About one or two first orders of the DRBM are required for Eq. (8) in the case of non-convex surfaces that create shadowing. This is because the $1^{st}$ or at most $2^{nd}$ order scattering with the convex interface models the local illumination of the shadowed region from a secondary source reflected from the interface.

To develop the DRBM method, Eq. (8) is written in an iterative manner by using the Euler method with an evolution step $\tau$ (C. Macaskill and B. J. Kachoyan, Applied Optics 32, 2839-2847, 1993), and the assumption that the detectors are located at each of the surface points:

$$G_{DRBM}^{(N)}(r_s, r_p)|_{r \in S} = G_{DRBM}^{(N-1)}(r_s, r_p)\bigg|_{r \in S} \quad \text{(DRBM. 1)}$$

$$-\tau g(\kappa|r_s - r_p|) + \tau\frac{1}{4\pi}\int_S\left[\frac{\partial g(\kappa|r' - r_p|)}{\partial n'} + \right.$$

$$\left. \frac{1}{C_{nd}D}g(\kappa|r' - r_p|)\right]G_{DRBM}^{(N-1)}(r_s, r')dS'.$$

where $G^{(N)}$DRBM($r_p$) is the N-order Green function in the DRBM approximation. Equation (DRBM.1) is the main expression for the N-order DRBM. In order to find the solution to the integral in Eq. (DRBM.1) care must be taken when approaching values r'→$r_p$ where the Green function diverges. In this case, the Green function at r'→$r_p$ should be replaced by so-called self-induction values.

These values are known and are dependent on the medium and surface discretization area (Yaghjian, *Proc. of the IEEE* 2:248-263 (1980)). The $0^{th}$-order $G_{DRBM}$ term is calculated by solving Eq. (8) using the KA method; all subsequent orders are calculated using equation (DRBM.1) in an iterative manner. The choice of the evolution step $\tau$ will affect the speed of convergence and may be optimized. A possible optimized value of $\tau$ is t=2imag{k}/$\sqrt{W}$+1, where W is mean diameter of the volume. Other values of $\tau$ may also be found, for example by using matrix pre-conditioners (C. Macaskill and B. J. Kachoyan, Applied Optics 32, 2839-2847 (1993)).

Once the expression at the boundary for the N-th approximation is obtained through Eq. (DRBM.1), the intensity $U_{DRBM}$ anywhere inside the diffusive volume can be found through:

$$G_{DRBM}^{(N)}(r_s, r_d) = \quad \text{(DRBM. 2)}$$

$$g(\kappa|r_s - r_d|) + \frac{1}{4\pi}\int_S\left[\frac{\partial g(\kappa|r' - r_d|)}{\partial n'} + \frac{1}{C_{nd}D}g(\kappa|r' - r_d|)\right]$$

$$G_{DRBM}^{(N)}(r_s, r')dS'.$$

$$U_{DRBM}^{(N)}(r_d) = \int_V S(r')G_{DRBM}^{(N)}(r', r_d)dr'$$

A direct relation between computing times for different orders can easily be found by evaluating the following:

Time{DRBM(N>2)}=(N−1)*[Time{DRBM(2)−Time{DRBM(1)}]

In the following paragraphs, preferred embodiments of the invention are described that further accelerate the computation of $U^{(N)}$DRBM($r_p$) using equation (DRBM.1).

Adaptive-DRBM

In a preferred embodiment of the invention, the DRBM can adaptively adjust the number of N-order reflections. In one embodiment, the adaptive adjustment can be achieved by detecting complex boundaries, i.e., surfaces with high spatial variation, by monitoring the gradient of the boundary and automatically increasing the density of local surface discretization i.e., the number of discretization areas that define surface S at that local point, and the number of orders of reflections to include in the DRBM calculations. (In the case of a plane interface, the $0^{th}$ order DRBM yields an exact solution.) As used herein the spatial variation is high if substantial spatial changes occur in a range shorter than the decay length ($L_d$) of the diffusive wave. Therefore higher numbers of discretization areas need to be included for those regions where $|\nabla S|\cdot L_d$>1, increasing proportionally with $|\nabla S|$. The decay length depends on the optical properties of the medium and the modulation frequency (with CW illumination is in the order of a few cm in the Near-infrared for tissue) and is defined as the inverse of the imaginary component of the complex wave number $\kappa$, $L_d$=1/Im{$\kappa$} where $\kappa$=$(-\mu_a/D+i\omega/cD)^{1/2}$.

In another embodiment, the adaptive adjustment can be achieved by monitoring the relative change in value of the calculated intensity added by each iteration step and stopping the number of iterations based on a convergence criterion. Typical criteria include limits on the relative change in a value of a function after each iterated step and limits on new contributions of the new iteration step to the overall value of the intensity. For example, the iterative process can be stopped when the relative change in the value of intensity falls below about 0.1% to about 10%, preferably below 1%. In another example, the iterative process can be stopped when a new contribution falls under a certain threshold value $\tilde{\xi}$. The threshold value can be selected, for example, to be about twice the value of noise.

Additionally, since the DRBM is based on a surface integral equation (DRBM.1) for waves in an absorbing medium, not all surface points contribute equally to the intensity at a certain detector point since the distances between each surface point and the detector vary. Therefore, contribution from surface points further away from the detector will suffer higher attenuation on propagation than points nearer to the detector. Therefore, in another embodiment of the invention, a threshold value that determines which surface points and their corresponding surface values $G_{DRBM}(r_s,r)|_{r \in S}$ are taken or discarded in the surface integral equation (DRBM.1) can be selected so that only surface points that satisfy the condition:

$$i_{thresh}{}^o g(r_s, r_p)|_{r_p iS} > \text{thresh}$$

$$S \textcircled{R} S(i_{thresh})$$

where $i_{tresh}$ is an index of a surface point, will be considered when modeling the total intensity at the detector. Here $S(i_{tresh})$ is the total surface considered in Eqs. (DRBM.1) and (DRBM.2), and g(r) is defined above by Eq. (4).

Increasing Time Efficiency

In another embodiment of the invention, a convenient approximation to the solution of Eq. (8) may be found by the method of images. The method of images is applied by taking into account the boundary condition at a diffusive/non-diffusive interface given by Eq (7), which can be approximated to:

$$G(r_s, r) \sim G(r_s, r[z=0]) \exp(-C_{nd} D \cdot z), z > 0 \qquad (15)$$

where $C_{nd}$ and D are defined above for Eqs. (3) and (8) and z is a coordinate along the direction normal to the local tangent plane and pointing into the non-diffusive medium (U or G is defined at the interface, i.e., U approached from inside or from outside must be equivalent and z must be non-negative). For convenience a planar interface is assumed at z=0 in Eq. (15). Using Eq. (15), the boundary condition (7) can be approximated to one that makes the diffuse intensity U equal to zero at a fictitious boundary at $z_{ext} = C_{nd} D$ such that:

$$G(r_s, r[z=C_{nd}D]) = 0.$$

In this way, the boundary values for the $0^{th}$ order DRBM can be found as:

$$G_{DRBM}{}^{(0)}(r_s, r_p) = [g(\bar{R},\bar{Z}) - g(\bar{R}, \bar{Z} + C_{nd}D)]. \qquad (\text{DRBM.3})$$

where $r_p$ is a point at the surface S and g is the infinite homogenous Green function defined by Eq. (4), $(\bar{R},\bar{Z})$ are defined above by Eq. (13), $C_{nd}$ and D are defined above for Eqs. (3) and (8), and their product represents a fictitious distance $z_{ext}$ from the real boundary at which the intensity is approximately zero.

With this expression, the $1^{st}$ order DRBM can be calculated assuming a source at $r_s$, and a detector at $r_d$, both inside the diffusive volume, as a summation over N locally planar discrete areas $\Delta S$ as:

$$G_{DRBM}^{(1)}(r_s, r_d) = \qquad (\text{DRBM. 4})$$

$$g(r_s - r_d) - \frac{1}{4\pi}\sum_{p=1}^{N}\left[\frac{\partial g(\kappa|r_p - r_d|)}{\partial n_p} + \frac{1}{C_{nd}D}g(\kappa|r_p - r_d|)\right]$$

$$\Delta S(r_p) \times [g(\bar{R},\bar{Z}) - g(\bar{R}, \bar{Z} + C_{nd}D)]$$

Here the infinite space Green function g is defined above, $\Delta S(r_p)$ is defined as the discretized surface area at point $r_p$, $C_{nd}$ and D are defined above for Eqs. (3) and (8) and R and Z are defined above for Eq. (13). Using this new expression, computation times are greatly diminished, since it is an analytical approach and may not involve any Fourier transforms.

Application to Non-Contact Measurements

Techniques described herein can be applied both to contact and non-contact measurements, as well as for any diffuse and non-diffuse interfaces as related to forming a tomographic image using waves and including. As used herein, the term "contact measurement" means measurement that takes place with the detector in contact with the surface or at a distance of less than about 1 mm from the surface. The term "non-contact measurement" refers to measurements that take place with the detector at a distance of greater than 1 mm from the surface. The contemplated waves include light waves, infra-red waves, waves of temperature, acoustic waves and the like. Contemplated modes of tomography include optical tomography, fluorescence-mediated tomography, near-field optical tomography, tomography with temperature waves and generally any surface-bounded inversion problems of tissues and other diffuse or diffuse-like or highly scattering medium. The application of DRBM to performing non-contact measurements will now be described. Referring to the geometrical scheme described in FIG. 11 and by using Eq. (16) below, the flux $J_n$ at any point of the boundary between the diffusive and non-diffusive medium can be found as:

$$J_n(r_p) = -D\frac{\partial U(r_p)}{\partial \hat{n}_p} = \frac{1}{C_{nd}}U(r_p) \qquad (16)$$

where $U(r_p)$ is defined as the average intensity at the surface point $r_p$, $C_{nd}$ and D are defined above for Eqs. (3) and (8), $r_p$ is a point on the boundary, $n_p$ is a unity vector normal to the boundary at point $r_p$ and directed towards the non-diffusive medium. As used herein, the term flux is defined as the power flowing through a surface S within an interval of time t and has units of power per area per second in the time-domain and units of power per area in the frequency or CW domain. The flux detected at any point r in the non-scattering (i.e., non-diffusive) medium, can be represented as:

$$J(r) = \frac{1}{\pi}\int_S J_n(r_p)\Gamma(r_p - r)dr_p \qquad (17)$$

where $\Gamma(r_p-r)$ is a function defined in Eq. (18), which maps surface values $r_p$ at S onto a non-contact detector at r, and the integration is performed over all the surface points. The expression for $\Gamma$ in Eq. (17) is given by:

$$\Gamma(r_p - r) = \frac{\exp\left(i\frac{\omega}{c}|r_p - r|\right)}{|r_p - r|^2} \xi(r_p - r)\cos\theta_p \cos\theta, \quad (18)$$

$$\cos\theta_p = n_p \cdot \frac{(r - r_p)}{|r - r_p|}, \cos\theta = n \cdot \frac{(r_p - r)}{|r_p - r|},$$

where $\omega$ is the light wave frequency, c is the speed of light, $r_p$ and r are defined above for Eqs. (16) and (17), $\xi$ is the visibility factor, which is either unity, if both points $r_p$ and r can be joined by a straight line without intersecting the surface interface, i.e., when they are visible to each other, or zero otherwise. In Eq. (18), n is a unity vector normal to the surface of the detector or detector plane at point r of the non-scattering medium where the flux J is measured. The numerical aperture (NA) of the detector, may be represented by a general function $f$ which models light detection at different angles at the detector position r. Including function $f$, Eq. (18) can be rewritten as:

$$\Gamma(r_p - r) = f(NA, \sin\theta)\frac{\exp\left(i\frac{\omega}{c}|r_p - r|\right)}{|r_p - r|^2}\xi(r_p - r)\cos\theta_p \cos\theta, \quad (19)$$

$$\cos\theta_p = n_p \cdot \frac{(r - r_p)}{|r - r_p|}, \cos\theta = n \cdot \frac{(r_p - r)}{|r_p - r|},$$

An example of a function $f$ which represents the NA of the detector would be a Gaussian function with full width at half-maximum equivalent to the NA:

$$f = \exp(-\sin\theta^2/NA^2).$$

Upon discretization of surfaces called for by the DRBM, Eq. (17) can be rewritten as:

$$J^{DRBM}(r) = \frac{1}{\pi}\sum_p J_p^{DRBM}(r_p)\Gamma(r_p - r)\Delta S(r_p) \quad (20)$$

In order to find the average intensity U at the detector, we will approximate it by $U(r)=C_{nd} J(r)$, where now $C_{nd}$ is defined for the detector/non-diffusive medium interface according to Eq. (8).

The expression Eq. (20) for non-contact detectors is independent of the sources. In order to obtain an expression for non-contact sources, the same formulation can be used, due to the source-detector invariance.

In certain embodiments, the solution processor 154 of FIG. 1 solves the equation (DRBM.1) for an unknown function $G_{DRBM}^{(N)}$, where $G^{(n)}{}_{DRBM}(r_p)$ is the N-order Green function in the DRBM approximation, $C_{nd}$ is as previously defined in Eq. (8), D is the diffusion coefficient inside the diffusive medium, n is a unity vector normal to boundary surface S and pointing into the non-diffusive medium, $\kappa$ is a diffusive wave number $\kappa=\sqrt{-\mu_a/D+i\omega/c}$, for a modulation frequency $\omega$, c is a speed of light in the medium, $\mu_a$ is an absorption coefficient, $\tau$ is an evolution step, and $r_s$, and $r_p$ are source and detector positions respectively, and wherein the detector is located at the surface, and where g is the Green's function for an infinite homogeneous diffusive medium with a wave number $\kappa$ given by formula $g(\kappa|r-r'|)=\exp[i\kappa|r-r'|]/D|r-r'|$, and N is an arbitrary integer not smaller than 1.

In another embodiment, the solution processor 154 of FIG. 1 solves the equation (DRBM.2) for an unknown function $G_{DRBM}^{(N)}$, where $G^{(N)}{}_{DRBM}(r_p)$ is the N-order Green function in the DRBM approximation, $C_{nd}$ is as previously defined in Eq. (8), D is the diffusion coefficient inside the diffusive medium, n is a unity vector normal to boundary surface S and pointing into the non-diffusive medium, $\kappa$ is a diffusive wave number $\kappa=\sqrt{-\mu_a/D+i\omega/c}$, for a modulation frequency $\omega$, c is a speed of light in the medium, $\mu_a$ is an absorption coefficient, $\tau$ is an evolution step, and $r_s$, and $r_p$ are source and detector positions respectively, and wherein the detector is located at the surface, and where g is the Green's function for an infinite homogeneous diffusive medium with a wave number $\kappa$ given by formula $g(\kappa|r-r'|)=\exp[i\kappa|r-r'|]/D|r-r'|$, N is an arbitrary integer not smaller than 1, $U_{DRBM}^{(N)}(r_d)$ is a wave intensity at point $r_d$, and $S(r')$ is the strength of the light source at position $r'$ expressed in units of energy density.

The processing can further include monitoring a gradient of the boundary surface to detect complex boundaries and automatically increasing a density of local surface discretization and the number N of terms in a series, if the boundary is complex. Alternatively, the processing includes monitoring relative change in a value of the calculated intensity added by each term of the series and truncating the series by selecting a finite number N of terms in a series, when the relative change in a value of the calculated intensity meets convergence criteria. In one embodiment, the processing includes monitoring the gradient of a surface boundary to detect complex boundaries, automatically increasing a density of local surface discretization and the number N of terms in a series, if the boundary is complex, and optimizing an evolution step $\tau$ by assigning a value, of about $t=2\text{imag}\{k\}/\sqrt{W}+1$, wherein W is a mean diameter of the diffusive medium.

The medium being imaged generally fills a volume V of arbitrary geometry. Alternatively, the volume or object has a fixed geometry whose surface is defined in terms of a continuous function $f[z(x,y)]$ in Cartesian, polar or cylindrical coordinates. The object can be a sample of a biological tissue or an animal, including a human. The object may also be non-mammalian, i.e., C. elegans, drosophila, etc.

Any combination of one or more source detection technologies can be used for tomography applications as described herein. One technique is continuous wave (CW) imaging. This technique uses light of constant intensity and measures either (1) the signal due to a distribution of excited fluorophores or (2) the attenuation of light (due to tissue absorption and scattering) employing multiple source-detector pairs. The technique usually offers good signal-to-noise (SNR) characteristics. However, it may not be best suited for imaging of intrinsic tissue contrast since it usually introduces significant cross-talk between the calculations and imaging of absorption and scattering coefficients. On the other hand, if the background optical properties are known, the method is well-suited for imaging fluorophore concentration in the steady-state. A more elaborate approach is to use intensity modulated (IM) light at a single or at multiple frequencies. With this method, modulated light attenuation and phase shifts, relative to the incident light, can be measured for multiple source-detector pairs. Compared to a CW measurement, which yields intensity attenuation, the IM technique offers two pieces of information, i.e., intensity attenuation and phase shift per source-detector pair. Amplitude and phase are usually uncorrelated measurements and can more efficiently resolve the absorption and scattering coefficient of intrinsic contrast. In the fluorescence mode, the technique can image two sets of information, fluorophore concentration and fluorescence lifetime.

A third approach, the time-resolved (TR) technique, uses short pulses of light injected into the tissue. The technique resolves the distribution of times that the detected photons travel into the medium for multiple source-detector pairs. Time-resolved methods contain the highest information content per source-detector pair, comparable only to the IM method performed simultaneously at multiple frequencies. This can be easily explained when one considers that the Fourier transform of the time-resolved data yields information at multiple frequencies up to 1 GHz, including the continuous wave components (f=0 MHz) used by the previous two methods. Therefore, the time-resolved method offers a CW component for direct comparison with the CW system, but also intensity attenuation and phase-shift measurements at multiple-frequencies (via the Fourier transform) that can image intrinsic absorption and scattering, and also fluorophore concentration and fluorescence lifetime.

The step of detection can be accomplished by either contact or non-contact measurements of emitted wave intensity. In one embodiment, contact measurements are made using optical guides, fiber guides, optical matching fluids, lenses or any combination thereof. In another embodiment non-contact measurements are made using a system of lenses, pinholes, apertures or any combination thereof. Non-contact measurements are preferred.

Data Processing—Free Space Optical Tomographic Systems

Figure 13:
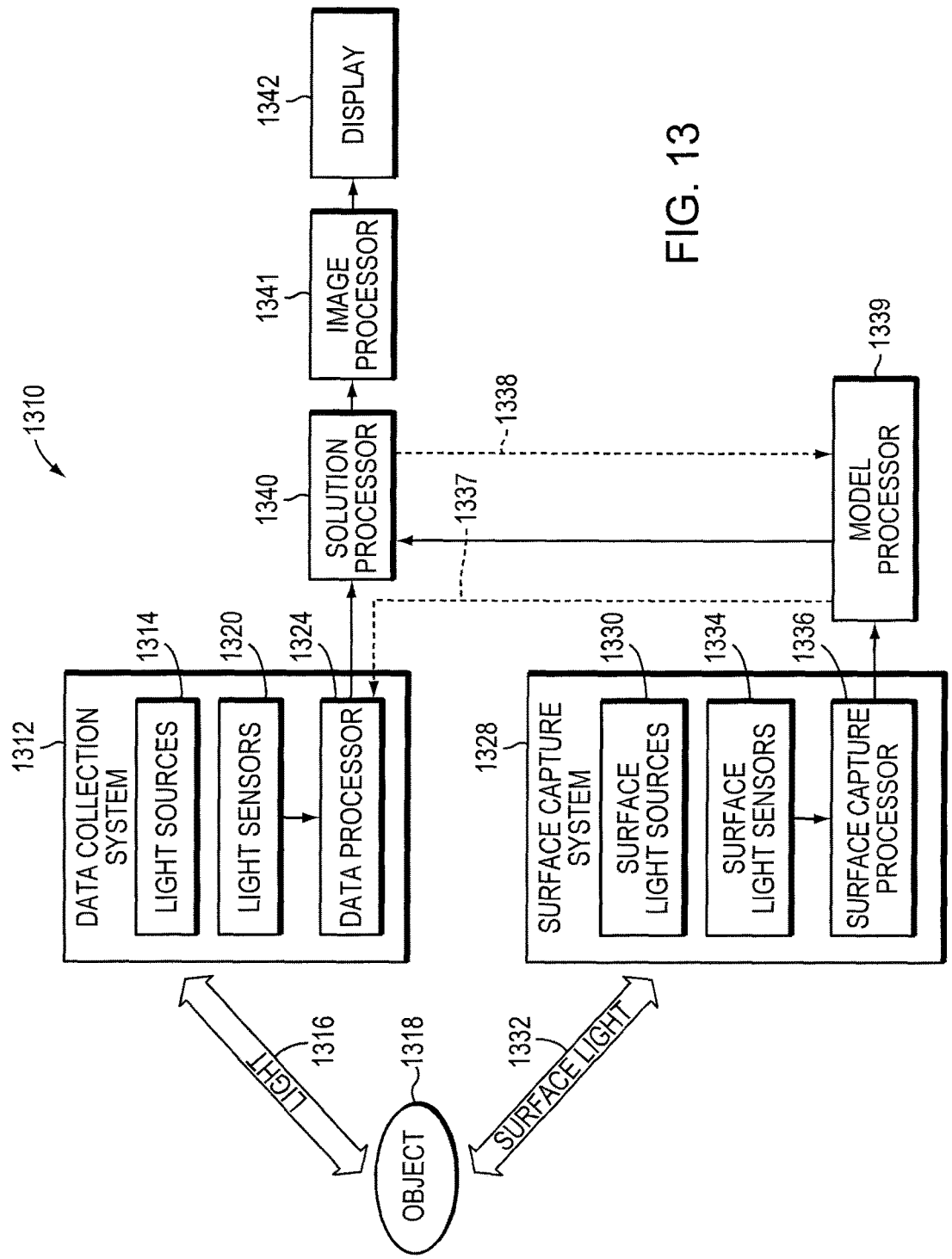
FIG. 13 is a block diagram of an exemplary free space optical tomographic system/subsystem, according to an illustrative embodiment of the invention.

Referring now to FIG. 13, in certain embodiments, an optical tomography system 1310 includes a data collection system 1312 having one or more light sources 1314 spaced from an object 1318 under test. Each of the one or more light sources 1314 projects light 1316 toward the object 1318. Portions (not shown) of the light 1316 which pass through the object 1318 are received by one or more light sensors 1318 which are disposed proximate, but spaced apart from, the object 1318. Sensors 1320 are disposed about the object 1320 such that the sensors 1320 can receive light, which propagates through the object 1318. In one particular exemplary embodiment, the light sensors 1320 are disposed to be approximately one centimeter apart from the object 1318, proximate a side of the object 1318 which is substantially opposite from the side of the object upon which the light 1316 is directed. However, in other embodiments, the one or more light sensors 1320 can be disposed more that one centimeter or less than one centimeter apart from object 1318, and can be disposed apart from any side of the object. In another exemplary embodiment, the light sensors are disposed to be between five and twenty-five centimeters from the surface of the object. The separation between the surface of the object and the light sensors is selected in accordance with a variety of factors, including, but not limited to, a distance that can achieve a proper focal depth, while maximizing light collection capacity.

The light sensors 1320 receive the light, which passes through the object 1318. Necessarily, since the one or more light sensors 1314 are spaced from the object, the light propagates in free space prior to reaching the sensors 1314. The one or more light sensors 1320 provide corresponding light sensor signals (e.g. in the form of electrical or other types of signals) to a data processor 1324. The data processor 1324 digitizes, formats, and combines the digitized and formatted light sensor signals into vectors for subsequent processing, the functions of which are described in more detail in conjunction with FIGS. 16B and 17B.

In some embodiments, the light sensors 1320 are also adapted to receive fluorescent light generated by fluorophores internal to the object 1318, for example from fluorescent probes injected into the object 1318 which tend to coalesce in particular structures or molecules within the object 1318.

The data collection system 1312 is coupled to a solution processor 1340 and, in the exemplary embodiment of FIG. 13, the data collection system 1312 provides measured optical data to the solution processor 1326 through the data processor 1324. The solution processor 1340 provides a solution to an "image problem" described more fully below, which provides image data corresponding to internal structures in the object 1318.

The optical tomography system 1310 also includes a surface capture system 1328 having one or more surface light sources 1330 spaced from the object 1318. The one or more surface light sources 1330 project surface light 1332 at the object 1318. Portions of the surface light 1332 reflect from the surface of the object 1318 and are received by one or more surface light sensors 1334. The one or more surface light sensors 1334 receive the surface light reflected from the object 1318 and provide corresponding surface light sensor signals (e.g. in the form of electrical or other types of signals) to a surface capture processor 1336. In response to the surface light sensor signals, the surface capture processor 1336 generates a model (e.g., a mathematical description) of at least a portion of the surface of the object 1318 from which the surface light reflects. One surface capture system 1328 generates the surface light 1332 in a predetermined spatial pattern which is received by the one or more surface light sensors 1334 provided as one or more three-dimensional cameras.

The surface capture system 1328 is coupled to a model processor 1339. The model processor 1339 generates one or more optical models. The optical models are described more fully below. Where the object 1318 is diffuse to the propagation of the light 1318 through the object, a first optical model generated by the model processor 1339 can model the light 1316 in the object 1318. Furthermore, the first optical model can assume that the object 1316 is not only diffuse but also that the object 1316 is homogeneous vis-à-vis propagation of the light 1316 within the object. In other words, the first optical model can assume that the object 1316 has no internal structures. Other optical models, referred to herein collectively as a second optical model, which can be generated by the model processor 1339 include, for example, a model of the light 1316 as it passes from inside of the object through the surface of the object, a model of the light 1316 as it propagates through free space toward the one or more light sensors 1320, and a model of optical characteristics of each of the one or more light sensors 1316.

In the exemplary embodiment of FIG. 13, the model processor 1339 provides the one or more optical models described above to the solution processor 1340. Therefore, the solution processor receives the one or more light sensor signals (e.g., electrical signals) from the data processor and the one or more optical models from the model processor.

Figure 16A:
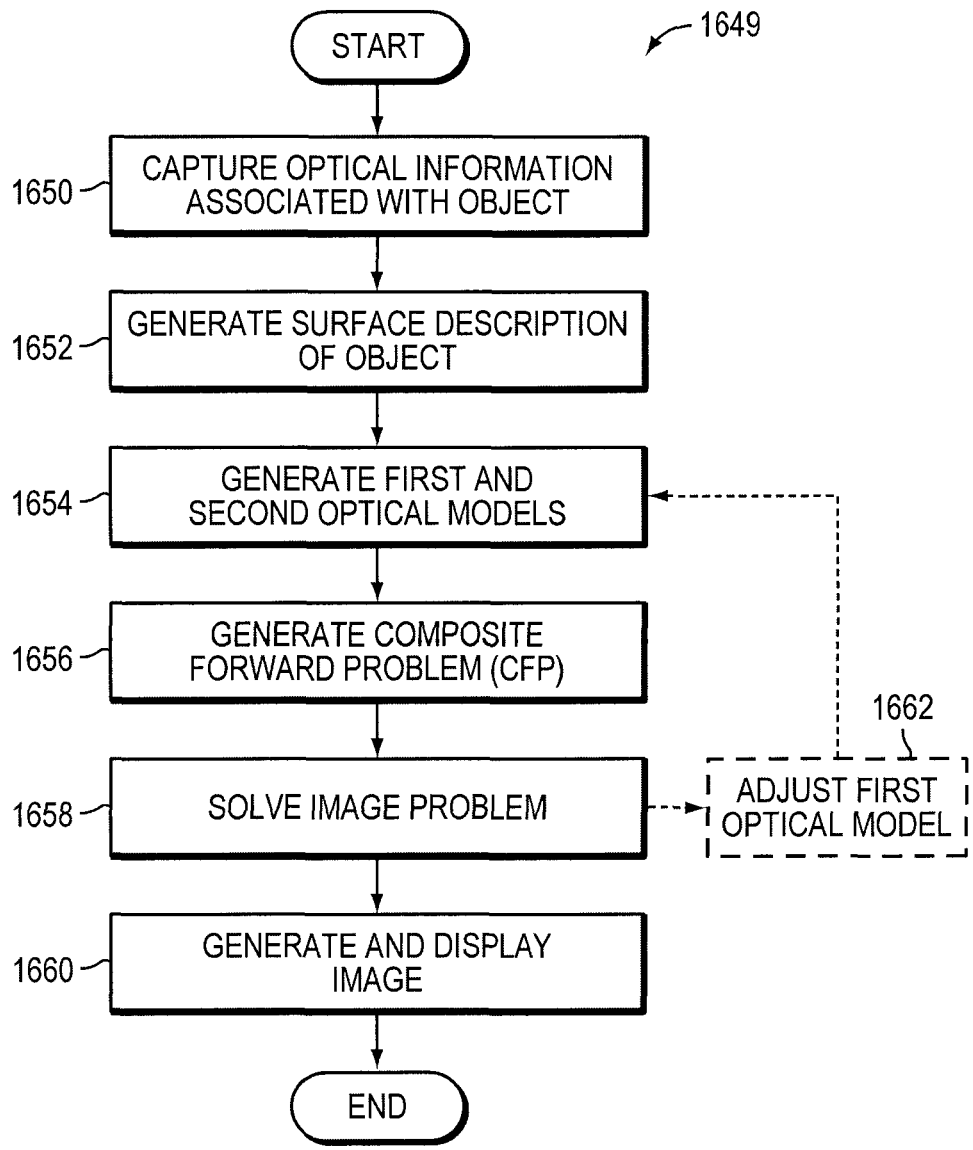
FIG. 16A is a flow chart showing a method for imaging an object with free space optical tomography, according to an illustrative embodiment of the invention.
Figure 16B:
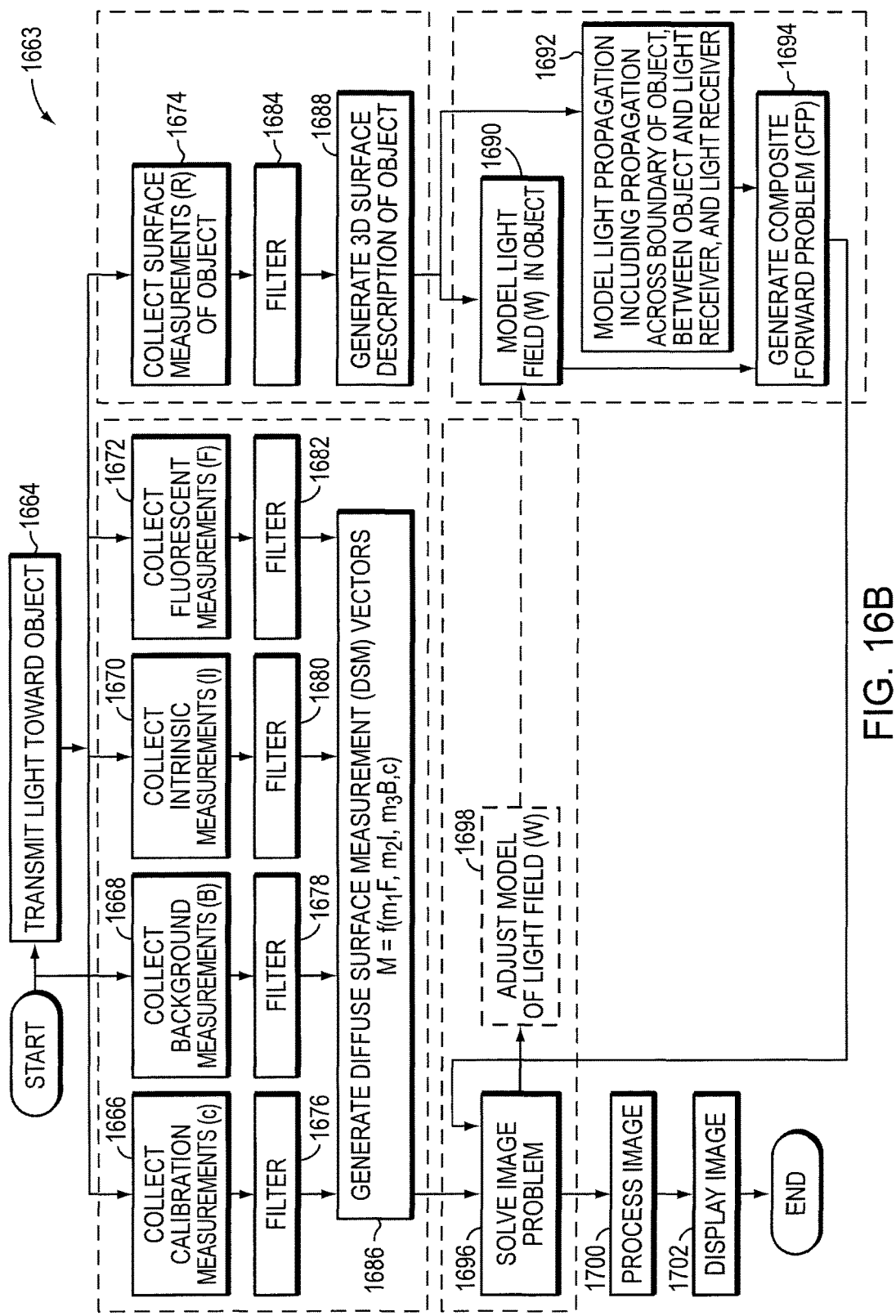
FIG. 16B is a flow chart showing further details of the method of FIG. 16A, according to an illustrative embodiment of the invention.

The solution processor 1340 is described more fully in conjunction with FIG. 16B. The one or more electrical signals provided by the data processor can correspond to measured optical data associated with the light 1316 which has propagated through the object 1318 and through free space before being collected by the one or more light sensors 1320. The one or more optical models provided by the model processor 1339 can correspond to a theoretically derived "expected" response of the one or more light sensors 1320 assuming that the object 1318 is both internally diffuse and also homogeneous, e.g., having no internal structures. Where the object 1318 does in fact have internal structures and is not internally homogeneous (for example, as is generally the case of a human body part), the solution processor 1340 is presented with an "image problem" of the form: measurements=(theoretical predictions)×(unknown distribution), where the measurements are provided by the data collection system 1312 and the theoretical predictions are provided by the surface capture system 1328 in combination with the model processor 1339. The solution processor 1340 can solve for the unknown distribution in order to establish physical positions and characteristics of the internal structures in the object 1318.

The solution processor 1340 provides an output to an image processor 1341, which in turn provides data to a display 1342. The display 1342 can provide tomographic images of the internal structures of the object 1318.

As indicated by dashed line 1338 in FIG. 13, in alternate embodiments, the solution processor 1340 processes data and optionally can provide the data to the model processor 1338. The model processor 1338 can use the data from the solution processor 1340 to adjust the one or more optical models provided by the model processor 1339 to the solution processor 1340.

Also, in certain embodiments, as indicated by dashed line 1337 in FIG. 13, data can be shared between the model processor 1339 and the data collection data processor 1324. The one or more optical models provided by the model processor 1339 can be used to adjust the electrical signals provided by data processor 1324. This alternate embodiment is described more fully in conjunction with FIGS. 17A and 17B.

The same hardware may be used to provide both the data collection system 1312 and the surface capture system 1328. For example, data collection light sources 1314 and surface light sources 1330 may be provided from the same light hardware which is controlled differently so that the light hardware provides light having different patterns (or characteristics) depending upon the intended purpose (or function) of the light hardware at a particular point in time. For example, if the light hardware were functioning as a data collection system light source 1314, the light hardware would provide light having a first pattern or characteristic appropriate for the data collection system function. However, if the same light hardware were functioning as a surface capture system light source 1330, the light hardware would provide light having a second pattern or characteristic appropriate for the surface capture system function. The light hardware may be provided, for example, as a programmable light source.

In one particular embodiment, the one or more light sources 1314, when used in the data collection system 1312, generate light in the near infrared (NIR) region and the one or more light sensors 1320 are adapted to receive the light accordingly. However, in other embodiments, the one or more light sources 1314 and the one or more light sensors 1320 are adapted to transmit and receive light having wavelengths above or below the wavelength of NIR light, including visible light and including infrared light. In one particular embodiment, light sources 1314 generate NIR light having a wavelength in the range of about 0.630 to 0.950 microns. In another particular embodiment, light sources 1314 generate IR light having a wavelength in the range of about 0.950 to 2.0 microns. In another particular embodiment, light sources 1314 generate visible light having a wavelength in the range of about 0.450 to 0.630 microns. The light provided by the one or more light sources 1314 can be at the same wavelength or a different wavelength than the light emitted by fluorophores described above. One of ordinary skill in the art will appreciate how to select a particular wavelength of light (or range of wavelengths) for a particular application.

In one particular embodiment, the one or more surface light sources 1330 generate light in the near infrared (NIR), and the one or more surface light sensors 1334 are adapted to receive the NIR light accordingly. However, in other embodiments, the surface light sources 1330 and the surface light sensors 1334 are adapted to transmit and receive light having wavelengths above or below the wavelength of NIR light, including visible light and including infrared light. In one particular embodiment, light sources 1330 generate NIR light having a wavelength in the range of about 0.630 to 0.950 microns. In another particular embodiment, light sources 1330 generate IR light having a wavelength in the range of about 0.950 to 2.0 microns. In another particular embodiment, light sources 1330 generate visible light having a wavelength in the range of about 0.450 to 0.630 microns. One of ordinary skill in the art will appreciate how to select a particular wavelength of light (or range of wavelengths) for a particular application.

In another embodiment, the one or more light sources 1314, when used in the data collection system 1312, provide continuous wave (CW) light. However, in other embodiments, the one or more light sources 1314 are modulated (e.g., in the range of Hz to kHz) or are pulsed (e.g., having pulse widths in the range of microseconds to seconds) to enable source multiplexing and/or background and ambient light separation. Corresponding light detection schemes can also be used.

In other embodiments, frequency domain sources, i.e., intensity modulated light in one or multiple frequencies (e.g., in the range of MHz to GHz) or time-domain sources, for example pulses of light having different pulse durations (for example, having pulses in the range of femtoseconds to nanoseconds) and corresponding detection systems can be used.

In still another embodiment, the one or more light sources 1314 provide a planar light source, which illuminates at least a portion of the surface of the object 1318. In another embodiment, the one or more light sources 1314 illuminate simultaneously a plurality of spots on a surface of the object. One of ordinary skill in the art will recognize that other light patterns can be also be used.

It is understood that different projection patterns, such as those described above, may also include appropriate masks or spatial attenuation patterns (not shown) to interface to the light sensors 1320, the light sensors 1320 having a dynamic range pertinent to the detection system. With a mask, for example, a stray beam of light cannot directly hit and damage or saturate the light sensors 1320.

Figure 14:
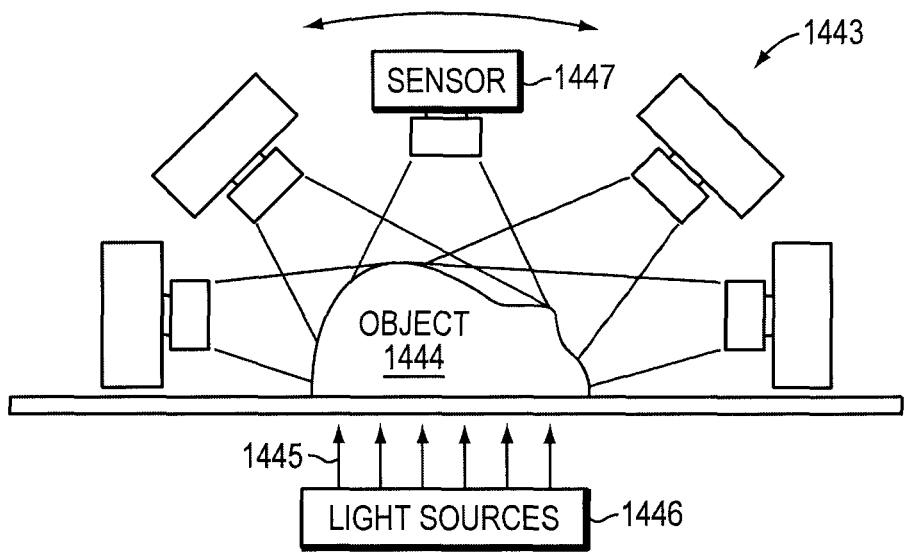
FIG. 14 is a block diagram of a portion of an exemplary free space optical tomographic system/subsystem including a light sensor and a plurality of light sources, adaptable to a single light sensor/light source pair that moves about the imaging chamber, according to an illustrative embodiment of the invention.

Referring now to FIG. 14, a portion 1443 of an exemplary tomography system includes one or more light sources 1446 to provide light 1445, which is directed at an object 1444. In this particular embodiment, the one or more light sources 1446 provide a plurality of light beams 1445. Also in this particular embodiment, the light 1445 is directed from the sources 1446 toward the object from one direction. In the exemplary embodiment of FIG. 14 the light sources 1446 are shown below the object. One or more light sensors 1447 are disposed above the object to receive the transmitted light 1445 having passed through the object 1444 and from the object 1444 through free space to the one or more light sensors 1447. In some embodiments, the one or more light sensors 1447, here shown as one light sensor 1447, may be moved to a plurality of different locations as indicated by sensors 1447 shown in phantom to receive the light 1445. For example, the light sources 1446 may direct light toward the object from above the object or beside the object in which cases the sensors 1447 may be stationary or may be moved (e.g., on a gantry), scanning the diffuse pattern of light propagating inside the object 1444 and exiting from the surface of the object 1444 at different angles. In other embodiments, a plurality of different light sensors 1447 may be disposed in particular locations above the object to receive the light 1445. It should be appreciated that the one or more light sensors 1447 can be spaced apart from a surface of the object 1444.

Figure 15:
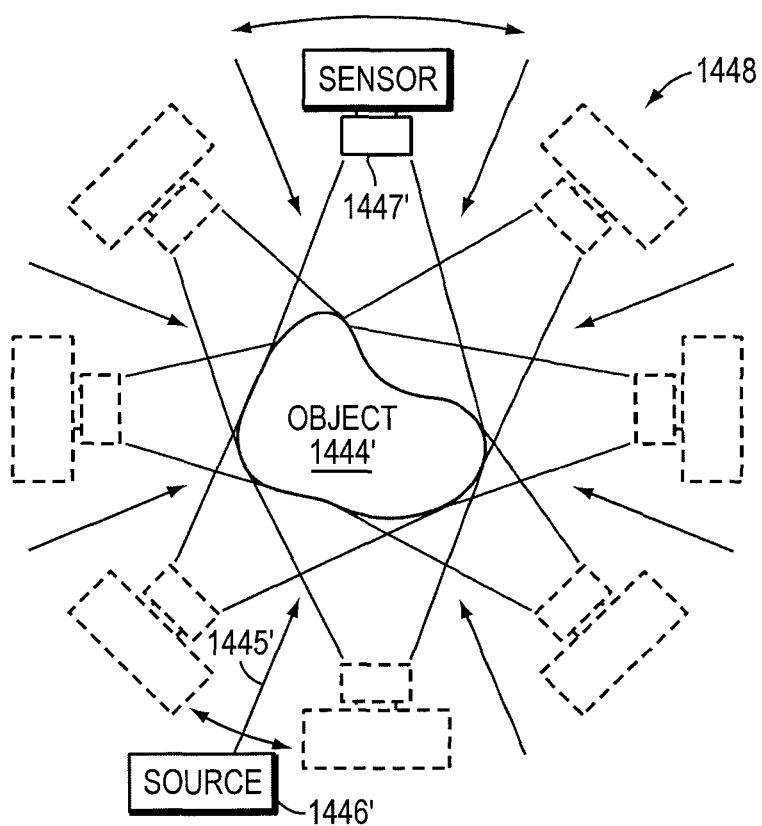
FIG. 15 is a block diagram of a portion of an exemplary free space optical tomographic system/subsystem including a plurality of light sensors and a plurality of light sources, adaptable to a single light sensor/light source pair that moves about the imaging chamber, according to an illustrative embodiment of the invention.

Referring now to FIG. 15, a portion 1448 of another exemplary optical tomography system includes one or more light sensors 1447' and one or more light sources 1446'. In one embodiment, a single light source 1446' can be moved to project light about all surfaces of an object 1444', and the sensors 1447' are appropriately positioned to receive the light 1445' having passed through the object 1444' and from the object 1444' through free space to the one or more light sensors 1447'. In other embodiments light 1445 may be provided from an array of light sources 1446' and the light sensors may be provided from an array of light sensors 1447'.

In still other embodiments, the light sources 1446', 1446 (FIG. 14) and the light sensors 1447', 1447 (FIG. 14) are disposed on substantially the same side of the object 1444', 1444 (FIG. 14). The light sources 1446', 1446 and the light sensors can be moved or sequenced in tandem or separately. Also, in yet another embodiment, only the light sensors 1447', 1447 are moved or sequenced while the light sources 1446', 1446 remain stationary.

FIGS. 16A-17B are a series of flow diagrams which describe processing performed by a system, which may be similar, for example, to the system described above in conjunction with FIG. 13, having portions such as those described in conjunction with FIGS. 14 and 15. In FIGS. 16A-17B, rectangular elements are herein denoted "processing blocks" and represent processor instructions or groups of instructions (e.g., computer programming code), which may be executed by a processing device (e.g., a personal computer, a general purpose computer or any other type of suitable processor). Diamond shaped elements, are herein denoted "decision blocks," and represent processor instructions or groups of instructions (e.g., computer programming code) which affect the execution of the instructions represented by the processing blocks.

Alternatively, the processing and decision blocks represent steps performed by functionally equivalent circuits such as a digital signal processor circuit or an application specific integrated circuit (ASIC). It should be appreciated that the flow diagrams do not depict the syntax of any particular programming language. Rather, the flow diagrams illustrate the functional information one of ordinary skill in the art requires to fabricate circuits or to generate computer software or other instruction sets needed to perform the processing required as described hereinbelow. It should be noted that many routine program elements, such as initialization of loops and variables and the use of temporary variables are not shown. It will be appreciated by those of ordinary skill in the art that unless otherwise indicated herein, the particular sequence of steps described is illustrative only and can be varied without departing from the spirit of the invention. Thus, unless otherwise stated, the steps described below are unordered meaning that, when possible, the steps can be performed in any convenient or desirable order.

Turning now to FIG. 16A, a flow diagram 1649, which illustrates an exemplary process to generate a tomographic image with a composite forward model (CFP) method begins as shown in processing block 1650 in which optical information associated with an object, for example, the object 1318 of FIG. 13, is captured. The optical information can include, for example, information provided by the light sensors 1320 and the surface light sensors 1334 of FIG. 13.

Processing then proceeds to processing block 1652 in which a surface model (e.g., a three-dimensional mathematical description) of the surface of the object image is generated. One of ordinary skill in the art will understand that there are a variety of ways to optically generate the three-dimensional mathematical description of the surface.

First and second optical models are generated as shown in processing block 1654. The first optical model describes light transmission through the object and the second optical model describes light propagation through the surface of the object, in free space about the object and characteristics of light sensors used to capture the optical information captured in processing block 1650.

At processing block 1656, a composite forward problem (CFP) is generated as a combination of the first and second optical models provided in processing block 1654. The CFP and optical information associated with the object are used to solve an image problem as shown in processing block 1658. As described above, the image problem can have the form: measurements=(theoretical predictions)×(unknown distribution), where the measurements are provided from processing block 1650 and the theoretical predictions are provided by the first and second optical models at processing block 1654. Solution of the image problem is further described below in conjunction with FIG. 16B.

Optionally, processing may proceed to processing block 1662 in which the first optical model is adjusted and processing blocks 1654, 1656, and 1658 are repeated. Once the image problem is solved, processing flows to processing block 1660 where a tomographic image is generated in displayed.

Referring now to FIG. 16B, an exemplary process 1663 for generating a tomographic image using a composite for a problem (CFP) approach begins by collecting a series of measurements as shown in processing blocks 1666-1674. In particular, calibration measurements, c, are collected in processing block 1666, background measurements, B, are collected in processing block 1668, intrinsic measurements, I, are collected in processing block 1670, fluorescent measurements, F, are collected in processing block 1672, and surface measurements, R, of the object are collected in processing block 1674. While the data collected at processing blocks 1666, 1670, 1672, and 1674 is collected in the presence of light generated at processing block 1664, which is directed toward the object, the background measurements collected at processing block 1668 can be collected in the absence of the light generated at the processing block 1664.

Calibration measurements can be collected at block 1666, where the object, for example the object 1318 of FIG. 13, can be replaced with an object having known characteristics. For example, the object can be replaced with an object having a homogeneous internal structure without internal structures. For another example, the object can be replaced with an object having known internal structures. The calibration measurements thus obtained can be compared later in the process 1663 with tomographic images generated for the calibration object and the process 1663 can be adjusted accordingly. The calibration measurements can be collected, for example, with the light sensors 1320 of FIG. 13.

Background measurements can be collected in processing block 1668 in order to record ambient light in the absence of the light transmitted at step 1664. Background light signals, corresponding to the background light can be subtracted or otherwise cancelled from subsequent measurements in which with light is transmitted at processing block 1664, including from the calibration measurements obtained at processing block 1666. The background measurements can be collected, for example, with the light sensors 1320 of FIG. 13.

Intrinsic measurements collected at processing block 1670 can include measurements of the light that is generated at processing block 1664, the light having passed through the object and having propagated in free space adjacent to the object 1318. The intrinsic measurements can be collected, for example, with the light sensors 1320 of FIG. 13.

Fluorescent measurements collected at processing block 1672 can include measurements of fluorescent light generated by fluorochromes from within the object, such as that described in conjunction with FIG. 13. The fluorescent measurements can be collected, for example, with the light sensors 1320 of FIG. 13, with or without the presence of the light transmitted at the processing block 1664.

Surface measurements collected at processing block 1674 can include measurements of light patterns generated at processing block 1664. The surface measurements can be collected, for example, with the surface light sensors 1334 of FIG. 13. However, as described above in conjunction with FIG. 13, in other embodiments, the surface measurements can be collected with the light sensors 1320 of FIG. 13.

Each of the measurements collected at processing blocks 1666-1674 are then appropriately digitized and filtered as shown in processing blocks 1676-1684. The data or the information measured in processing blocks 1666-1672 can be used to generate composite measurement vectors, M, as shown in processing block 1686, which can have the form $M=f(m_1 F, m_2 I, m_3 B, c)$, where $m_1$, $m_2$, and $m_3$ are coefficient, any of which can be zero.

Similarly, the surface measurements of the object having been appropriately digitized and filtered at processing block 1684 are used to generate a surface model (e.g., a three-dimensional (3D) mathematical description) of a surface the object as shown in processing block 1688. The three-dimensional surface description of the object is then used to provide a first optical model at processing block 1690 as a model of a light field in an object having a shape as described by the three-dimensional surface description. The first optical model can assume an object having the shape of the actual object to be imaged, the shape provided by the three-dimensional surface description, and it can assume an object diffuse to the propagation of light like the actual object. However, as described above, the first optical model can assume that the object is homogeneous, having no internal structures.

As described above, even for a homogeneous object, light does not propagate in straight lines when passing through an object, which is diffuse to the propagation of the light. A variety of techniques can provide, as the first optical model, a model of the light field in a diffuse object. For example, analytical solutions of the diffusion equations can be used based on Green's function solutions of homogeneous media, combined with first or high-order reflections from the surface elements as when using the Kirchoff approximation or the boundary element method. The Green's function solutions can be updated iteratively or, can use a-priori information to represent solutions that model heterogeneous media as well.

In one embodiment, the first optical model can be calculated based on analytical methods, for example the Born or Rytov approximation. However different light field models of light in the diffuse medium based on analytical or numerical methods can also be used.

The three-dimensional surface description of the object provided at the processing block 1688 is also used at processing block 1692 to provide a second optical model, including, but not limited to, a model of light propagation through the boundary of the surface of the object, a model of light propagation between the object and light receiver, and a model of characteristics of the light receiver. The second optical model is further described in conjunction with FIGS. 16B and 18A-19F.

The first and second optical models are then combined to generate a composite forward problem (CFP) as shown in processing block 1694. The CFP can be used to predict the output of the light sensors, for example the light sensors 1320 of FIG. 13, when the object being scanned is homogeneous and has no internal structures. However, when the tomographic imaging system 1663 is used to scan an object that is not homogeneous or which has internal structures, the measurements collected at the processing block 1670 will generally not agree with the prediction made by the CFP.

The composite forward problem and the composite measurement vectors are then used to solve the image problem as shown in block 1696. As described above, the image problem can have the form: measurements=(theoretical predictions)×(unknown distribution), where the measurements are provided at processing block 1686 and the theoretical predictions are provided as the CFP at processing block 1694, and where the unknown distribution correspond to internal structures in the object. As described above, measurements can also be written as composite measurement vectors $M=f(m_1 F, m_2 I, m_3 B, c)$, where $m_1$, $m_2$, $m_3$ are coefficients, which may take zero value.

The first optical model generated at the processing block 1690 corresponds to a light field description, W. The second optical model generated at the processing block 1692 corresponds to an operator, T, associated with models of the propagation of light passing through a surface of the object, propagation of the light in free space between the object and the light sensors, and characteristics of the light sensors. The three-dimensional surface description of the object generated at the processing block 1688 corresponds to a description, S, of the object surface having a data set, R. The unknown distribution of optical properties described above, i.e., structures in the diffuse object, can be written as a factor, X, corresponding to the unknown distribution above. The image problem, therefore, can be written to relate M to X as $M=f(m_1 F, m_2 I, m_3 B, c)=q(W(S), T(S), X(S))$, or in the more general form as $M=g(W'(S), X, S)$ where q, g are appropriate functions that relate the measurements to theoretical predictions and W'(S) is a forward descriptor that incorporates light propagation in diffuse and non-diffuse media. The functions q or g may be analytical or discrete. In one embodiment described below, M can be also written as $$M=T(S)*W(S)*X(S).$$

In order to solve the image problem, and in particular to solve for the unknown distribution, X, the unknown distribution, X, can be minimized, for example, by an iterative solution to the image problem. By another solution method, the function, g, can be inverted to extract the unknown distribution, X, from the set of measurements, M. Other methods can also be used.

Figure 17A:
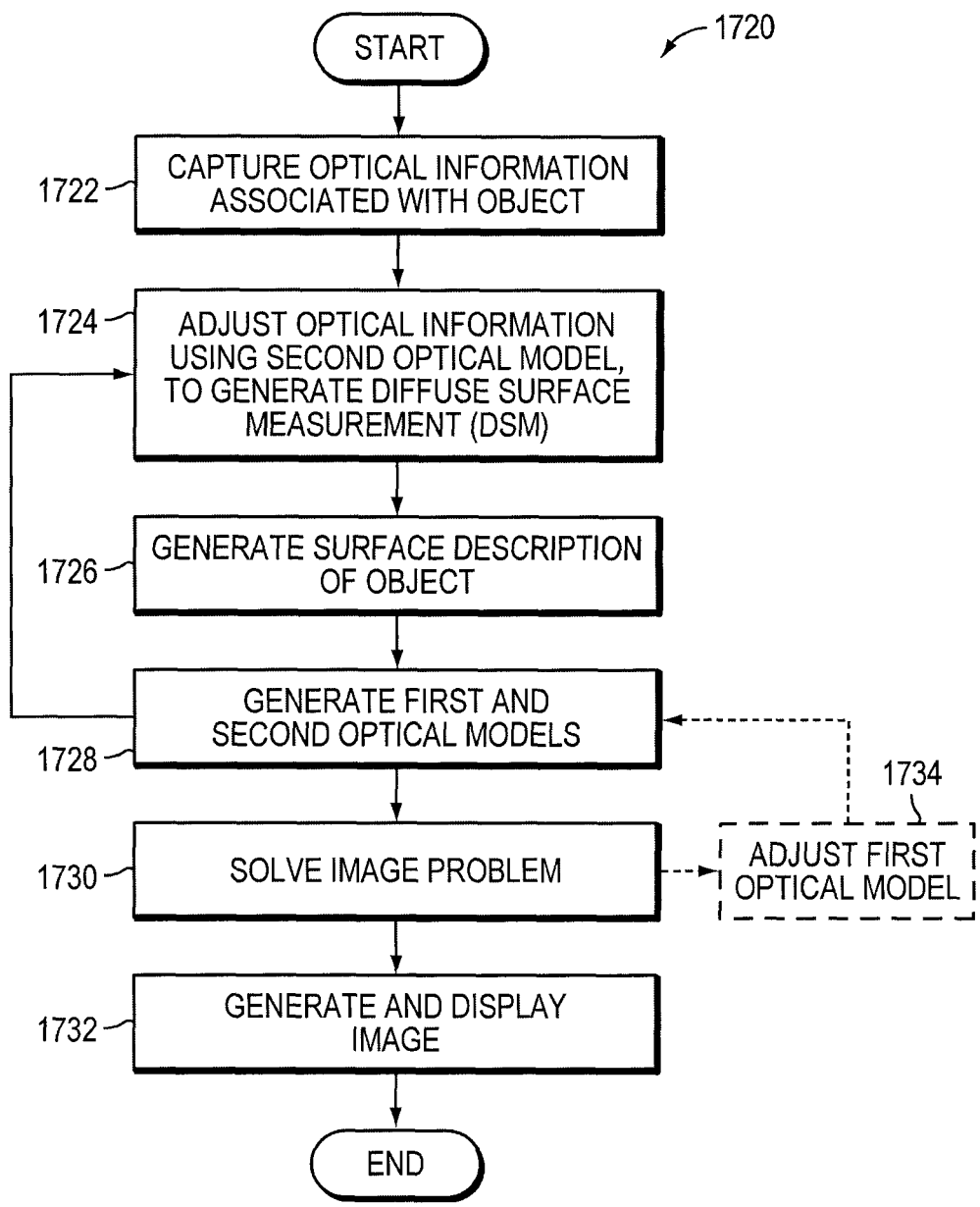
FIG. 17A is a flow chart showing a method for imaging an object with free space optical tomography, according to an illustrative embodiment of the invention.
Figure 17B:
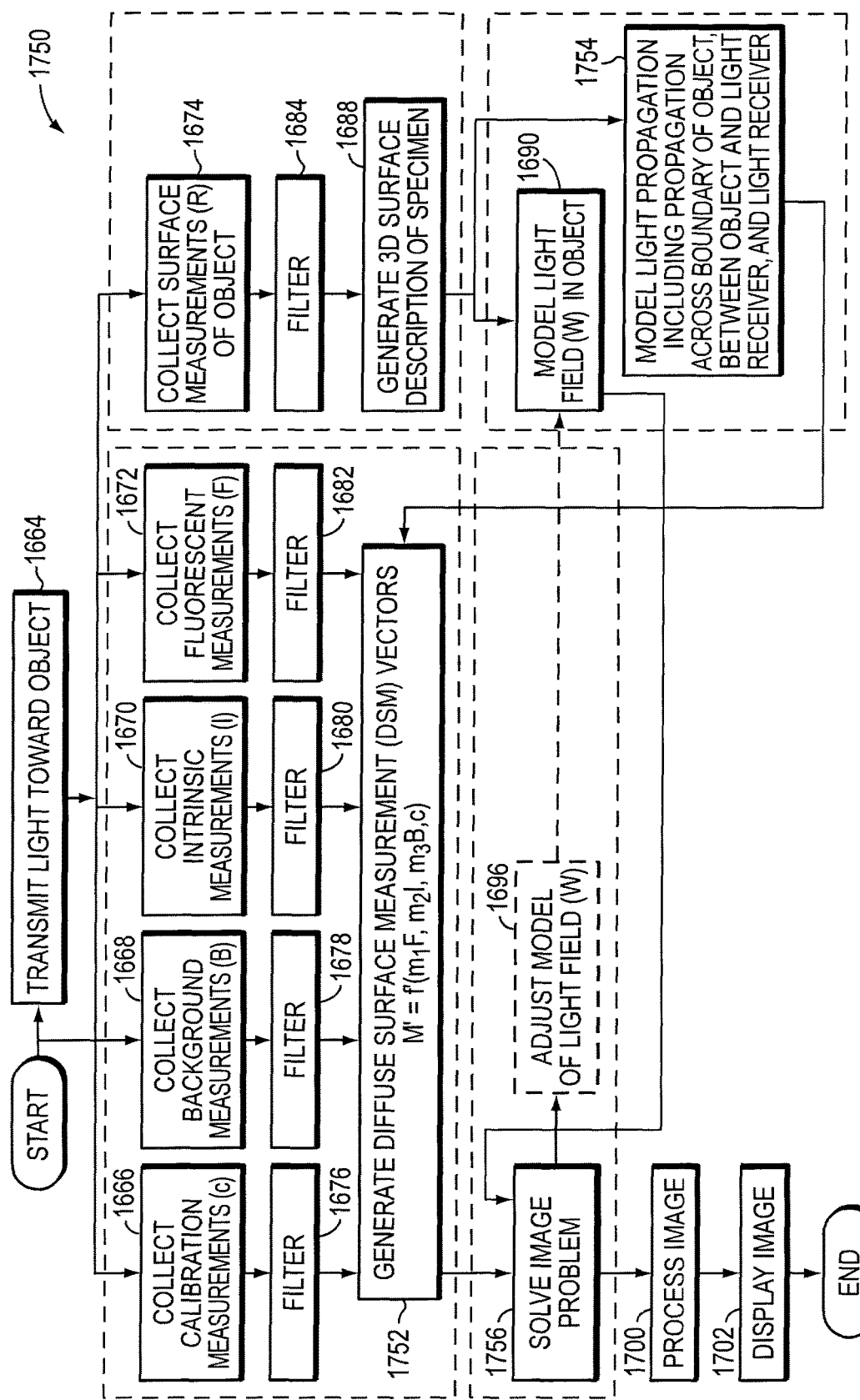
FIG. 17B is a flow chart showing further details of the method of FIG. 17A, according to an illustrative embodiment of the invention.

In the CFP method 1663, both T and W or W'(s) can be determined theoretically as first and second optical models at processing blocks 1690 and 1692, whereas measurement vectors, M, can include measured values provided at the processing clock 1686. However, M, in another method, referred to as a diffuse surface measurement (DSM) method described in conjunction with FIGS. 17A and 17B, provides that measurement vectors, M, can be adjusted with theoretical predictions as well (i.e., the measurement vectors, M, are scaled by a theoretical calculated function or constant associated with an optical model). Similarly, in other embodiments, the operators T, W or W'(s), associated with the first and/or the second optical models, can be experimentally determined.

Optionally, the model of the light field may be adjusted at processing block 1698 and processing blocks 1690, 1692, and 1694 may be repeated. Once the image problem is solved at the processing block 1696, processing flows to processing block 1700 where the image is processed tomographically, and to processing block 1702 where the tomographic image is displayed.

The composite measurement vectors, M, provided at processing block 1686 are associated with measurements taken with a variety of relative angles between light sources and light sensors, in order to provide tomographic image processing at processing block 1700.

As described above, in one embodiment, the first optical model generated at block 1690 and used to calculate the light field, W, in the object can be calculated based on analytical methods, for example the Born or Rytov approximation. However, in other embodiments, the first optical model of the light field in the object can be based upon other analytical or numerical methods.

To provide the second optical model at block 1692, a light source can be considered, at position, $r_s$ emitting light of wavelength, $\lambda_1$, creating an average intensity, $U_0$, within an arbitrarily shaped diffuse volume, V, of average absorption coefficient, $\mu_a$, and reduced scattering coefficient, $\mu_s'$. The normalized Born intensity U, (in either absorption/scattering or fluorescence mode) is measured by a light sensor at position $r_d \in V$, also within the volume. It is given by:

$$U(r_s, r_d) = \frac{U_1(r_s, r_d, k_1) - qU_0(r_s, r_d, k_0) - p}{U_2(r_s, r_d, k_2)} = \quad (21)$$
$$A_0 \cdot U_3(r_s, r_d, k_1)^{-1} \int d^3r[U_4(r_s, r, k_1)O(r)G(r_d, r, k_2)]$$

$U_1$, $U_2$ are two diffuse photon fields measured experimentally. For example, in fluorescence tomography, $U_1$, is the fluorescence field and $U_2$ is the field measured at the excitation wavelength. In either absorption tomography or fluorescence tomography, $U_2$ and $U_1$ can be a photon field measured before and after the administration of a contrast agent respectively. Or, $U_2$ can be a calibration field measured in a calibration phantom. For different cases, the theoretically calculated fields, $U_3$ and $U_4$, can be correspondingly calculated according to an assumption that $U_1$, $U_2$ are the Green's function solutions from the source to the detector, $r_d$, or to a voxel, r, respectively. $U_0$ is a background field, which can be turned off or subtracted proportionally to the coefficient q. This field represents the bleed through signal in fluorescence tomography (i.e., $U_2 = U_0$ and q is the bleed through coefficient of the filters used). Finally p is an "offset" field typically representing some offset in the data due to detection associated offsets or DC levels. The photon propagation wave numbers $k_1 = (-\mu_{a1}|D_1)^{1/2}$, $k_2 = (-V\mu_{a2}|D_2)^{1/2}$ are identical in absorption (k1=k2) and reflect the wave numbers at excitation and emission wavelengths $\lambda_1$, $\lambda_2$ respectively if fluorescence measurements are considered. The factors $\mu_{a1}$, $\mu_{a2}$, and $D_1 = (3\mu'_{s1})^{-1}$, $d_2 = (3\mu'_{s2})^{-1}$ are absorption coefficients and diffusion coefficients, respectively. The factor, G, is the system's Green function, which describes light propagation from a unit point source to a light sensor and can be written for homogeneous or heterogeneous media. The function O(r) is the unknown quantity reconstructed (this being the unknown scattering, absorption of fluorochrome mass) and $A_0$ is a multiplicative factor associated with system gain factors and light propagation constants such as the speed of light. The equation is actually written assuming constant or invariable (known) scattering coefficient throughout the medium but can be expanded straightforwardly to include scattering inhomogeneities as well. For simplicity, similar light propagation characteristics, e.g., $k_1 \approx k_2$ and $D_1 \approx D_2$ can be assumed, which is a valid assumption when considering the absorption scattering problem and is also a valid assumption for fluorescence measurements when there is no significant change in tissue optical properties between $\lambda_1$ and $\lambda_2$, which can be true especially for dyes in the NIR due to the relatively flat absorption spectrum of tissue in this spectral region. This approximation is done herein for simplification and the methodology works identically if different tissue optical properties are considered for $\lambda_1$ and $\lambda_2$. Furthermore, the diffusion coefficient, D, is considered to be independent of the absorption coefficient, an approximation generally valid in the NIR region.

While it may be computationally costly to calculate an accurate Green's function for arbitrary boundaries with numerical methods, the Kirchhoff approximation (KA) has been shown to be a time-efficient approach.

In a first assumption, a surface is discretely partitioned into N plane facets, each one having an area, $\Delta S_b$, and a surface normal, $n_b$. In free space embodiments, it is assumed light sensors are at positions located outside of the object and in a non-diffusive medium (typically air) where light propagation can be modeled as straight rays instead of diffuse waves. Therefore, a transformation can be determined that describes the contribution of the surface points onto a certain light sensor, where light sensors are described as triples, e.g., $d=(r_d, n_d, A_d)$ having position, $r_d$ detector normal vector, $n_d$, and aperture, $A_d$.

In order to generate the above transformation, a variety of optical considerations are presented in FIGS. 18A-19F below. First, the diffuse surface measurement (DSM) method described above, which also generates the first and second optical models, is further described below in conjunction with FIGS. 17A and 17B.

Referring now to FIG. 17A, a flow diagram 1720, which illustrates an exemplary process for generating a tomographic image with a diffuse surface measurement (DSM) technique begins as shown at processing block 1722 in which optical information associated with an object, for example, the object 1318 of FIG. 13, is captured. The optical information can include, for example, information provided by the light sensors 1320 and the surface light sensors 1334 of FIG. 13. The processing performed at block 1722 can be the same as or similar to the processing performed at block 1650 of FIG. 16A.

Processing then proceeds to processing block 1724, in which a portion of the optical information collected at block 1722 is adjusted to provide altered measured data referred to herein as diffuse surface measurements (DSMs). The measured data can be altered in conjunction with the first optical model as described below.

Processing then proceeds to processing block 1726, in which a surface model (e.g., a three-dimensional mathematical description) of the surface of the object image is generated. There are a variety of ways to optically generate the three-dimensional mathematical description of the surface. The processing performed at block 1726 can be the same as or similar to the processing performed at block 1652 of FIG. 16A.

The first and second optical models are generated as shown in processing block 1728, the first optical model to describe light transmission through the object, and the second optical model to describe light propagation through the surface of the object, in free space about the object, and to describe characteristics of light sensors used to capture the optical information at block 1722. The first optical model can be used to adjust the measured data at block 1724 to provide the DSM. The first and second optical models can be the same as or similar to the optical models generated at block 1654 of FIG. 16A.

At processing block 1730, an image problem is solved. The image problem used in the DSM method 1720 can have the form: diffuse surface measurements=(theoretical predictions)×(unknown distribution), where the altered measurements are provided at processing block 1724 and the theoretical predictions are provided by the first and second optical models at block 1728. This image problem is similar to the image problem described in conjunction with processing block 1658 of FIG. 16A, and can be solved using the same numerical methods. Solution of the image problem is further described above in conjunction with FIG. 17B.

Optionally, processing may proceed to processing block 1734 in which the first optical model is adjusted in accordance with the image problem and processing blocks 1728 and 1730 are repeated. Once the image problem is solved, processing flows to processing block 1732 where a tomographic image is generated in displayed.

Referring now to FIG. 17B, in which like elements of FIG. 16B are shown having like reference designations, a DSM method is shown to have many processing blocks which are the same as or similar to processing blocks of the CFP method of FIG. 16B. Here, however, the processing blocks 1752-1756 can be different.

At processing block 1752, diffuse surface measurements (DSM) vectors are generated, which can have the form $M'=f'(m_1F, m_2I, m_3B, c)$, where $m_1$, $m_2$, and $m_3$ are coefficients. The DSM vectors are adjusted versions of the composite measurement vectors, which have the form $M=f(m_1F, m_2I, m_3B, c)$ generated at block 1686 of FIG. 16B. From analysis above presented in conjunction with FIG. 16B, the composite measurement vectors represent actual measurements of light collected at blocks 1666-1672. The composite measurement vectors are used in an image problem at block 1696 of FIG. 16B in order to solve for the unknown distribution, which corresponds to internal structures in the object. In the DSM method 1750 however, the image problem solved at processing block 1756 receives the diffuse measurement vectors instead of the composite measurement vectors.

To provide the diffuse surface measurements at processing block 1752, the second optical model 1754 or portions of the second model 1754 can provide model information to the processing performed at processing block 1752. The model information provided for this purpose essentially moves the measurements collected at one or more of the processing blocks 1666-1672 by the light sensors at a reference position apart from the object to a new reference position on the object, as if the measurements had been collected by light sensors on the surface of the object. Therefore, the DSM vectors correspond to calculated measurements of the light as if the measurements had been collected by light sensors on the surface of the object.

At processing block 1756 the image problem is solved, having the form: diffuse surface measurements=(theoretical predictions)×(unknown distribution). This form has the same form as that described above for the CFP method of FIGS. 16A and 16B, and can be solved using the same methods.

Figure 18A:
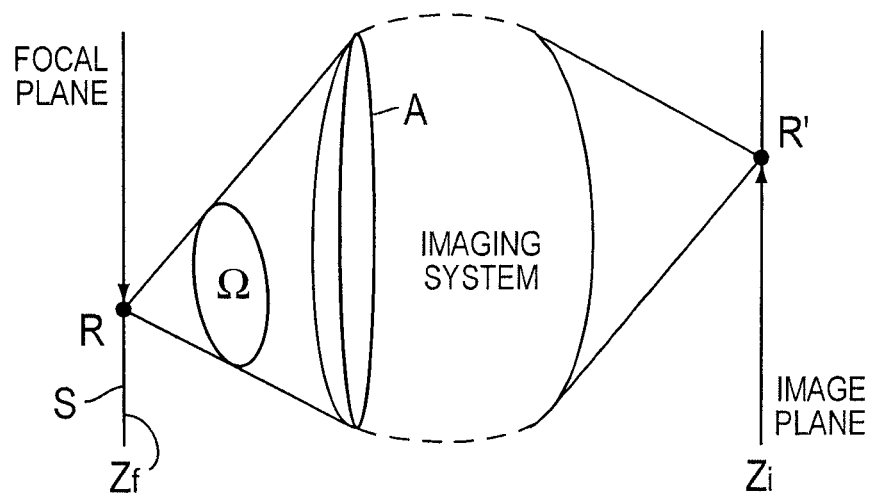
FIG. 18A is a diagram depicting an in-focus imaging system used in the free space optical tomography system/subsystem of FIG. 13, according to an illustrative embodiment of the invention.

Referring now to FIG. 18A, an imaging system having an aperture, A, corresponding to a solid angle, $\Omega$, generates an image point, R', of a point R lying on a surface, S. Here, the surface, S, is a planar surface lying coincident with a focal plane, $Z_f$, associated with the imaging system. The image point, R', lies on an image plane, $Z_i$, and the point, R, lies on the focal plane, $Z_f$. Assuming an ideal imaging system, which has a one-to-one correspondence between the points, R and R', for those angles that fall within an aperture, A, of the imaging system, $$F(R')|_{z=z_i} = G(R)|_{z=z_f}$$

where it is assumed that $R'|_{z=z_i} \Leftrightarrow MR|_{z=z_f}$, M being a magnification factor.

The relation between the image at the point, R, that enters the aperture, A, and the image at the image point, R', is: $F(R')=\gamma F(MR)$ where $\gamma$ is the overall gain factor (<1). Hereafter, the terms R and R' may be used interchangeably, bearing in mind that their relationship is R'=MR when used together. Power that goes through the imaging system is represented by:

$$P(R')|_{z=z_i} = \gamma P(MR)|_{z=z_f} \qquad (22)$$

The "stop," (for example, f-stop in conventional photography) of the imaging system is defined by the smallest aperture at an entrance to the imaging system. The aperture, A, having an area also denoted as A, delimits the angle of acceptance of the imaging system.

Figure 18B:
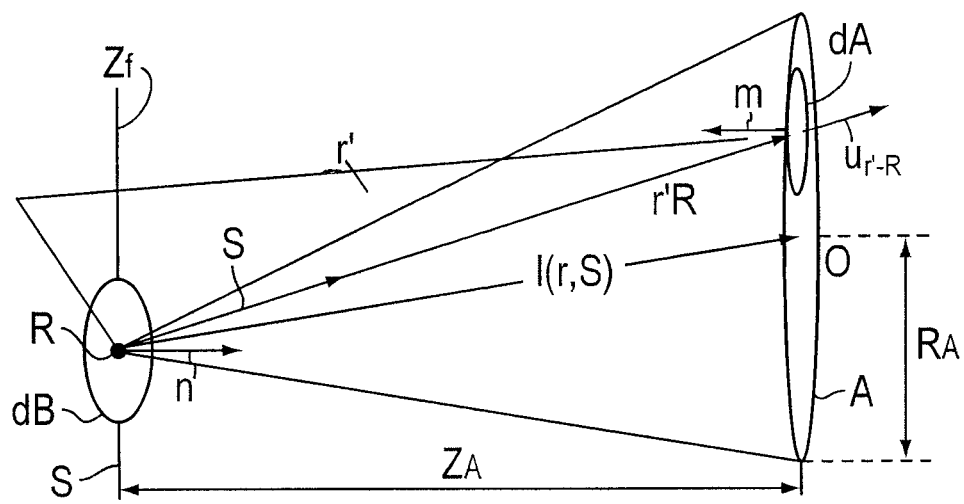
FIG. 18B is a diagram depicting an in-focus imaging system used in the free space optical tomography system/subsystem of FIG. 13, according to an illustrative embodiment of the invention.

Referring now to FIG. 18B, in which like elements of FIG. 18A are shown having like reference designations, the plane, S, having the point R, again is coincident with the focal plane, $Z_f$, of the imaging system. Therefore, the point, R is in focus in the imaging system (FIG. 18A). Here, however, the image plane, $Z_i$, of FIG. 18A is not explicitly shown. Instead, the aperture, A, corresponds to an aperture provided within the imaging system of FIG. 18A, and in front of (to the left of) the image plane of FIG. 18A.

As described above, the planar surface, S, is located exactly at the focal plane, $Z_f$. The planar surface, S, includes a differential surface area, dB, about the point, R. The differential surface area, dB, is shown having a differential surface normal, n. The differential surface area, dB, about the point, R, is associated with a differential surface area, dA, at the aperture, A. The differential surface area, dA, is shown having a differential surface normal, m. A distance, $Z_A$, corresponds to a distance from the focal plane, $Z_f$, to the aperture, A. The differential surface area, dB, is also shown having a vector, s, in a direction of the differential surface area, dA, and the differential surface area, dA, is shown having a vector, $u_{r'-R}$, in a parallel direction, each corresponding to an intensity of light passing through the respective differential surface area. The aperture, A, can be off-axis with respect to the differential surface normal, n, or it can be on-axis. A vector, r', represents a point corresponding to the point, R, but at the differential surface area dA. A vector, O, represents the center of the aperture having area, A.

A total power measured at the image point, R' (FIG. 18A), due to the differential surface area, dB, is equivalent to the total power, P, at the point, R, (for example, in Watts) irradiated into the solid angle, $\Omega$ (FIG. 18A):

$$P(R) = \int_\Omega I(r, s) n \cdot s dB d\Omega, \quad \forall s \in \Omega \qquad (23)$$

where the vector, n, is the differential surface normal to the differential surface area dB, and I(r,s) represents the amount of power that at point r flows within a certain solid angle defined by unit vector s for each existing wavelength. I(r,s) is referred to as the specific intensity. I(r,s) is shown in FIG. 18B.

Due to the relationship between r' and the point, R, the differential surface area, dB, may be seen as a "detector area" at the image plane (FIG. 18A). In other words, the differential surface area, dB, represents an image of the detector area at the focal plane, $Z_f$. The solid angle, $\Omega$, (FIG. 18A) corresponds to the aperture, A, (i.e., the entrance pupil, lens, etc.) and to the point, R. In order to solve Equation (23) it is most convenient to write this solid angle, $\Omega$, in terms of the differential surface area, dA, at the aperture, A, as:

$$d\Omega = \frac{m \cdot u_{R-r'}}{|r' - R|^2} dA \qquad (24)$$

where m is the differential surface normal at the aperture, A, and where $$u_{r'-R} = (r'-R)/|r'-R|,$$

where r' is the vector that defines a point in the aperture, A. By using equation (24), the total power radiated by the differential surface area, dB, is:

$$P(R) = \int_A I(R, u_{r'-R})(n \cdot u_{r'-R}) \frac{(m \cdot u_{R-r'})}{|r'-R|^2} dB dA, \qquad (25)$$

where the integration is performed over the area of the aperture, A.

If the aperture, A, has a radius, $R_A$, then:

$$dA = 2\pi R_A dR_A \text{ and}$$

$$|r'| = \sqrt{Z_A^2 + R_A^2},$$

where $Z_A$ is a distance from the focal plane ($Z_f$) to the aperture, A.

Equation (25) represents the exact solution within the Radiative Transfer formulation for the power, P(R'), (by using Equation (22) measured by a light sensor corresponding to the differential surface area, dB', (dB'$\leq$M$^2$dB), where the prime symbol indicates that the differential surface area dB is the detector area measures at the imaging plane.

Using the above equations, in conjunction with FIG. 18C below, two case are considered: a) when the area of the aperture is small ($Z_A \gg R_A$), and b) when the area of the aperture is very large ($Z_A \ll R_A$). Below, in conjunction with FIG. 18D, an isotropic light source is considered.

Figure 18C:
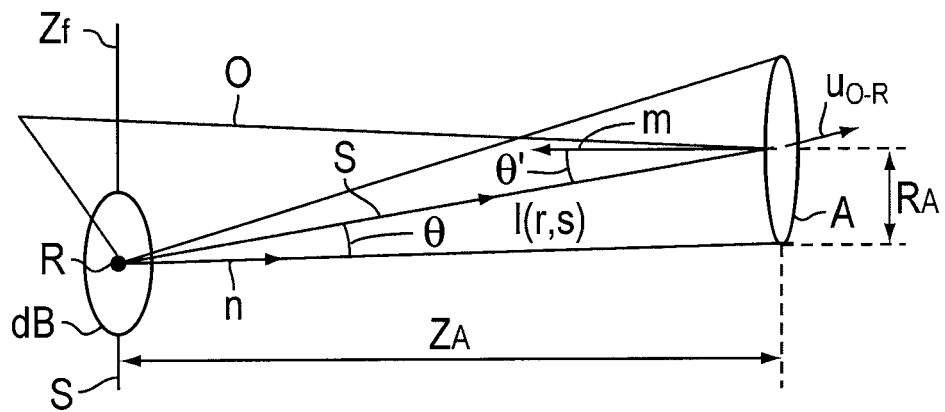
FIG. 18C is a diagram depicting the in-focus imaging system of FIG. 18A having a small aperture and having a large aperture, according to an illustrative embodiment of the invention.

Referring now to FIG. 18C, in which like elements of FIGS. 18A and 18B are shown having like reference designations, a small aperture, A, is shown, where the vector, O, represents a center of the aperture, A. Again, the point, R, is in focus in the imaging system (FIG. 18A).

For a small aperture, A, where $Z_A \gg R_A$, the angular dependence in the integral of Equation (25) may be approximated to be a constant, yielding:

$$P(R) = I(R, u_{O-R}) \cos\theta \frac{\cos\theta'}{|O - R|^2} A dB \qquad (26)$$

where O is the vector that represents the center of the aperture, A, and where, $$\cos\theta = n \cdot u_{O-R}, \text{ and } \cos\theta' = m \cdot u_{R-O},$$

where $\theta$ is the angle between the normal, n, of the differential surface area, dB, and the unit vector pointing from O towards R, and $\theta'$ is the angle between the surface normal, m, of aperture area, A, and the unit vector pointing from R towards O.

The above approximation is equivalent, for example, to a light fiber having the aperture, A, and surface normal, m, located a distance, O–R, from a radiating source. As an example, the case can be considered in which the surface normals, m and n, are parallel (as in the case when a planar surface is imaged), and where the differential surface area, dB, radiates as a Lambertian source, I(R,s)=I$_0$(R). In this case the power measured at the point, R, is:

$$P(R) = I_0(R) \cos^2\theta \frac{A}{r^2} dB \qquad (27)$$

where r=|r–O| is the distance between the points defined by r and O.

For a large aperture, where $Z_A \ll R_A$, most or all light flux that leaves the differential surface area dB will be detected. That is, the detected power at the point, R' (FIG. 18A), is equal to the total power emitted from the differential surface area, dB, and:

$$P(R) = \int_{(2\pi)^+} I(R, s)(n \cdot s) dB d\Omega = J_n^+(R) dB \qquad (28)$$

where $J_n^+$ is the total flux [e.g., in Watts/cm$^2$] that traverses the differential surface area, dB, from right to left as shown.

Equation (28) is general for any angular dependence of light radiated from the image plane, i.e., from the surface, S. For a large aperture, no angular dependence introduced due to geometrical considerations is expected in the image plane as long as the surface normals, m and n, are parallel. Also, for a large aperture, the in focal plane, $Z_f$, may be seen as a collection of virtual light sensors (e.g., optical fibers) each having a differential surface area, dB, and each in contact with the surface, S. In the case where the surface normals, m and n, are not parallel, the solid angle integral of the above equation will not be in the whole hemisphere $(2\pi)^+$ and an angular dependence will appear.

Figure 18D:
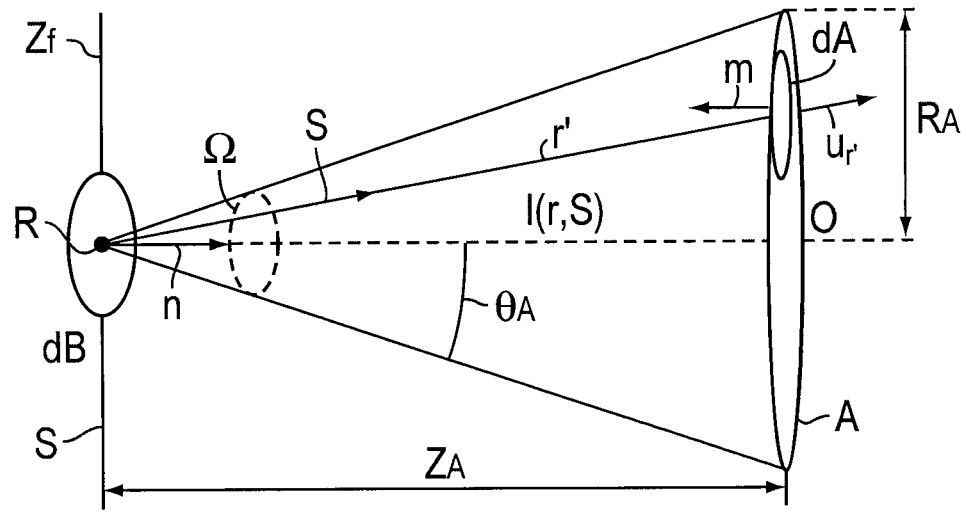
FIG. 18D is a diagram depicting the free space optical tomography system/subsystem of FIG. 13 having an isotropic light source, according to an illustrative embodiment of the invention.

Referring now to FIG. 18D, in which like elements of FIGS. 18A-18C are shown having like reference designations, again, the point, R, is in focus in the imaging system (FIG. 18A).

In order to illustrate application of the expressions derived above in conjunction with FIG. 18C obtained for large and small apertures, a special case is shown and considered where an arbitrary aperture, A, is on-axis with the differential surface area, dB. In this case, the total detected power is equivalent to:

$$P(r) = 2\pi \int_\Omega I(r,s)\cos\theta dBd(\cos\theta) \qquad (29)$$

where the solid angle, $\Omega$, (FIG. 18A) is represented by $d\Omega=d\phi \sin\theta d\theta$. The limits of integration are $\cos\theta \in \{\cos\theta_A, 1\}$, where $\cos\theta_A = Z_A/\sqrt{Z_A^2 + R_A^2}$. Assuming an isotropic source, $I(r,s)=I_0$, Equation (29) can be solved to give:

$$P(r) = \pi I_0 dB(1 - \cos^2\theta_A) \qquad (30)$$

and therefore, $$P(r) = \pi I_0 dB \frac{R_A^2}{Z_A^2 + R_A^2} \qquad (31)$$

When dealing with the Lambertian approximation, it is shown above that the total outward flux (i.e., from right to left), $J_n^+$, is related to the specific intensity as $I_0=J_n^+/\pi$. Therefore, when $Z_A \ll R_A$, equation (31) is equivalent to equation (28). Also, since an area, A, of the aperture, A, is $A=\pi R_A^2$, equation (31) can be written as $P(r)=I_0 AdB/(Z_A^2 + R_A^2)$. In the case where $Z_A \gg R_A$ this reduces to $P(r) \approx I_0 AdB/Z_A^2$, thus recovering Equation (27) for the on-axis case.

Figure 19A:
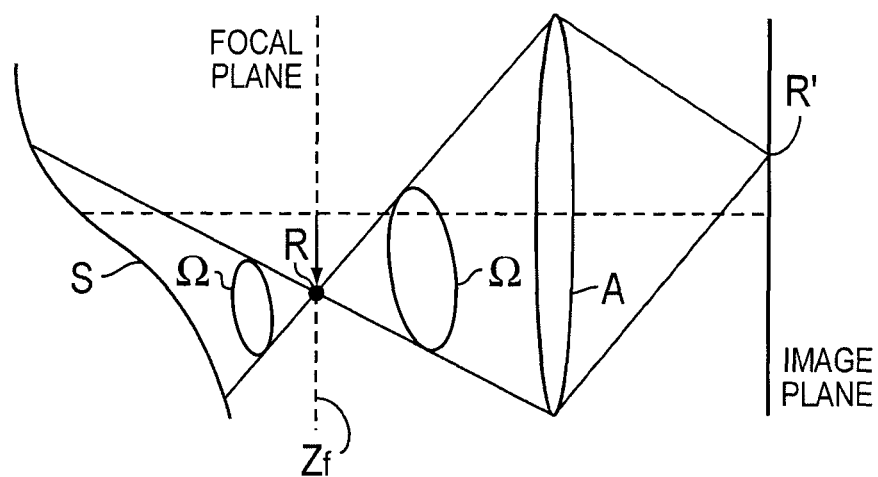
FIGS. 19A-19F are diagrams depicting out-of-focus surface contributions received by a light sensor used in the free space optical tomography system/subsystem of FIG. 13, according to an illustrative embodiment of the invention.
Figure 19B:
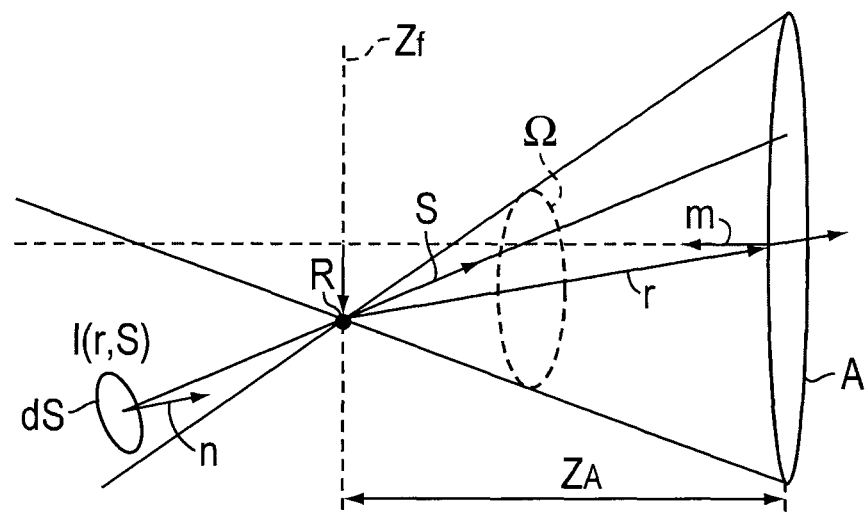

Referring now to FIGS. 19A and 19B, in which like elements of FIGS. 18A-18D are shown having like reference designations, the aperture, A, is associated with the imagining system of FIG. 18A. Here, the focal plane does not lie on a surface, S, of an object being imaged. Therefore, the surface, S, is substantially out of focus. Also, the in-focus point R is not on the surface, S, to be imaged.

From equation (23), the total collected power at the point, R', is equivalent to the total power radiated by the point, R, into the solid angle, $\Omega$, defined by point, R, and the area, A, of the aperture, A.

Figure 19C:
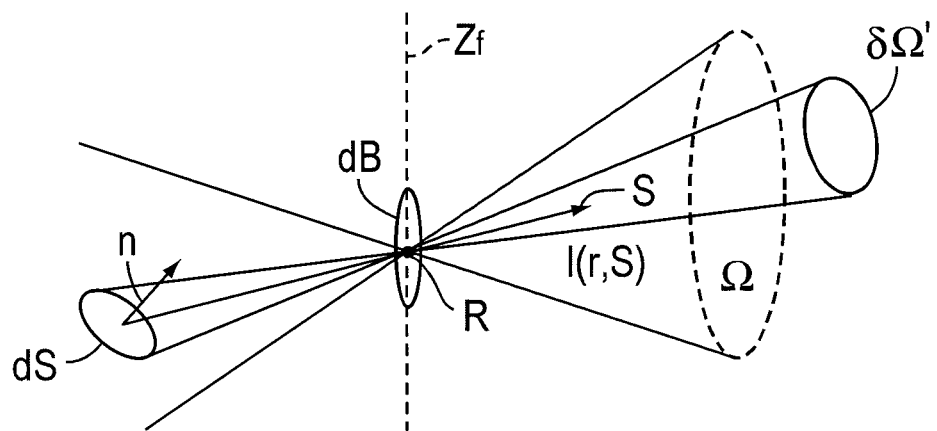

Referring now to FIG. 19C, in which like elements of FIGS. 18A-18D and 19A are shown having like reference designations, a differential surface area, dS, which is out of focus, contributes light energy to point, R'. All of the power that leaves the differential surface area, dS, and passes through the point, R, within the solid angle, $\Omega$, is detected at the point, R'. In order to simplify the calculations, the total power measured at the point, R' (FIG. 19A), is equivalent to the power that traverses the differential surface area, dB, within the solid angle, $\Omega$. As described above, this virtual surface represents the image of the light sensor at the point, R'.

The contribution of the differential surface area, dS, can be calculated. The power radiated must equal the power received. That is, the differential surface area, dS, radiates a certain power into the differential solid angle, $\delta\Omega'$. From this differential radiation, only those values that fall within the solid angle, $\Omega$, will contribute to the total power. Therefore, the differential power measured at the point, R' (FIG. 19A), due to the differential surface area, dS, may be written as:

$$dP(R) = \int_{\Omega'} I_f(R,s)m \cdot sdBd\Omega', \forall s \in \Omega \qquad (32)$$

where $I_f$ is the specific intensity at the focal plane, $Z_f$, the surface normal, m (not shown), is the surface normal of the differential surface area, dB, and the solid angle, $\delta\Omega'$, is defined by the differential surface area, dS, and the point, R.

Figure 19D:
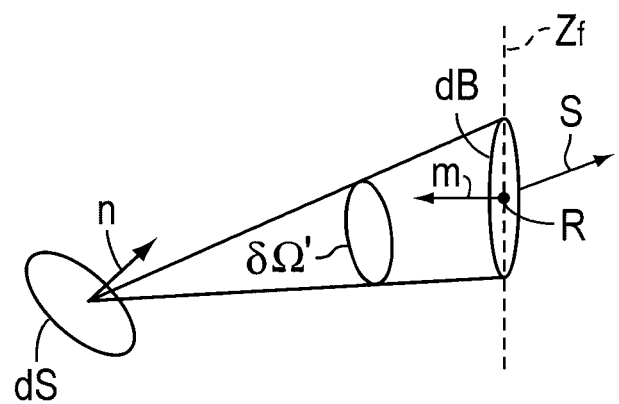

Referring now to FIG. 19D, in which like elements of FIGS. 18A-18D and 19A-19C are shown having like reference designations, another property of the specific intensity, invariance, provides that Equation (32) above can be written in terms of the specific intensity, I(r,s), at the differential surface area, dS:

$$dP(R) = \int_{\Omega'} I(r,s)n \cdot sdSd\Omega', \forall s \in \Omega, \qquad (33)$$

where the solid angle, $\delta\Omega'$, is defined by the differential surface area, dB, and the point r is the surface point at which the differential surface area, dS, is located. It should be recognized that the only values of, s, that contribute to the solid angle integral in Equation (33) are those that fall within the solid angle, $\Omega$ (FIG. 19C). The above equation corresponds to the total power received at the point, R' (FIG. 19A), due to a differential surface area, dS.

Figure 19E:
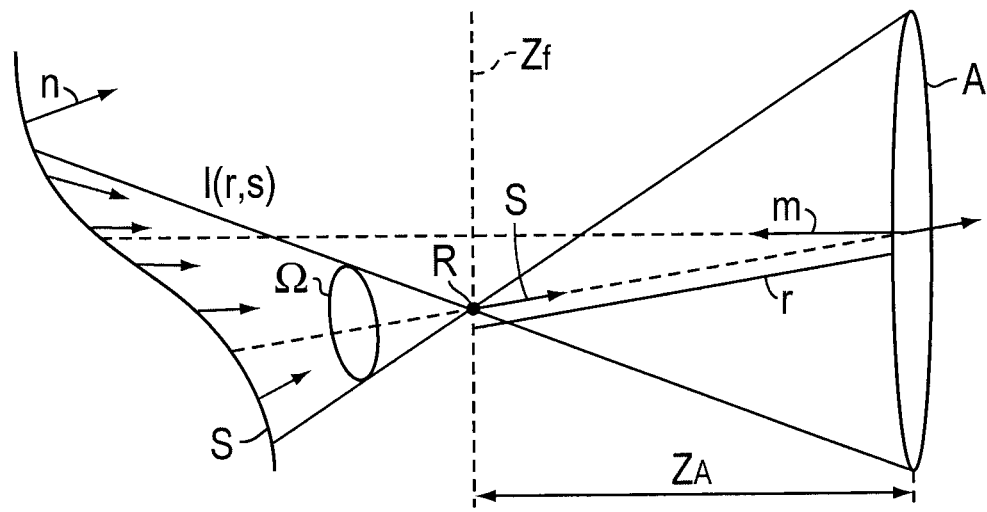

Referring now to FIG. 19E, in which like elements of FIGS. 18A-18D and 19A-19D are shown having like reference designations the total power takes into account the complete surface, for those values that fall within the solid angle, $\Omega$ (FIGS. 19A and 19C) through the differential surface area, dB (FIG. 19C). This is schematically represented in FIG. 19E. The total power received at the point, R' (FIG. 19A), is therefore:

$$P(R) = \int_S dP(R) = \int_S dS \int_I I(r,s)n \cdot sd\Omega', \forall s \in \Omega \qquad (34)$$

Figure 19F:
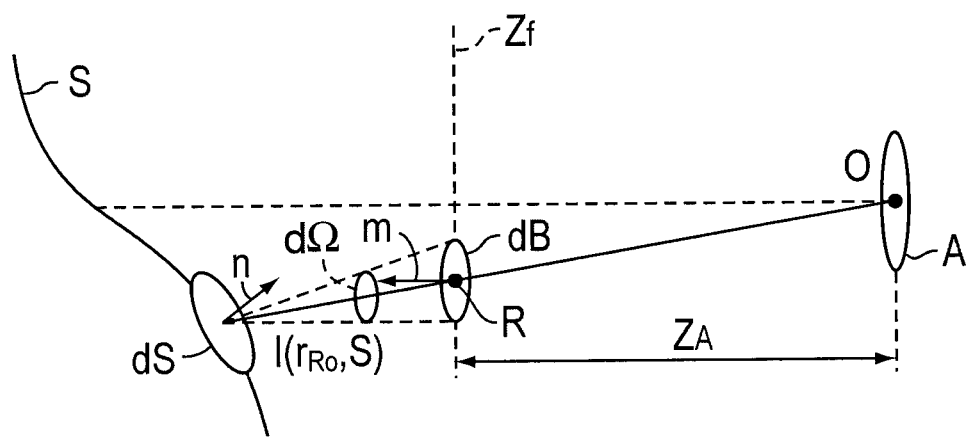

Referring now to FIG. 19F, in which like elements of FIGS. 18A-18D and 19A-19E are shown having like reference designations, for a small aperture, where $Z_A \gg R_A$, and an out of focus surface, S, it is convenient to return to the contribution of a single differential surface area, dS, given in Equation (33). Since the solid angle in this case is a delta function, Equation (33) may be rewritten as follows:

$$dP(R)=I(r,s)n \cdot s\delta(s-u_{r-o})\delta(s-u_{O-R})dSd\Omega', \qquad (35)$$

where the delta functions ensure that the direction of energy that passing through the points, R and O, is taken into account. Rewriting the solid angle, $d\Omega'$, in terms of the differential surface area, dB, we obtain:

$$dP(R) = I(r,s)n \cdot s\delta(s - u_{r-O})\delta(s - u_{O-R})dS \frac{m \cdot sdB}{|r - R|^2}, \qquad (36)$$

which is equivalent to:

$$dP(R) = I(r, u_{r-R})\delta(u_{r-R} - u_{R-O})(u_{r-R} \cdot n)(u_{r-R} \cdot m) \frac{dSdB}{|r - R|^2} \qquad (37)$$

Introducing this expression into Equation (34) an expression for the total power received at the point, R', (FIG. 19A) is:

$$P(R) = I(r_{RO}, u_{R-O})[u_{R-O} \cdot n(r_{RO})][u_{O-R} \cdot m] \frac{dSdB}{|r_{RO} - R|^2} \quad (38)$$

where $r_{RO}$ is the point where the surface, S, and the line given by RO intersect. That is, from Equation (38), in the case of a small aperture only one element of the surface, S, will contribute to the intensity at a certain pixel. This means that for a very small aperture, A, all of surface, S, will be in focus. The differential surface area, dB, represents the image of the light sensor at the focal plane, $Z_f$.

For a large aperture, where $R_A \gg Z_A$, all surface points on the surface, S, contribute to the power measured at the point, R' (FIG. 19A). Rewriting the solid angle in terms of the differential surface area, dB.

$$P(R) = \int_S I(r, u_{r-R})[n \cdot u_{r-R}][m \cdot u_{r-R}] \frac{dBdS}{|r - R|^2} \quad (39)$$

That is, for the points out of focus, there is a complete de-blurring. Therefore, very large apertures have a very sharp focal plane, $Z_f$, or focus depth.

For the expressions where I(r,s) has not been defined explicitly, the above expression includes all high-order angular components of the light at the point, r (FIG. 19E). For an arbitrary surface, S, being imaged, it may be assumed that the transformation of a general point, $r_b$, (equivalent to point r) within the surface, S, and a light detector at a general point, $r_d$ (equivalent to point R) within the focal plane $Z_f$ is as follows:

$$\Gamma(r_d, r_b) = \xi(r_b, r_d) f(n, m) dA_d, \quad (40)$$

In Equation (40) n and m represent the surface normal, n, and the detector normal, m, respectively, as before. Function $\xi$ is a visibility factor that discards surface points not visible from the light sensor, whereas function f includes the angles of acceptance of the aperture, A, with regards to each surface component, defined by n and m. Function $\Gamma(r_b, r_d)$ includes all the high-order angular contributions of light and may therefore be written as $\Gamma(r_b, r_d) = \Sigma_n a_n \Gamma(r_b, r_d)$, where $\oplus^{(n)}(r_b, r_d)$ is the n-order angular contribution, i.e., a function of the n-order Legendre Polynomial, and $a_n$ is the contribution of this order.

Using Equation (40) it is possible to relate a set of light intensities $U(r_s, r_b)$ at the diffuse/non-diffuse air-tissue interface delineated by the surface, S, to non-contact light intensity measurements $U_{nc}(r_s, r_d)$ obtained from a free-space light sensor at $r_d \notin V$, i.e., $$U_{nc}(r_s, r_d) = \sum_{r_b \in S} \Gamma(r_d, r_b) U(r_s, r_b) \Delta S \quad (41)$$

where $\Gamma(r_b, r_d)$ is a matrix. In the case where there is a one to one correspondence (surface in focus), $\Gamma(r_b, r_d)$ will be a diagonal matrix. Equation (41) may also be viewed as a convolution of the surface values with the transformation function $\Gamma(r_b, r_d)$.

The transformation of Equation (41) makes no assumptions regarding the position, orientation, or area of the surface elements or the light detectors but explicitly models these parameters through Equation (40).

Considering a finite set of detectors and surface elements, Equation (41) can be rewritten as a matrix equation where $U_{nc} \in R^{|det|,|src|}$, $\Gamma \in R^{|det|,|S|}$ and $U \in R^{|S|,|src|}$ describe an imaging system with |det| detectors, |src| sources and |S| surface elements. Each matrix element (b,s) in U contains the average intensity on a surface element $r_b \in S$ created by a source $r_s$ as described by Equation (21). Transforming the volume integral into a sum of volume elements (voxels) of volume $\Delta V_r$ leads to the following:

$$U_{b,s} = \sum \Delta V_r \frac{U_0(r_s, r) G(r_b, r) \Gamma(r_b, r_d)}{U_0(r_s, r_b) \Gamma(r_b, r_d)} \frac{v}{D} c(r) \quad (42)$$

where the sum is performed over all the elements within V.

Equation (42) can be considered to be the product of a matrix $W \in R^{|S|,|V|}$ with a vector $c \in R^{|V|}$, where the matrix contains all the factors in Equation (42) except for c. Thus, the complete discrete system can be written $U_{nc} = Wc$. As W tends to be very large, the inversion cannot be performed directly. Instead, iterative techniques, such as the algebraic reconstruction technique with randomized projection order (R-ART) can be used, conjugate minimization methods, or other methods.

Systems of the invention may include a computer which executes software that controls the operation of one or more instruments, and/or that processes data obtained by the system. The software may include one or more modules recorded on machine-readable media such as magnetic disks, magnetic tape, CD-ROM, and semiconductor memory, for example. The machine-readable medium may be resident within the computer or can be connected to the computer by a communication link (e.g., access via internet link). However, in alternative embodiments, one can substitute computer instructions in the form of hardwired logic for software, or one can substitute firmware (i.e., computer instructions recorded on devices such as PROMs, EPROMS, EEPROMs, or the like) for software. The term machine-readable instructions as used herein is intended to encompass software, hardwired logic, firmware, object code and the like.

The computer is preferably a general purpose computer. The computer can be, for example, an embedded computer, a personal computer such as a laptop or desktop computer, or another type of computer, that is capable of running the software, issuing suitable control commands, and/or recording information in real-time. The computer may include a display for reporting information to an operator of the instrument (e.g., displaying a tomographic image), a keyboard for enabling the operator to enter information and commands, and/or a printer for providing a print-out, or permanent record, of measurements made by the system and for printing diagnostic results, for example, for inclusion in the chart of a patient. In certain embodiments, some commands entered at the keyboard enable a user to perform certain data processing tasks. In certain embodiments, data acquisition and data processing are automated and require little or no user input after initializing the system.

EQUIVALENTS

While the invention has been particularly shown and described with reference to specific preferred embodiments, it should be understood by those skilled in the art that various changes in form and detail may be made therein without departing from the spirit and scope of the invention as defined by the appended claims. The relevant teachings of all the references, patents and patent applications cited herein are incorporated herein by reference in their entirety.

What is claimed is:

1. A system for creating an optical tomographic image of a target volume of an object, the system comprising:
   an x-ray source configured to direct x-ray radiation into the object;
   an x-ray detector configured to detect x-ray radiation transmitted through the object;
   a light source configured to direct light into the object;
   a light detector configured to detect light transmitted through and/or emitted from the object, wherein
   the x-ray detector is configured to detect x-ray radiation at a first plurality of angular projections, collecting one or more images of an x-ray scan data set at each of the first plurality of angular projections, and
   the light detector is configured to detect light at a second plurality of angular projections, collecting one or more images of a light scan data set at each of the second plurality of angular projections;
   a memory for storing code that defines a set of instructions; and
   a processor for executing the set of instructions to create a three-dimensional optical absorption map of the target volume based at least in part on the x-ray scan data set and to use the optical absorption map and light scan data set to construct a forward problem and solve an inverse problem in optical tomographic reconstruction, thereby creating the three dimensional optical tomographic image, wherein the optical absorption map reflects anatomical information obtained from the x-ray scan data by distinguishing a plurality of tissues of various densities within the object,
   wherein the optical absorption map comprises a plurality of absorption coefficients assigned to regions of different densities, where each of the plurality of absorption coefficients is a perturbation from a background absorption coefficient and is computed as a function of an x-ray-derived measure of density, and where each of the plurality of absorption coefficients provides a measure of optical absorption at a wavelength of the detected light.

2. The system of claim 1, wherein the light source is configured to direct excitation light into the object at multiple locations and the x-ray source is configured to direct x-ray radiation into the object at multiple locations by operation of one or more of the following:
   (i) rotation of a gantry about the imaging chamber, wherein the light source and the light detector are mounted to the gantry;
   (ii) fine scanning of a light head of the light source at one or more positions of a gantry, wherein the light source and the light detector are mounted to the gantry; and
   (iii) passive splitting of a single beam from the light source into multiple beams.

3. The system of claim 1, wherein the x-ray source is configured to direct x-ray radiation into the object at multiple locations.

4. The system of claim 1, wherein the three-dimensional optical absorption map comprises absorption coefficients corresponding to a plurality of segmented regions of the target volume.

5. The system of claim 1,
   wherein the instructions, when executed, cause the processor to perform the operations of creating a surface model of at least a portion of the object based at least in part on the detected x-ray radiation; and
   wherein creating the tomographic image comprises using the surface model in the optical tomographic reconstruction.

6. The system of claim 5, wherein the surface model provides one or more boundary conditions used in the optical tomographic reconstruction to create the tomographic image.

7. The system of claim 1, comprising a coordinated light source and sensor configured to determine a surface model of at least a portion of a three-dimensional surface of the object.

8. The system of claim 7, wherein creating the tomographic image comprises using the surface model in the optical tomographic reconstruction.

9. The system of claim 8, wherein the surface model provides one or more boundary conditions used in the optical tomographic reconstruction.

10. The system of claim 1, wherein the instructions, when executed, cause the processor to perform the operations of:
    creating a three-dimensional anatomical dataset using the detected x-ray radiation; and
    registering the anatomical dataset with the tomographic image to create a composite image.

11. The system of claim 1, wherein the light source is configured to direct excitation light into the object at multiple locations.

12. The system of claim 11, wherein the excitation light has wavelength within a range from 550 nm to 1300 nm.

13. The system of claim 11, wherein the excitation light has wavelength within a range from 650 nm to 900 nm.

14. The system of claim 11, wherein the detected light comprises excitation light from the light source that has been transmitted through the object and fluorescent light emitted from one or more fluorophores within the object.

15. The system of claim 14, wherein the fluorescent light is emitted from the one or more fluorophores as a result of excitation by the excitation light.

16. The system of claim 14, wherein the one or more fluorophores comprises an endogenous fluorophore.

17. The system of claim 14, wherein the one or more fluorophores comprises an exogenous fluorophore.

18. The system of claim 14, wherein the one or more fluorophores comprises at least one member selected from the group consisting of a molecular probe, an activatable probe, an enzyme-activatable probe, a quantum dot-based imaging probe, a nanoparticle-based imaging probe, a probe targeted to a biomolecule, a wavelength shifting beacon, a multicolor probe, a probe with high binding affinity to a target, a non-specific imaging probe, labeled cells, x-ray contrast agent, magnetic resonance contrast agent, a dual modality agent, an optical/CT dual modality agent, an optical/MR dual modality agent, a lanthanide metal-ligand probe, and any combination thereof.

19. The system of claim 14, wherein the one or more fluorophores comprises a probe targeted to a biomarker, a molecular structure, a mineral, and/or a biomolecule.

20. The system of claim 19, wherein the probe is targeted to a biomolecule, wherein the biomolecule comprises at least one member selected from the group consisting of an antibody, a protein, a glycoprotein, a cell receptor, a neurotransmitter, an integrin, a growth factor, a cytokine, a lymphokine, a lectin, a selectin, a toxin, a carbohydrate, an internalizing receptor, an enzyme, a protease, a virus, a bacteria, a microorganism, and any combination thereof.

21. The system of claim 14, wherein:
the light scan data set comprises data corresponding to both the detected excitation light transmitted through the object and the detected fluorescent light emitted from the one or more fluorophores within the object; and creating the tomographic image comprises processing both the detected excitation light and the detected fluorescent light of the light scan data set.

22. The system of claim 1, wherein the object is an animal.

23. The system of claim 1, wherein the object is a mammal.

24. The system of claim 1, wherein the object is a human.

25. The system of claim 1, comprising a plurality of x-ray sources configured to direct x-ray radiation into the object and corresponding x-ray detectors configured to detect x-ray radiation transmitted through the object, the x-ray sources and x-ray detectors disposed about the imaging chamber.

26. The system of claim 25, wherein the plurality of x-ray sources have different beam energies.

27. The system of claim 1, further comprising a display configured to display the tomographic image.

28. The system of claim 1, wherein a receiving portion of the light detector nearest to a surface of the object is no more than about 1 mm from the surface of the object.

29. The system of claim 1, wherein a receiving portion of the light detector nearest to a surface of the object is greater than about 1 mm from the surface of the object.

30. The system of claim 1, wherein a receiving portion of the light detector nearest to a surface of the object is no more than about 1 cm from the surface of the object.

31. The system of claim 1, wherein a receiving portion of the light detector nearest to a surface of the object is greater than about 1 cm from the surface of the object.

32. The system of claim 31, wherein an index-matching fluid is located between the receiving portion of the light detector and the surface of the object.

33. The system of claim 30, wherein a non-turbid medium is located between the receiving portion of the light detector and the surface of the object.

34. The system of claim 33, wherein the non-turbid medium is air.

35. The system of claim 1, wherein the light detector comprises a CCD camera.

36. The system of claim 35, wherein the CCD camera is a time-gated intensified CCD camera.

37. A method for creating an optical tomographic image of a target volume of an object, the method comprising:
obtaining an x-ray scan data set, wherein the x-ray scan data set comprises a plurality of x-ray images obtained by transmitting x-ray radiation through an object at a first plurality of angular projections, wherein each angular projection of the first plurality of angular projections is associated with at least one image of the plurality of x-ray images;

obtaining a light scan data set, wherein the light scan data set comprises a plurality of images obtained by detecting light transmitted through and/or emitted from the object at a second plurality of angular projections, wherein each angular projection of the second plurality of angular projections is associated with at least one image of the plurality of images;

constructing, by a processor of a computing device, a three-dimensional optical absorption map of the target volume, wherein the three-dimensional optical absorption map is based at least in part on the x-ray scan data set, and the three-dimensional optical absorption map reflects anatomical information obtained from the x-ray scan data by distinguishing a plurality of tissues of various densities within the object, wherein the optical absorption map comprises a plurality of absorption coefficients assigned to regions of different densities, where each of the plurality of absorption coefficients is a perturbation from a background absorption coefficient and is computed as a function of an x-ray-derived measure of density, and where each of the plurality of absorption coefficients provides a measure of optical absorption at a wavelength of the detected light;

determining, by the processor, a forward problem based in part upon the optical absorption map and light scan data set;

solving, by the processor, an inverse problem in optical tomographic reconstruction, wherein the inverse problem is solved using the forward problem, and solving the inverse problem comprises determining a reconstruction solution; and creating, by the processor, optical tomographic image data based on the reconstruction solution, wherein the optical tomographic image data is configured for presentation upon a display.

38. The method of claim 37, wherein:
constructing the three-dimensional optical absorption map comprises
determining a plurality of regions of the x-ray scan data set, and
assigning, for each of one or more regions of the plurality of regions, a respective absorption coefficient value of one or more absorption coefficient values; and determining the forward problem comprises applying the one or more absorption coefficient values to the forward problem.

39. The method of claim 38, wherein each absorption coefficient value of the one or more absorption coefficient values signifies a respective departure from an average absorption coefficient.

40. The method of claim 38, comprising:
determining, for each region of the plurality of regions,
a respective absorption coefficient, and
a respective perturbation in optical absorption; wherein
each absorption coefficient value of the one or more absorption coefficient values conforms to a perturbation equation of $(\mu_\alpha)_i = \mu_\alpha \cdot (1+\delta_i)$, wherein
$\mu_\alpha$ is an average absorption coefficient,
$(\mu_\alpha)_i$ is a respective absorption coefficient i assigned to a region i, and
$\delta_i$ is a respective perturbation i assigned to the region i.

41. The method of claim 40, wherein:
the respective perturbation i is evaluated to be:

$$\delta_i = \frac{1}{N \cdot (HU)_b} \cdot \sum_{j=1}^{N} (HU)_j,$$

wherein
$(HU)_b$ is an x-ray CAT-derived measure of density for average background tissue of the target object, wherein $(HU)_b$ is measured in Houndsfield Units, (HU)$_j$ is a respective measure of density for a plurality of CAT-reconstructed voxels in the region i, and
the region i comprises N voxels.

42. The method of claim 40, wherein using the forward problem to solve the inverse problem comprises using a distribution of $(\mu_\alpha)_i$ absorption coefficients rather than the average absorption coefficient.

43. The method of claim 38, comprising:
determining, for each region of the plurality of regions, one or more external regions, wherein
the one or more external regions are considered to be outside the target volume,
the plurality of images were obtained at least in part by detecting fluorescent light emitted from one or more fluorophores within the object, and
solving the inverse problem comprises assuming a fluorophore concentration is zero in each external region of the one or more external regions.

44. The system of claim 4, wherein creating the optical tomographic image comprises applying the absorption coefficients to the forward problem.

45. The system of claim 44, wherein the absorption coefficients each signify a respective departure from an average absorption coefficient.

46. The system of claim 1, wherein the instructions, when executed, cause the processor to perform the operations of:
determining, for each region of a plurality of regions of the target volume,
a respective absorption coefficient,
a respective perturbation in optical absorption, and
a respective perturbative index, wherein
the respective perturbative index signifies a departure from an average background absorption coefficient, and
the respective perturbative index conforms to a perturbation equation of $(\mu_\alpha)_i = \mu_\alpha \cdot (1+\delta_i)$, wherein
$\mu_\alpha$ is the average background absorption coefficient,
$(\mu_\alpha)_i$ is the respective absorption coefficient i, and
$\delta_i$ is the respective perturbation i.

47. The system claim 46, wherein:
the respective perturbation i is evaluated to be:

$$\partial_i = \frac{1}{N \cdot (HU)_b} \cdot \sum_{j=1}^{N} (HU)_j,$$

wherein
(HU)$_b$ is an x-ray CAT-derived measure of density for average background tissue of the target object, wherein (HU)$_b$ is measured in Houndsfield Units,
(HU)$_j$ is a respective measure of density for a plurality of CAT-reconstructed voxels in the region i, and
the region i comprises N voxels.

48. The system of claim 46, wherein using the forward problem to solve the inverse problem comprises using a distribution of $(\mu_\alpha)_i$ absorption coefficients rather than the average absorption coefficient.

49. The system of claim 46, wherein the instructions, when executed, cause the processor to perform the operations of:
determining, for each region of the plurality of regions, one or more external regions, wherein
the one or more external regions are considered to be outside the target volume,
the plurality of images were obtained at least in part by detecting fluorescent light emitted from one or more fluorophores within the object, and
solving the inverse problem comprises assuming a fluorophore concentration is zero in each external region of the one or more external regions.

50. The system of claim 1, wherein:
the three-dimensional optical absorption map comprises a plurality of positions, wherein each position is assigned at least one value; and
constructing the forward problem and solving the inverse problem comprises expressing the values of the three-dimensional optical absorption map in terms of a position-dependent departure from an average absorption coefficient.

51. The system of claim 50, wherein the position-dependent departure from the average absorption coefficient is a perturbation.

52. The system of claim 1, wherein the processor is configured to, prior to solving the inverse problem:
identify one or more regions external to the target volume; and
for each region of the one or more regions external to the target volume, set fluorophore concentration equal to zero.

53. The method of claim 37, wherein:
the three-dimensional optical absorption map comprises a plurality of positions, wherein each position is assigned at least one value; and
determining the forward problem and solving the inverse problem comprises expressing the values of the three-dimensional optical absorption map in terms of a position-dependent departure from an average absorption coefficient.

54. The method of claim 53, wherein the position-dependent departure from the average absorption coefficient is a perturbation.

55. The method of claim 37, further comprising, prior to solving the inverse problem:
identifying one or more regions external to the target volume; and
for each region of the one or more regions external to the target volume, setting fluorophore concentration equal to zero.

56. The system of claim 1, wherein the three-dimensional optical absorption map is expressed in terms of a position-dependent departure from an average absorption coefficient in the construction of the forward problem and solution of the inverse problem.

* * * * *